US005861155A

United States Patent [19]
Lin

[11] Patent Number: 5,861,155
[45] Date of Patent: Jan. 19, 1999

[54] HUMANIZED ANTIBODIES AND USES THEREOF

[75] Inventor: Augustine Y. Lin, Chestnut Hill, Mass.

[73] Assignee: Astra AB, Sodertalje, Sweden

[21] Appl. No.: 652,558

[22] PCT Filed: Nov. 21, 1994

[86] PCT No.: PCT/IB94/00387

§ 371 Date: Jun. 6, 1996

§ 102(e) Date: Jun. 6, 1996

[87] PCT Pub. No.: WO95/16038

PCT Pub. Date: Jun. 15, 1995

[30] Foreign Application Priority Data

Dec. 8, 1993 [GB] United Kingdom .................. 9325182

[51] Int. Cl.$^6$ .................... A61K 39/395; C12P 21/08; C07K 16/00
[52] U.S. Cl. ................... 424/133.1; 424/172.1; 530/387.3; 530/388.22
[58] Field of Search .................... 530/388.22, 389.6, 530/387.3, 388.23; 435/69.7; 424/133.1, 172.1

[56] References Cited

FOREIGN PATENT DOCUMENTS

| | | |
|---|---|---|
| 0036776 | 9/1981 | European Pat. Off. . |
| 0239400 | 9/1987 | European Pat. Off. . |
| 0328404 | 8/1989 | European Pat. Off. . |
| 0403156 | 12/1990 | European Pat. Off. . |
| PCT WO89/07142 | 8/1989 | WIPO . |
| PCT WO90/06758 | 6/1990 | WIPO . |
| WO 90/06758 | 6/1990 | WIPO .............. A61K 35/14 |
| PCT WO90/07861 | 7/1990 | WIPO . |
| PCT WO91/01133 | 2/1991 | WIPO . |
| PCT WO91/09967 | 7/1991 | WIPO . |
| PCT WO91/09968 | 7/1991 | WIPO . |
| WO 91/09967 | 7/1991 | WIPO .............. C12P 21/08 |
| PCT WO92/01568 | 2/1992 | WIPO . |
| PCT WO93/04700 | 3/1992 | WIPO . |
| PCT WO92/08981 | 5/1992 | WIPO . |
| PCT WO92/11018 | 7/1992 | WIPO . |
| PCT WO94/05801 | 3/1994 | WIPO . |

OTHER PUBLICATIONS

Bel let al., T Cell Receptors, p. 123, Oxford University Press, Jan. 1995.
Abe et al., *J. Exp. Med.*, 177:791–796 (1993).
Abe et al, *Proc. Nati. Acad Sci. USA* 89: 4066–4070 (1992).
Acha–Orbea et al., *Cell*, 54: 263–273 (1988).
Baranov et al., *Gene*, 84: 463–466 (1989).
Bernard et al., "The Epitopic Dissection . . . " 53–66 (Springer Verlag, New York (1984).
Bolivar et al., *Gene*, 2: 95–113 (1977).
Boylston et al., *J. Immunol.*, 137: 741–744 (1986).
Brennan et al., *Clin. Exp. Immunol.*, 73: 417–423 (1988).
Chang et al., *Nature*, 275: 617–624 (1978).
DerSimonian et al., *J. Exp. Med.*, 177: 1623–1631 (1993).
Elian et al., *Disease Markers*, 5: 89–99 (1987).
Fiers et al., *Nature*, 273: 113–120 (1978).
Foote et al., *J. Mol. Biol.*, 224: 487–499 (1992).
Francis et al., *Lancet.*, 1: 211 (1986).
Goedell et al., *Nature*, 281: 544–548 (1979).
Goedell et al., *Nuc. Acids Res.*, 8; 4057–4074 (1980).
Grunewald et al., *Eur. J. Immunol*, 22: 129–135 (1992).
Hakimi et al., *J. Immunol.*, 151: 1075–1085 (1993).
Hess et al., *J. Adv. Enzyme Reg.*, 7: 149–167 (1968).
Higuchi. et al., *Nuc. Acids Res.*, 16: 7351–7367 (1988).
Ho et al., *Gene*, 77: 51–59 (1989).
Ho et al., *Immunogenetics*, 15: 509–517 (1982).
Holland et al., *Biochemistry*, 17: 4900–4907 (1978).
Horton et al., *Gene*, 77: 61–68 (1989).
Howell et al., *Proc. Natl. Acad. Sci. USA*, 88: 10921–10925 (1991).
Howell et al. *Science*, 246: 668–670 (1989).
Itakura et al., *Science.*, 198:1056–1063 (1978).
Jaffers et al., *Transplanations*,41: 572–578 (1986).
Jones, *Genetics*, 85: 23–33 (1977).
Jones et al., *Nature*, 321: 522–525 (1986).
Kabat et al., U.S. Dept. Of Health and Human Services, 5th ed. NIH Publication No. 91, 3242 (1991).
Kanasawa et al, *Diabetologia*, 27: 133–155 (1984).
Kingsman et al., *Gene*, 7: 141–152 (1979).
Knight et al., *J. Exp. Med.*, 147:1653–1660 (1978).
Kohler et al., *Nature*, 256: 495–497 (1975).
Kotzin et al., *Proc. Natl. Acad. Sci. USA*, 88: 9161–9165 (1991).
Kramer et al., *Nuc. Acids Res.*, 10: 6475–6485 (1982).
Lin et al., *Science*, 249: 677–679 (1990).
Lindstrom et al., *Adv. Immunol.*, 42: 233–284 (1988).
Maron et al., *J. Exp. Med.*, 152: 1115–1120 (1980).
McFarlin et al., *Science*, 179: 478–480 (1973).
Mullis et al., *Meth. Enz.*, 155: 335–350 (1987).
Norris et al., *Nuc. Acids Res.*, 11: 5103–5112 (1983).
Oksenberg et al., *Nature*, 345: 344–346 (1990).
Oksenberg et al., *Nature*, 362: 68–70 (1993).

(List continued on next page.)

*Primary Examiner*—Frank C. Eisenschenk
*Assistant Examiner*—Patrick Nolan
*Attorney, Agent, or Firm*—Kathleen Madden Williams; Banner & Witcoff, Ltd.

[57] ABSTRACT

The present invention relates to humanized antibodies and binding proteins thereof, capable of binding to T cells exhibiting particular variable beta chains, and particularly those subpopulations expressing human V beta 5.2 and/or 5.3, and V beta 8.1. The present invention also relates to the preparation of such antibodies, to pharmaceutical compositions containing them, and therapeutic utilization of the antibodies, specifically in autoimmune diseases.

13 Claims, 6 Drawing Sheets

OTHER PUBLICATIONS

Orlandi et al., *Proc. Natl. Acad. Sci. USA*, 86: 3833–3837 (1989).
Paliard et al., *Science*, 253: 325–329 (1991).
Paterson, Textbook of Immunopathology, pp. 179–188 (Mischer et al., eds.) (Grune & Stratton, NY 1986).
Paul et al., *Science*, 195: 1293–1300 (1987).
Posnett et al. *J. Clin. Invest.*, 85: 1770–1776 (1990).
Queen et al., *Proc. Natl. Acad. Sci. USA*, 86: 10029–10033 (1989).
Ralfkiaer et al., *Brit. J. Derm.*, 125: 409–412 (1991).
Reichmann et al, *Nature*, 332: 323–327 (1988).
Reinersten et al., *New Eng. J. Med.*, 299: 515–518 (1978).
Sanger et al., *Proc. Natl. Acad. Sci. USA*, 74: 5463–5467 (1977).
Satoh et al., *J. Immunol.*, 138: 179–184 (1987).
Schmidt et al, *Hoppe–Seyler's Z. Phsiol. Chem.*, 364:713–747 (1983).
Shalon, et al., *Autoimmunity*, 17:301–307 (1994).
Siebenlist et al., *Cell*, 20: 269–281 (1980).
Smith et al., *Nature*, 337: 181–184 (1989).
Spencer et al., *J. Clin. Pathol.*, 44: 915–918 (1991).
Spielman et al., *Epidemiol. Rev.*, 4: 46–65 (1982).
Stamenkovic et al., *Proc. Natl. Acad. Sci. USA*, 85: 1179–1183 (1988).
Stinchcomb et al., *Nature*, 282: 39–43 (1979).
Stuart et al., *Ann. Rev. Immunol.*, 42: 199–218 (1984).
Takebe et al., *Mol. Cell. Biol.*, 8: 466–472 (1988).
Teraski et al., *Science*, 1933: 1244–1247 (1976).
Trejdosiewicz et al., *Clin. Exp. Immunol.*, 84: 440–444 (1991).
Tschemper et al., *Gene*, 19: 157 (1980).
Uematsu et al., *Proc. Natl. Acad. Sci. USA*, 88:8534–8538 (1991).
Urban et al., *Cell*, 54:577–592 (1988).
Van Eden et al., *Nature*, 331: 171–173 (1988).
Van Kerckhove et al., *J. Exp. Med.*, 175: 57–63 (1992).
van Shooten et al., *Proc. Natl. Acad. Sci. USA*, 89: 11244–11248 (1992).
Vandenbark et al., *Nature*, 341: 541–544 (1989).
Verhoeyen et al. *Science*, 239: 1534–1536 (1988).
Wang et al., *Proc. Natl. Acad. Sci. USA*, 90: 4156–4160 (1993).
Wucherpfenning et al., *Science*, 248: 1016–1019 (1990).
Zoller, et al., *DNA*, 3: 479–488 (1984).
Zoller, et al., *Nuc. Acids Res.*,10: 6487–6501 (1982).

```
                     10          20          30          40          50
                      *           *           *           *           *
TM23  V_L    DIQMTQTTSSLSASLGDRVTISCCSASQGISNYLNWYQQKPDGTVKLLIYY
TM27  V_L    DIQMTQSPSSLSASVGDRVTITCSASQGISNYLNWYQQTPGKAPKLLIYY-
                                              CDR1

60          70          80          90         100
                      *           *           *           *           *
             TSSLHSGVPSRFSGSGSGTDYSLTIISNLEPEDIATYYCQQYSKLPRTFGG
             TSSLHSGVPSRFSGSGSGTDYTFTISSLQPEDIATYYCQQYSKLPRTFGQ
                CDR2                                          CDR3

107
                      *
             GTKVEIK
             GTKLQIT 10          20          30          40          50
                      *           *           *           *           *
TM23    V_H  QVQLKESGPGLVAPSQSLSITCTVSGFSLTAYGVNWVRQPPGKGLEWLGM
TM27L   V_H  QVQLQESGPGLVRPSQTLSLTCTVSGFSLTAYGVNWVRQPPGRGLEWLGM
TM27I   V_H  ================================AYGVN===========I=M
TM27.1V_H    ================================AYGVN===========L=M
TM27.2V_H    ================================AYGVN===========L=M
TM27.3V_H    ================================AYGVN===========L=M
                                                 CDR1
```

| FIG. 1A |
|---|
| FIG. 1B |

```
                60        70        80        90       100
                 *         *         *         *         *
IWGDGNTDYNSALKSRLSISKDNSKSQVFLKMNSLQTDDTARYYCARDRV
IWGDGNTDYNSALKSRVTMLKDTSKNQFSLRLSSVTAADTAVYYCARDRV
IWGDGNTDYNSALK=================================DRV
IWGDGNTDYNSALK===========VF====================DRV
IWGDGNTDYNSALK==LSIS==N========================DRV
IWGDGNTDYNSALK==============================R==DRV
              CDR2

110       120
        *         *
TATLYAMDYWGQGTSVTVSS
TATLYAMDYWGQGSLVTVSS
TATLYAMDY==========
TATLYAMDY==========
TATLYAMDY==========
TATLYAMDY==========
  CDR3
```

```
              10         20         30         40         50
               *          *          *          *          *
16G8  V_L   ENVLTQSPAIMSASLGEKVTMSCRASSSVNYIYWYQQKSDASPKLWIYYT
TM29  V_L   DIQMTQSPSSLSASVGDRVTITCRASSSVNYIYWYQQTPGKAPKLLIYYT
                                        CDR1

60         70         80         90        100
               *          *          *          *          *
            SNLAPGVPTRFSGSGSGNSYSLTISSMEGEDAATYYCQQFTSSPFTFGSG
            SNLAPGVPSRFSGSGSGTDYTFTISSLQPEDIATYYCQQFTSSPFTFGQG
              CDR2                                CDR3

106
              *
            TKLEIK
            TKLQIT
```

FIG. 2B

```
              10         20         30         40         50
               *          *          *          *          *
16G8   V_H  DVQLVESGGGLVQPGGSRKLSCAASGFTFSNFGMHWVRQAPDKGLEWVAY
TM29   V_H  EVQLVESGGGVVQPGRSLRLSCSSSGFTFSNFGMHWVRQAPGKGLEWVAY
TM29.1 V_H  ===================AA========NFGMH===============Y
TM29.2 V_H  =============================NFGMH===============Y
TM29.3 V_H  =============================NFGMH================
                                             CDR1
```

```
         60         70         80         90        100
          *          *          *          *          *
ISSGSSTIYYADTLKGRFTISRDNPKNTLFLQMTSLRSEDTAMYYCARRG
ISSGSSTIYYADTLKGRFTISRDNSKNTLFLQMDSLRPEDTGVYFCARRG
ISSGSSTIYYADTLKG===============================RG
ISSGSSTIYYADTLKG======P========================RG
ISSGSSTIYYADTLKG=========================AM=Y===RG
      CDR2
```

```
    110    117
     *      *
EGAMDYWGQGTSVTVSS
EGAMDYWGQGTPVTVSS
EGAMDY===========
EGAMDY===========
EGAMDY===========
  CDR3
```

FIG. 2B

| MURINE 4H11 | $y = 393.85 - 5.0535x$ | $R^2 = 0.985$ |
|---|---|---|
| TM27L/NSO | $y = 415.77 - 2.3218x$ | $R^2 = 0.939$ |
| TM27L/CHO | $y = 415.64 - 2.1880x$ | $R^2 = 0.987$ |

| µG/ML | %UNLABELED | MURINE4H11 | TM27L/NSO | TM27L/CHO |
|---|---|---|---|---|
| 5.000 | 50.000 | 149.687 | 303.633 | 299.073 |
| 3.750 | 42.900 | 181.330 | 296.867 | 328.207 |
| 2.500 | 33.300 | 219.803 | 349.850 | 342.667 |
| 1.875 | 27.300 | 251.783 | 367.640 | 358.120 |
| 1.250 | 20.000 | 288.993 | 360.657 | 374.003 |
| 0.938 | 15.800 | 308.113 | 380.870 | 378.773 |
| 0.625 | 11.100 | 333.177 | 388.950 | 395.623 |
| 0.312 | 5.900 | 349.383 | 405.483 | 401.297 |
| 0.156 | 3.030 | 380.860 | 400.113 | 402.853 |
| 0.000 | 0.000 | 417.797 | 417.797 | 417.792 |

SEQUENCE LISTING ( 1 ) GENERAL INFORMATION:

( i i i ) NUMBER OF SEQUENCES: 52

( 2 ) INFORMATION FOR SEQ ID NO: 1:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 1:

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Ser Ser Val Asn Tyr Ile
                20                  25                  30
Tyr Trp Tyr Gln Gln Thr Pro Gly Lys Ala Pro Lys Leu Leu Ile Tyr
            35                  40                  45
Tyr Thr Ser Asn Leu Ala Pro Gly Val Pro Ser Arg Phe Ser Gly Ser
        50                  55                  60
Gly Ser Gly Thr Asp Tyr Thr Phe Thr Ile Ser Ser Leu Gln Pro Glu
 65                 70                  75                  80
Asp Ile Ala Thr Tyr Tyr Cys Gln Gln Phe Thr Ser Ser Pro Phe Thr
                85                  90                  95
Phe Gly Gln Gly Thr Lys Leu Gln Ile Thr
                100                 105
```

( 2 ) INFORMATION FOR SEQ ID NO: 2:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 2:

```
Asp Ile Gln Met Thr Gln Ser Pro Ser Ser Leu Ser Ala Ser Val Gly
 1               5                  10                  15
Asp Arg Val Thr Ile Thr Cys Ser Ala Ser Gln Gly Ile Ser Asn Tyr
                20                  25                  30
Leu Asn Trp Tyr Gln Gln Thr Pro Gly Lys Ala Pro Lys Leu Leu Ile
```

| | | | | 35 | | | | | 40 | | | | | 45 | | | |
|---|---|---|---|---|---|---|---|---|---|---|---|---|---|---|---|---|---|

Tyr Tyr Thr Ser Ser Leu His Ser Gly Val Pro Ser Arg Phe Ser Gly
    50                          55                          60

Ser Gly Ser Gly Thr Asp Tyr Thr Phe Thr Ile Ser Ser Leu Gln Pro
65                          70                    75                    80

Glu Asp Ile Ala Thr Tyr Tyr Cys Gln Gln Tyr Ser Lys Leu Pro Arg
                85                    90                          95

Thr Phe Gly Gln Gly Thr Lys Leu Gln Ile Thr
            100                105

( 2 ) INFORMATION FOR SEQ ID NO: 3:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 3:

Glu Val Gln Leu Val Glu Ser Gly Gly Val Val Gln Pro Gly Arg
1              5                    10                    15

Ser Leu Arg Leu Ser Cys Ser Ser Gly Phe Thr Phe Ser Asn Phe
            20                  25                    30

Gly Met His Trp Val Arg Gln Ala Pro Gly Lys Gly Leu Glu Trp Val
        35                    40                    45

Ala Tyr Ile Ser Ser Gly Ser Ser Thr Ile Tyr Tyr Ala Asp Thr Leu
    50                    55                    60

Lys Gly Arg Phe Thr Ile Ser Arg Asp Asn Ser Lys Asn Thr Leu Phe
65                      70                  75                80

Leu Gln Met Asp Ser Leu Arg Pro Glu Asp Thr Gly Val Tyr Phe Cys
            85                  90                  95

Ala Arg Arg Gly Glu Gly Ala Met Asp Tyr Trp Gly Gln Gly Thr Pro
            100                105              110

Val Thr Val Ser Ser
        115

( 2 ) INFORMATION FOR SEQ ID NO: 4:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 4:

Gln Val Gln Leu Gln Glu Ser Gly Pro Gly Leu Val Arg Pro Ser Gln
1              5                    10                    15

Thr Leu Ser Leu Thr Cys Thr Val Ser Gly Phe Ser Leu Thr Ala Tyr
            20                  25                    30

Gly Val Asn Trp Val Arg Gln Pro Pro Gly Arg Gly Leu Glu Trp Leu
        35                    40                    45

Gly Met Ile Trp Gly Asp Gly Asn Thr Asp Tyr Asn Ser Ala Leu Lys
    50                    55                    60

Ser Arg Val Thr Met Leu Lys Asp Thr Ser Lys Asn Gln Phe Ser Leu
65                      70                  75                80

Arg Leu Ser Ser Val Thr Ala Ala Asp Thr Ala Val Tyr Tyr Cys Ala

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |

Arg Asp Arg Val Thr Ala Thr Leu Tyr Ala Met Asp Tyr Trp Gly Gln
              100                     105                     110

Gly Ser Leu Val Thr Val Ser Ser
              115             120

(2) INFORMATION FOR SEQ ID NO: 5:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Gln Val Gln Leu Gln Glu Ser Gly Pro Gly Leu Val Arg Pro Ser Gln
1               5                       10                      15

Thr Leu Ser Leu Thr Cys Thr Val Ser Gly Phe Ser Leu Thr Ala Tyr
              20                      25                      30

Gly Val Asn Trp Val Arg Gln Pro Pro Gly Arg Gly Leu Glu Trp Leu
              35                      40                      45

Gly Met Ile Trp Gly Asp Gly Asn Thr Asp Tyr Asn Ser Ala Leu Lys
50                              55                      60

Ser Arg Val Thr Met Leu Lys Asp Thr Ser Lys Asn Gln Phe Ser Leu
65                      70                      75                      80

Arg Leu Ser Ser Val Thr Ala Ala Asp Thr Ala Val Tyr Tyr Cys Ala
                    85                      90                      95

Arg Asp Arg Val Thr Ala Thr Leu Tyr Ala Met Asp Tyr Trp Gly Gln
              100                     105                     110

Gly Ser Leu Val Thr Val Ser Ser
              115             120

(2) INFORMATION FOR SEQ ID NO: 6:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Gln Val Gln Leu Gln Glu Ser Gly Pro Gly Leu Val Arg Pro Ser Gln
1               5                       10                      15

Thr Leu Ser Leu Thr Cys Thr Val Ser Gly Phe Ser Leu Thr Ala Tyr
              20                      25                      30

Gly Val Asn Trp Val Arg Gln Pro Pro Gly Arg Gly Leu Glu Trp Ile
              35                      40                      45

Gly Met Ile Trp Gly Asp Gly Asn Thr Asp Tyr Asn Ser Ala Leu Lys
50                              55                      60

Ser Arg Val Thr Met Leu Lys Asp Thr Ser Lys Asn Gln Phe Ser Leu
65                      70                      75                      80

Arg Leu Ser Ser Val Thr Ala Ala Asp Thr Ala Val Tyr Tyr Cys Ala
                    85                      90                      95

Arg Asp Arg Val Thr Ala Thr Leu Tyr Ala Met Asp Tyr Trp Gly Gln
              100                     105                     110

Gly Ser Leu Val Thr Val Ser Ser 115 120

( 2 ) INFORMATION FOR SEQ ID NO: 7:

( i ) SEQUENCE CHARACTERISTICS:
( A ) LENGTH: 120 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 7:

| Gln | Val | Gln | Leu | Gln | Glu | Ser | Gly | Pro | Gly | Leu | Val | Arg | Pro | Ser | Gln |
|---|---|---|---|---|---|---|---|---|---|---|---|---|---|---|---|
| 1 | | | | 5 | | | | | 10 | | | | | 15 | |
| Thr | Leu | Ser | Leu | Thr | Cys | Thr | Val | Ser | Gly | Phe | Ser | Leu | Thr | Ala | Tyr |
| | | | 20 | | | | 25 | | | | | 30 | | | |
| Gly | Val | Asn | Trp | Val | Arg | Gln | Pro | Pro | Gly | Arg | Gly | Leu | Glu | Trp | Leu |
| | | 35 | | | | 40 | | | | | 45 | | | | |
| Gly | Met | Ile | Trp | Gly | Asp | Gly | Asn | Thr | Asp | Tyr | Asn | Ser | Ala | Leu | Lys |
| | 50 | | | | 55 | | | | | 60 | | | | | |
| Ser | Arg | Val | Thr | Met | Leu | Lys | Asp | Thr | Ser | Lys | Asn | Gln | Val | Phe | Leu |
| 65 | | | | 70 | | | | | 75 | | | | | 80 | |
| Arg | Leu | Ser | Ser | Val | Thr | Ala | Ala | Asp | Thr | Ala | Val | Tyr | Tyr | Cys | Ala |
| | | | 85 | | | | 90 | | | | | 95 | | | |
| Arg | Asp | Arg | Val | Thr | Ala | Thr | Leu | Tyr | Ala | Met | Asp | Tyr | Trp | Gly | Gln |
| | | | 100 | | | | 105 | | | | | 110 | | | |
| Gly | Ser | Leu | Val | Thr | Val | Ser | Ser | | | | | | | | |
| | | 115 | | | | 120 | | | | | | | | | |

( 2 ) INFORMATION FOR SEQ ID NO: 8:

( i ) SEQUENCE CHARACTERISTICS:
( A ) LENGTH: 120 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 8:

| Gln | Val | Gln | Leu | Gln | Glu | Ser | Gly | Pro | Gly | Leu | Val | Arg | Pro | Ser | Gln |
|---|---|---|---|---|---|---|---|---|---|---|---|---|---|---|---|
| 1 | | | | 5 | | | | | 10 | | | | | 15 | |
| Thr | Leu | Ser | Leu | Thr | Cys | Thr | Val | Ser | Gly | Phe | Ser | Leu | Thr | Ala | Tyr |
| | | | 20 | | | | 25 | | | | | 30 | | | |
| Gly | Val | Asn | Trp | Val | Arg | Gln | Pro | Pro | Gly | Arg | Gly | Leu | Glu | Trp | Leu |
| | | 35 | | | | 40 | | | | | 45 | | | | |
| Gly | Met | Ile | Trp | Gly | Asp | Gly | Asn | Thr | Asp | Tyr | Asn | Ser | Ala | Leu | Lys |
| | 50 | | | | 55 | | | | | 60 | | | | | |
| Ser | Arg | Leu | Ser | Ile | Ser | Lys | Asp | Asn | Ser | Lys | Asn | Gln | Phe | Ser | Leu |
| 65 | | | | 70 | | | | | 75 | | | | | 80 | |
| Arg | Leu | Ser | Ser | Val | Thr | Ala | Ala | Asp | Thr | Ala | Val | Tyr | Tyr | Cys | Ala |
| | | | 85 | | | | 90 | | | | | 95 | | | |
| Arg | Asp | Arg | Val | Thr | Ala | Thr | Leu | Tyr | Ala | Met | Asp | Tyr | Trp | Gly | Gln |
| | | | 100 | | | | 105 | | | | | 110 | | | |
| Gly | Ser | Leu | Val | Thr | Val | Ser | Ser | | | | | | | | |
| | | 115 | | | | 120 | | | | | | | | | |

( 2 ) INFORMATION FOR SEQ ID NO: 9:

( i ) SEQUENCE CHARACTERISTICS:

(A) LENGTH: 120 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 9:

| Gln | Val | Gln | Leu | Gln | Glu | Ser | Gly | Pro | Gly | Leu | Val | Arg | Pro | Ser | Gln |
|---|---|---|---|---|---|---|---|---|---|---|---|---|---|---|---|
| 1 | | | | 5 | | | | | 10 | | | | | 15 | |
| Thr | Leu | Ser | Leu | Thr | Cys | Thr | Val | Ser | Gly | Phe | Ser | Leu | Thr | Ala | Tyr |
| | | | 20 | | | | 25 | | | | | 30 | | | |
| Gly | Val | Asn | Trp | Val | Arg | Gln | Pro | Pro | Gly | Arg | Gly | Leu | Glu | Trp | Leu |
| | | 35 | | | | 40 | | | | | 45 | | | | |
| Gly | Met | Ile | Trp | Gly | Asp | Gly | Asn | Thr | Asp | Tyr | Asn | Ser | Ala | Leu | Lys |
| | 50 | | | | 55 | | | | | | 60 | | | | |
| Ser | Arg | Val | Thr | Met | Leu | Lys | Asp | Thr | Ser | Lys | Asn | Gln | Phe | Ser | Leu |
| 65 | | | | | 70 | | | | 75 | | | | | | 80 |
| Arg | Leu | Ser | Ser | Val | Thr | Ala | Ala | Asp | Thr | Ala | Arg | Tyr | Tyr | Cys | Ala |
| | | | | 85 | | | | | 90 | | | | | 95 | |
| Arg | Asp | Arg | Val | Thr | Ala | Thr | Leu | Tyr | Ala | Met | Asp | Tyr | Trp | Gly | Gln |
| | | | 100 | | | | | 105 | | | | | 110 | | |
| Gly | Ser | Leu | Val | Thr | Val | Ser | Ser | | | | | | | | |
| | | 115 | | | | | 120 | | | | | | | | |

(2) INFORMATION FOR SEQ ID NO: 10:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 10:

ATATGCGGCC GCTCATTTAC CCGGAGTCCG GGAGAAGCTC TTAGT   45

(2) INFORMATION FOR SEQ ID NO: 11:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 11:

ATATGCGGCC GCTTAACACT CATTCCTGTT GAAGCTCTTG ACAAT   45

(2) INFORMATION FOR SEQ ID NO: 12:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 12:

GACATTGATG TCTTTGGGGT AGAAGTTGTT   30

(2) INFORMATION FOR SEQ ID NO: 13:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 13:

GGTCACTGGC TCAGGGAAAT AACCCTTGAC 30

( 2 ) INFORMATION FOR SEQ ID NO: 14:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 14:

AGGTSMARCT GCAGSAGTCW GG 22

( 2 ) INFORMATION FOR SEQ ID NO: 15:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 15:

TGAGGAGACG GTGACCGTGG TCCCTTGGCC CCAG 34

( 2 ) INFORMATION FOR SEQ ID NO: 16:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 16:

GACATCCAGC TGACCCAGTC TCCA 24

( 2 ) INFORMATION FOR SEQ ID NO: 17:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 17:

GTTAGATCTC CAGCTTGGTC CC 22

( 2 ) INFORMATION FOR SEQ ID NO: 18:

( i ) SEQUENCE CHARACTERISTICS:
( A ) LENGTH: 21 base pairs
( B ) TYPE: nucleic acid
( C ) STRANDEDNESS: single (D) TOPOLOGY: linear (i i) MOLECULE TYPE: cDNA (x i) SEQUENCE DESCRIPTION: SEQ ID NO: 18:

CCGAGGAAGT TTACTATACT G 21

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 19:

CAGTATAGTA AACTTCCTCG G 21

(2) INFORMATION FOR SEQ ID NO: 20:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 20:

CGACATCGAT GATATCGAAT TCGCGGCCGC CAGCTGGGGC CCTCTAGAC 49

(2) INFORMATION FOR SEQ ID NO: 21:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 21:

CGAGTCTAGA GGGCCCCAGC TGGCGGCCGC GAATTCGATA TCATCGATG 49

(2) INFORMATION FOR SEQ ID NO: 22:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 22:

TGGCTGTCTC ACCCAGTTTA CACCATAGGC GGTTAATGAG AAGCCAGACA 50

CGG 53

(2) INFORMATION FOR SEQ ID NO: 23:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (i i) MOLECULE TYPE: cDNA ( x i ) SEQUENCE DESCRIPTION: SEQ ID NO: 23:

TGCTGGTGTC CTTTCAGCAT TGTCACTCTG GATTTGAGAG CTGAATTATA    50

GTCTGTATTT CCATCACCCC ATATCATTCC AAKCCACTCA AGACC    95

( 2 ) INFORMATION FOR SEQ ID NO: 24:

( i ) SEQUENCE CHARACTERISTICS:
    ( A ) LENGTH: 55 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 24:

CCAGTAGTCC ATAGCATAGA GGGTAGCCGT AACCCTATCT CTTGCACAAT    50

AATAG    55

( 2 ) INFORMATION FOR SEQ ID NO: 25:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 25:

TCTGCTTGGT ACCAGTTTAA ATAATTGCTA ATGCCCTGAC TTGCACTACA    50

GGTGATGGTC    60

( 2 ) INFORMATION FOR SEQ ID NO: 26:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 26:

TCTGCTTGGC ACACCTGAGT GTAAACTTGA TGTGTAGTAG ATCAGCAGCT    50

T    51

( 2 ) INFORMATION FOR SEQ ID NO: 27:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 27:

CCCTTGGCCG AACGTCCGAG GAAGTTTACT ATACTGCTGG CAGTAGTAG    49

( 2 ) INFORMATION FOR SEQ ID NO: 28:

( i ) SEQUENCE CHARACTERISTICS:
    ( A ) LENGTH: 46 base pairs
    ( B ) TYPE: nucleic acid
    ( C ) STRANDEDNESS: single ( D ) TOPOLOGY: linear ( i i ) MOLECULE TYPE: cDNA ( x i ) SEQUENCE DESCRIPTION: SEQ ID NO: 28:

GGGGAAGACC GATGGGCCCT TGGTGGAGGC TGAGGAGACG GTGACC    46

( 2 ) INFORMATION FOR SEQ ID NO: 29:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO: 29:

AGATTTCAGC TGCTCATCAG ATGGCGGGAA GATGAAGACA GATGG    45

( 2 ) INFORMATION FOR SEQ ID NO: 30:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO: 30:

GCCGCTCGAG CCTCACCATG GGATGGAGCT GTATCATCCT CTTCTTGGTA    50

G    51

( 2 ) INFORMATION FOR SEQ ID NO: 31:

( i ) SEQUENCE CHARACTERISTICS:
      ( A ) LENGTH: 94 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO: 31:

GCCGCTCGAG CCTCACCATG GGATGGAGCT GTATCATCCT CTTCTTGGTA    50

GCAACAGCTA CAGGTGTCCA CTCCGACATC CAGATGACCC AGAG    94

( 2 ) INFORMATION FOR SEQ ID NO: 32:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO: 32:

GCGTGACAAG GGCCCATCGG TCTTCCCCCT GGCACCCTC    39

( 2 ) INFORMATION FOR SEQ ID NO: 33:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO: 33:

GCGTGACAAG AATTCTCATT TACCCGGAGA CAGGGAGAGG CTCTT 45

( 2 ) INFORMATION FOR SEQ ID NO: 34:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 34:

```
Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ile Lys Tyr
                20                  25                  30
Leu Asn Trp Tyr Gln Gln Thr Pro Gly Lys Ala Pro Lys Leu Leu Ile
            35                  40                  45
Tyr Glu Ala Ser Asn Leu Gln Ala Gly Val Pro Ser Arg Phe Ser Gly
    50                  55                  60
Ser Gly Ser Gly Thr Asp Tyr Thr Phe Thr Ile Ser Ser Leu Gln Pro
65                  70                  75                  80
Glu Asp Ile Ala Thr Tyr Tyr Cys Gln Gln Tyr Gln Ser Leu Pro Tyr
                85                  90                  95
Thr Phe Gly Gln Gly Thr Lys Leu Gln Ile Thr
                100                 105
```

( 2 ) INFORMATION FOR SEQ ID NO: 35:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 35:

```
Asp Ile Gln Met Thr Gln Thr Thr Ser Ser Leu Ser Ala Ser Leu Gly
1               5                   10                  15
Asp Arg Val Thr Ile Ser Cys Ser Ala Ser Gln Gly Ile Ser Asn Tyr
                20                  25                  30
Leu Asn Trp Tyr Gln Gln Lys Pro Asp Gly Thr Val Lys Leu Leu Ile
            35                  40                  45
Tyr Tyr Thr Ser Ser Leu His Ser Gly Val Pro Ser Arg Phe Ser Gly
    50                  55                  60
Ser Gly Ser Gly Thr Asp Tyr Ser Leu Thr Ile Ser Asn Leu Glu Pro
65                  70                  75                  80
Glu Asp Ile Ala Thr Tyr Tyr Cys Gln Gln Tyr Ser Lys Leu Pro Arg
                85                  90                  95
Thr Phe Gly Gly Gly Thr Lys Val Glu Ile Lys
                100                 105
```

( 2 ) INFORMATION FOR SEQ ID NO: 36:

( i ) SEQUENCE CHARACTERISTICS:
        ( A ) LENGTH: 107 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 36:

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |
| Asp | Arg | Val | Thr | Ile | Thr | Cys | Arg | Ala | Ser | Gln | Ser | Ile | Ser | Asn | Tyr |
| | | | 20 | | | | | 25 | | | | | 30 | | |
| Leu | Asn | Trp | Tyr | Gln | Gln | Lys | Pro | Gly | Lys | Ala | Pro | Lys | Leu | Leu | Ile |
| | | | 35 | | | | 40 | | | | | 45 | | | |
| Tyr | Ala | Ala | Ser | Ser | Leu | Gln | Ser | Gly | Val | Thr | Ser | Arg | Phe | Ser | Gly |
| 50 | | | | | 55 | | | | | | 60 | | | | |
| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |
| Glu | Asp | Ser | Ala | Thr | Tyr | Tyr | Cys | Gln | Gln | Ser | Tyr | Ser | Thr | Leu | Ile |
| | | | | 85 | | | | | 90 | | | | | 95 | |
| Thr | Phe | Gly | Gln | Gly | Thr | Arg | Leu | Glu | Ile | Lys | | | | | |
| | | | 100 | | | | | 105 | | | | | | | |

( 2 ) INFORMATION FOR SEQ ID NO: 37:

( i ) SEQUENCE CHARACTERISTICS:
( A ) LENGTH: 117 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 37:

| Gln | Val | Gln | Leu | Glu | Gln | Ser | Gly | Pro | Gly | Leu | Val | Arg | Pro | Ser | Gln |
|---|---|---|---|---|---|---|---|---|---|---|---|---|---|---|---|
| 1 | | | | 5 | | | | | 10 | | | | | 15 | |
| Thr | Leu | Ser | Leu | Thr | Cys | Thr | Val | Ser | Gly | Ser | Thr | Phe | Ser | Asn | Asp |
| | | | 20 | | | | | 25 | | | | | 30 | | |
| Tyr | Tyr | Thr | Trp | Val | Arg | Gln | Pro | Pro | Gly | Arg | Gly | Leu | Glu | Trp | Ile |
| | | | 35 | | | | | 40 | | | | | 45 | | |
| Gly | Tyr | Val | Phe | Tyr | His | Gly | Thr | Ser | Asp | Asp | Thr | Thr | Pro | Leu | Arg |
| | 50 | | | | | 55 | | | | | 60 | | | | |
| Ser | Arg | Val | Thr | Met | Leu | Val | Asp | Thr | Ser | Lys | Asn | Gln | Lys | Ser | Leu |
| 65 | | | | | 70 | | | | | 75 | | | | | 80 |
| Arg | Leu | Ser | Ser | Val | Thr | Ala | Ala | Asp | Thr | Ala | Val | Tyr | Tyr | Cys | Ala |
| | | | | 85 | | | | | 90 | | | | | 95 | |
| Arg | Asn | Leu | Ile | Ala | Gly | Cys | Ile | Asp | Val | Trp | Gly | Gln | Gly | Ser | Leu |
| | | | 100 | | | | | 105 | | | | | 110 | | |
| Val | Thr | Val | Ser | Ser | | | | | | | | | | | |
| | | | 115 | | | | | | | | | | | | |

( 2 ) INFORMATION FOR SEQ ID NO: 38:

( i ) SEQUENCE CHARACTERISTICS:
( A ) LENGTH: 120 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 38:

Gln  Val  Gln  Leu  Lys  Glu  Ser  Gly  Pro  Gly  Leu  Val  Ala  Pro  Ser  Gln

-continued

```
         1                    5                        10                       15
Ser    Leu    Ser    Ile    Thr    Cys    Thr    Val    Ser    Gly    Phe    Ser    Leu    Thr    Ala    Tyr
                             20                          25                          30

Gly    Val    Asn    Trp    Val    Arg    Gln    Pro    Pro    Gly    Lys    Gly    Leu    Glu    Trp    Leu
                35                          40                          45

Gly    Met    Ile    Trp    Gly    Asp    Gly    Asn    Thr    Asp    Tyr    Asn    Ser    Ala    Leu    Lys
                50                          55                          60

Ser    Arg    Leu    Ser    Ile    Ser    Lys    Asp    Asn    Ser    Lys    Ser    Gln    Val    Phe    Leu
65                                  70                          75                                  80

Lys    Met    Asn    Ser    Leu    Gln    Thr    Asp    Thr    Ala    Arg    Tyr    Tyr    Cys    Ala
                      85                          90                                  95

Arg    Asp    Arg    Val    Thr    Ala    Thr    Leu    Tyr    Ala    Met    Asp    Tyr    Trp    Gly    Gln
                      100                         105                         110

Gly    Thr    Ser    Val    Thr    Val    Ser    Ser
                      115                         120
```

( 2 ) INFORMATION FOR SEQ ID NO: 39:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 39:

```
Gln    Val    Lys    Leu    Val    Gln    Ala    Gly    Gly    Val    Val    Gln    Pro    Gly    Arg
1                            5                           10                          15

Ser    Leu    Arg    Leu    Ser    Cys    Ile    Ala    Ser    Gly    Phe    Thr    Phe    Ser    Asn    Tyr
                      20                          25                          30

Gly    Met    His    Trp    Val    Arg    Gln    Ala    Pro    Gly    Lys    Gly    Leu    Glu    Trp    Val
                      35                          40                          45

Ala    Val    Ile    Trp    Tyr    Asn    Gly    Ser    Arg    Thr    Tyr    Tyr    Gly    Asp    Ser    Val
                      50                          55                          60

Lys    Gly    Arg    Phe    Thr    Ile    Ser    Arg    Asp    Asn    Ser    Lys    Arg    Thr    Leu    Tyr
65                                  70                          75                                  80

Met    Glx    Met    Asn    Ser    Leu    Arg    Thr    Glu    Asp    Thr    Ala    Val    Tyr    Tyr    Cys
                      85                          90                                  95

Ala    Arg    Asp    Pro    Asp    Ile    Leu    Thr    Ala    Phe    Ser    Phe    Asp    Tyr    Trp    Gly
                      100                         105                         110

Gln    Gly    Val    Leu    Val    Thr    Val    Ser
                      115                         120
```

( 2 ) INFORMATION FOR SEQ ID NO: 40:

( i ) SEQUENCE CHARACTERISTICS:
        ( A ) LENGTH: 170 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 40:

```
Thr    Thr    Arg    Ala    Pro    Arg    Ser    Ser    His    Ser    Val    Ile    Ser    Thr    Glu    His
1                            5                           10                          15

Arg    Pro    Leu    Thr    Met    Asp    Ser    Arg    Leu    Asn    Leu    Val    Phe    Leu    Val    Leu
                      20                          25                          30

Ile    Leu    Lys    Gly    Val    Gln    Cys    Asp    Val    Gln    Leu    Val    Glu    Ser    Gly    Gly
```

|  |  |  | 35 |  |  |  | 40 |  |  |  | 45 |  |  |  |
|---|---|---|---|---|---|---|---|---|---|---|---|---|---|---|
| Gly | Leu 50 | Val | Gln | Pro | Gly | Gly 55 | Ser | Arg | Lys | Leu | Ser 60 | Cys | Ala | Ala | Ser |
| Gly 65 | Phe | Thr | Phe | Ser | Asn 70 | Phe | Gly | Met | His | Trp 75 | Val | Arg | Gln | Ala | Pro 80 |
| Asp | Lys | Gly | Leu | Glu 85 | Trp | Val | Ala | Tyr | Ile 90 | Ser | Ser | Gly | Ser | Ser 95 | Thr |
| Ile | Tyr | Tyr | Ala 100 | Asp | Thr | Leu | Lys | Gly 105 | Arg | Phe | Thr | Ile | Ser 110 | Arg | Asp |
| Asn | Pro | Lys 115 | Asn | Thr | Leu | Phe | Leu 120 | Gln | Met | Thr | Ser | Leu 125 | Arg | Ser | Glu |
| Asp | Thr 130 | Ala | Met | Tyr | Tyr | Cys 135 | Ala | Arg | Arg | Gly | Glu 140 | Gly | Ala | Met | Asp |
| Tyr 145 | Trp | Gly | Gln | Gly | Thr 150 | Ser | Val | Thr | Val | Ser 155 | Ser | Ala | Lys | Thr | Thr 160 |
| Pro | Pro | Ser | Val | Tyr 165 | Pro | Leu | Ala | Pro | Gly 170 | | | | | | |

( 2 ) INFORMATION FOR SEQ ID NO: 41:

( i ) SEQUENCE CHARACTERISTICS:
        ( A ) LENGTH: 153 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 41:

| Ile 1 | Ser | Gln | Gly | Thr 5 | Lys | Phe | Lys | Tyr | Thr 10 | Met | Asp | Phe | Gln | Val 15 | Gln |
|---|---|---|---|---|---|---|---|---|---|---|---|---|---|---|---|
| Ile | Phe | Ser | Phe 20 | Leu | Leu | Ile | Ser | Ile 25 | Ser | Val | Val | Met | Ser 30 | Arg | Gly |
| Glu | Asn | Val 35 | Leu | Thr | Gln | Ser | Pro 40 | Ala | Ile | Met | Ser | Ala 45 | Ser | Leu | Gly |
| Glu | Lys 50 | Val | Thr | Met | Ser | Cys 55 | Arg | Ala | Ser | Ser | Ser 60 | Val | Asn | Tyr | Ile |
| Tyr 65 | Trp | Tyr | Gln | Gln | Lys 70 | Ser | Asp | Ala | Ser | Pro 75 | Lys | Leu | Trp | Ile | Tyr 80 |
| Tyr | Thr | Ser | Asn | Leu 85 | Ala | Pro | Gly | Val | Pro 90 | Thr | Arg | Phe | Ser | Gly 95 | Ser |
| Gly | Ser | Gly | Asn 100 | Ser | Tyr | Ser | Leu | Thr 105 | Ile | Ser | Ser | Met | Glu 110 | Gly | Glu |
| Asp | Ala | Ala 115 | Thr | Tyr | Tyr | Cys | Gln 120 | Gln | Phe | Thr | Ser | Ser 125 | Pro | Phe | Thr |
| Phe | Gly 130 | Ser | Gly | Thr | Lys | Leu 135 | Glu | Ile | Lys | Arg | Ala 140 | Asp | Ala | Ala | Pro |
| Thr 145 | Val | Ser | Ile | Phe | Pro 150 | Pro | Ser | Ser | | | | | | | |

( 2 ) INFORMATION FOR SEQ ID NO: 42:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 42:

| Asp | Val | Gln | Leu | Val | Glu | Xaa | Gly | Gly | Gly | Leu | Val | Gln | Pro | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

( 2 ) INFORMATION FOR SEQ ID NO: 43:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 43:

| Glu | Asn | Val | Leu | Thr | Gln |
|-----|-----|-----|-----|-----|-----|
| 1   |     |     |     | 5   |     |

( 2 ) INFORMATION FOR SEQ ID NO: 44:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 44:

| Glu | Val | Gln | Leu | Val | Glu | Ser | Gly | Gly | Gly | Val | Val | Gln | Pro | Gly | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Arg | Leu | Ser | Cys | Ala | Ala | Ser | Gly | Phe | Thr | Phe | Ser | Asn | Phe |
|     |     |     |     | 20  |     |     |     |     | 25  |     |     |     |     | 30  |     |
| Gly | Met | His | Trp | Val | Arg | Gln | Ala | Pro | Gly | Lys | Gly | Leu | Glu | Trp | Val |
|     |     |     |     | 35  |     |     |     |     | 40  |     |     |     |     | 45  |     |
| Ala | Tyr | Ile | Ser | Ser | Gly | Ser | Ser | Thr | Ile | Tyr | Tyr | Ala | Asp | Thr | Leu |
|     |     |     |     | 50  |     |     |     |     | 55  |     |     |     |     | 60  |     |
| Lys | Gly | Arg | Phe | Thr | Ile | Ser | Arg | Asp | Asn | Ser | Lys | Asn | Thr | Leu | Phe |
| 65  |     |     |     |     |     | 70  |     |     |     |     |     | 75  |     |     | 80  |
| Leu | Gln | Met | Asp | Ser | Leu | Arg | Pro | Glu | Asp | Thr | Gly | Val | Tyr | Phe | Cys |
|     |     |     |     | 85  |     |     |     |     | 90  |     |     |     |     | 95  |     |
| Ala | Arg | Arg | Gly | Glu | Gly | Ala | Met | Asp | Tyr | Trp | Gly | Gln | Gly | Thr | Pro |
|     |     |     |     | 100 |     |     |     |     | 105 |     |     |     |     | 110 |     |
| Val | Thr | Val | Ser | Ser |
|-----|-----|-----|-----|-----|
|     |     |     | 115 |     |

( 2 ) INFORMATION FOR SEQ ID NO: 45:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 45:

| Glu | Val | Gln | Leu | Val | Glu | Ser | Gly | Gly | Gly | Val | Val | Gln | Pro | Gly | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Arg | Leu | Ser | Cys | Ser | Ser | Ser | Gly | Phe | Thr | Phe | Ser | Asn | Phe |
|     |     |     |     | 20  |     |     |     |     | 25  |     |     |     |     | 30  |     |
| Gly | Met | His | Trp | Val | Arg | Gln | Ala | Pro | Gly | Lys | Gly | Leu | Glu | Trp | Val |
|     |     |     |     | 35  |     |     |     |     | 40  |     |     |     |     | 45  |     |

Ala Tyr Ile Ser Ser Gly Ser Ser Thr Ile Tyr Tyr Ala Asp Thr Leu
        50                  55                      60

Lys Gly Arg Phe Thr Ile Ser Arg Asp Asn Pro Lys Asn Thr Leu Phe
65                      70                  75                      80

Leu Gln Met Asp Ser Leu Arg Pro Glu Asp Thr Gly Val Tyr Phe Cys
                85                      90                      95

Ala Arg Arg Gly Glu Gly Ala Met Asp Tyr Trp Gly Gln Gly Thr Pro
                100                     105                     110

Val Thr Val Ser Ser
            115

(2) INFORMATION FOR SEQ ID NO: 46:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 46:

Glu Val Gln Leu Val Glu Ser Gly Gly Val Val Gln Pro Gly Arg
1               5                   10                  15

Ser Leu Arg Leu Ser Cys Ser Ser Gly Phe Thr Phe Ser Asn Phe
            20                  25                      30

Gly Met His Trp Val Arg Gln Ala Pro Gly Lys Gly Leu Glu Trp Val
        35                      40                  45

Ala Tyr Ile Ser Ser Gly Ser Ser Thr Ile Tyr Tyr Ala Asp Thr Leu
        50                  55                      60

Lys Gly Arg Phe Thr Ile Ser Arg Asp Asn Ser Lys Asn Thr Leu Phe
65                      70                  75                      80

Leu Gln Met Asp Ser Leu Arg Pro Glu Asp Thr Ala Met Tyr Tyr Cys
                85                      90                      95

Ala Arg Arg Gly Glu Gly Ala Met Asp Tyr Trp Gly Gln Gly Thr Pro
                100                     105                     110

Val Thr Val Ser Ser
            115

(2) INFORMATION FOR SEQ ID NO: 47:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 47:

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                      30

Leu Asn Trp Tyr Gln Gln Thr Pro Gly Lys Ala Pro Lys Leu Leu Ile
        35                      40                  45

Tyr Tyr Glu Ala Ser Asn Leu Gln Ala Gly Val Pro Ser Arg Phe Ser
        50                  55                      60

Gly Ser Gly Ser Gly Thr Asp Tyr Thr Phe Thr Ile Ser Ser Leu Gln
65                      70                  75                      80

Pro Glu Asp Ile Ala Thr Tyr Tyr Cys Gln Tyr Gln Ser Leu Pro Tyr
                85                  90                  95

Thr Phe Gly Gln Gly Thr Lys Leu Gln Ile Thr
                100             105

( 2 ) INFORMATION FOR SEQ ID NO: 48:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 48:

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Val Asn Tyr Ile
                20                  25                  30

Tyr Trp Tyr Gln Gln Lys Ser Asp Ala Ser Pro Lys Leu Trp Ile Tyr
                35                  40                  45

Tyr Thr Ser Asn Leu Ala Pro Gly Val Pro Thr Arg Phe Ser Gly Ser
        50                  55                  60

Gly Ser Gly Asn Ser Tyr Ser Leu Tyr Ile Ser Ser Met Glu Gly Glu
65                  70                  75                  80

Asp Ala Ala Thr Tyr Tyr Cys Gln Gln Phe Thr Ser Ser Pro Phe Thr
                85                  90                  95

Phe Gly Ser Gly Thr Lys Leu Glu Ile Lys
                100             105

( 2 ) INFORMATION FOR SEQ ID NO: 49:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 49:

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Ala Pro Arg Leu Leu Ile
                35                  40                  45

Tyr Gly Ala Ser Ser Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Asp Phe Ala Val Tyr Tyr Cys Gln Gln Tyr Gly Ser Ser Pro Trp Phe
                85                  90                  95

Thr Phe Gly Gln Gly Thr Lys Val Glu Ile Lys
                100             105

( 2 ) INFORMATION FOR SEQ ID NO: 50:

( i ) SEQUENCE CHARACTERISTICS:
        ( A ) LENGTH: 127 amino acids
        ( B ) TYPE: amino acid (C) STRANDEDNESS: single
(D) TOPOLOGY: linear (i i) MOLECULE TYPE: protein (x i) SEQUENCE DESCRIPTION: SEQ ID NO: 50:

| | | | | | | | | | | | | | | |
|---|---|---|---|---|---|---|---|---|---|---|---|---|---|---|
| Gln | Val | Gln | Leu | Val | Glu | Ser | Gly | Gly | Val | Val | Gln | Pro | Gly | Arg |
| 1 | | | | 5 | | | | | 10 | | | | | 15 |
| Ser | Leu | Arg | Leu | Ser | Cys | Ser | Ser | Gly | Phe | Ile | Phe | Ser | Ser | Tyr |
| | | | 20 | | | | | 25 | | | | | 30 | |
| Ala | Met | Tyr | Trp | Val | Arg | Gln | Ala | Pro | Asp | Lys | Gly | Leu | Glu | Trp | Val |
| | | 35 | | | | | 40 | | | | | 45 | | |
| Ala | Tyr | Ile | Ile | Trp | Asp | Asp | Gly | Ser | Asp | Gln | His | Tyr | Ala | Asp | Ser |
| | | 50 | | | | 55 | | | | | 60 | | | |
| Val | Lys | Gly | Arg | Phe | Thr | Ile | Ser | Arg | Asp | Asn | Ser | Lys | Asn | Thr | Leu |
| 65 | | | | | 70 | | | | | 75 | | | | | 80 |
| Phe | Leu | Gln | Met | Asp | Ser | Leu | Arg | Pro | Glu | Asp | Thr | Gly | Val | Tyr | Phe |
| | | | | 85 | | | | | 90 | | | | | 95 | |
| Cys | Ala | Arg | Asp | Gly | Gly | His | Gly | Phe | Cys | Ser | Ser | Ala | Ser | Cys | Phe |
| | | | 100 | | | | | 105 | | | | | 110 | | |
| Gly | Pro | Asp | Tyr | Trp | Gly | Gln | Gly | Thr | Pro | Val | Thr | Val | Ser | Ser |
| | | 115 | | | | | 120 | | | | | 125 | | |

(2) INFORMATION FOR SEQ ID NO: 51:

(i) SEQUENCE CHARACTERISTICS:
 (A) LENGTH: 117 amino acids
 (B) TYPE: amino acid
 (C) STRANDEDNESS: single
 (D) TOPOLOGY: linear (i i) MOLECULE TYPE: protein (x i) SEQUENCE DESCRIPTION: SEQ ID NO: 51:

| | | | | | | | | | | | | | | |
|---|---|---|---|---|---|---|---|---|---|---|---|---|---|---|
| Asp | Val | Gln | Leu | Val | Glu | Ser | Gly | Gly | Leu | Val | Gln | Pro | Gly | Gly |
| 1 | | | | 5 | | | | | 10 | | | | | 15 |
| Ser | Arg | Lys | Leu | Ser | Cys | Ala | Ala | Ser | Gly | Phe | Thr | Phe | Ser | Asn | Phe |
| | | | 20 | | | | | 25 | | | | | 30 | | |
| Gly | Met | His | Trp | Val | Arg | Gln | Ala | Pro | Asp | Lys | Gly | Leu | Glu | Trp | Val |
| | | 35 | | | | | 40 | | | | | 45 | | | |
| Ala | Tyr | Ile | Ser | Ser | Gly | Ser | Ser | Thr | Ile | Tyr | Tyr | Ala | Asp | Thr | Leu |
| | | 50 | | | | 55 | | | | | 60 | | | | |
| Lys | Gly | Arg | Phe | Thr | Ile | Ser | Arg | Asp | Asn | Pro | Lys | Asn | Thr | Leu | Phe |
| 65 | | | | | 70 | | | | | 75 | | | | | 80 |
| Leu | Gln | Met | Thr | Ser | Leu | Arg | Ser | Glu | Asp | Thr | Ala | Met | Tyr | Tyr | Cys |
| | | | | 85 | | | | | 90 | | | | | 95 | |
| Ala | Arg | Arg | Gly | Glu | Gly | Ala | Met | Asp | Tyr | Trp | Gly | Gln | Gly | Thr | Ser |
| | | | 100 | | | | | 105 | | | | | 110 | | |
| Val | Thr | Val | Ser | Ser |
| | | 115 | | |

(2) INFORMATION FOR SEQ ID NO: 52:

(i) SEQUENCE CHARACTERISTICS:
 (A) LENGTH: 114 amino acids
 (B) TYPE: amino acid
 (C) STRANDEDNESS: single
 (D) TOPOLOGY: linear (i i) MOLECULE TYPE: protein (x i) SEQUENCE DESCRIPTION: SEQ ID NO: 52:

| | | | | | | | | | | | | | | | |
|---|---|---|---|---|---|---|---|---|---|---|---|---|---|---|---|
| Gln | Val | Gln | Leu | Val | Asp | Ser | Gly | Gly | Leu | Val | Glu | Pro | Gly | Gly |
| 1 | | | | 5 | | | | 10 | | | | | 15 | |
| Ser | Leu | Arg | Leu | Ser | Cys | Ser | Ala | Ser | Gly | Phe | Thr | Phe | Ser | Ala | Asn |
| | | | 20 | | | | 25 | | | | | 30 | | |
| Asp | Met | Asn | Trp | Val | Arg | Gln | Ala | Pro | Gly | Lys | Gly | Leu | Glu | Trp | Leu |
| | | 35 | | | | | 40 | | | | | 45 | | | |
| Ser | Phe | Ile | Gly | Gly | Ser | Gly | Ser | Thr | Ile | Tyr | Tyr | Ala | Asp | Ser | Val |
| | 50 | | | | | 55 | | | | | 60 | | | | |
| Lys | Gly | Arg | Phe | Thr | Ile | Ser | Arg | Asn | Asx | Ser | Lys | Asn | Ser | Leu | Tyr |
| 65 | | | | | 70 | | | | | 75 | | | | | 80 |
| Leu | Gln | Met | Ser | Ser | Leu | Arg | Ala | Glu | Asp | Thr | Ala | Val | Tyr | Tyr | Cys |
| | | | | 85 | | | | | 90 | | | | | 95 | |
| Ala | Arg | Gly | Trp | Leu | Leu | Asn | Trp | Gly | Gln | Gly | Thr | Leu | Val | Thr | Val |
| | | | 100 | | | | | 105 | | | | | 110 | | |
| Ser | Ser | | | | | | | | | | | | | | |

HUMANIZED ANTIBODIES AND USES THEREOF

The present invention relates to humanized antibodies and binding proteins thereof, capable of binding to T cells exhibiting particular variable beta chains, and particularly those subpopulations expressing human Vβ 5.2 and/or 5.3, and Vβ 8.1. The present invention also relates to the preparation of such antibodies, to pharmaceutical compositions containing them, and therapeutic utilization of the antibodies, specifically in autoimmune diseases.

T cells play a pivotal role in the differentiation and regulation of effector mechanisms within the immune system (Paul et al., (1987) Science 195:1293–1300). The co-recognition of antigen and major histocompatibility molecules by a T cell must be specific and precisely regulated, since improper immune regulation fosters autoimmunity. Several laboratories have studied diseases in which there appears to be improper immune regulation, such as autoimmunity, and some forms of immunodeficiency, and have implicated T cells in the pathogenesis of such diseases.

Several situations exist where there have been reported a clonal or oligoclonal expansion of a particular T cell receptor composition. The most obvious examples are in conditions of malignancy which have resulted in a T cell leukemia or lymphoma. In situations of T cell leukemias or lymphomas, the T cell receptor acts as a unique tumor marker since the T cell receptor is stably rearranged and presented on the surface of the cell. Another situation where a particular T cell receptor composition is implicated is in the recipient of an organ graft whose T lymphocytes have T cell receptors making them aggressive against the MHC molecules of the donor individual, as for instance the donor of a bone marrow graft.

More importantly, several groups have reported selective T cell antigen receptor V region gene usage in certain autoimmune situations. For instance, Grunwald et al. have noted a preferential expression of the Vα 2.3 gene product in CD4+ T cells in the broncheoalveolar lavage when compared to peripheral blood lymphocytes of patients with Sarcoidosis (Grunwald et al., (1992) Eur. J. Immunol. 22:129). In Kawasaki disease, the preferential expansion of Vβ 2 and Vβ 8 T cells was noted at the onset of disease (Abe et al., (1992) Proc. Natl. Acad. Sci. USA 89:4066).

Rheumatoid arthritis has also been extensively studied in this regard. Several investigators have noted preferential expansion of subsets of T cells, as for instance: DerSimonian et al., (1993) J. Exp. Med. 177:1623 (preferential expansion of Vα 12.1 bearing T cells in CD8+ peripheral blood T lymphocytes); Stamenkovic et al., (1988) Proc. Natl. Acad. Sci. USA 85:1179 (synovial membrane-infiltrating T cells grown in IL2 were oligoclonal by southern blot analysis); Paliard et al., (1991) Science 253:34 (hypothesized that a Superantigen activated Vβ 14+ T cells, including autoreactive T cells which expand clonally and migrate to the synovial fluid of rheumatoid arthritis patients); Howell et al., (1991) Proc. Natl. Acad. Sci. USA 88:10921 (noted in particular Vβ 3, 14, and 17 T cell V region gene usage in IL 2R+ cells from synovial fluid of rheumatoid arthritis patients); Uematsu et al., Proc. Natl. Acad. Sci. USA 88:8534 (showed oligoclonal T cell V region gene usage in synovial fluid T cells of a single RA individual); and International Patent Application No. WO90/06758 (implicating Vβ 3, 9, and 10 in RA).

Inflammatory bowel disease has also been extensively studied. Several groups have noted expanded T cell populations or preferential T cell receptor V region gene usage as for instance: Posnett et al., (1990) J. Clin. Invest. 85:1770; Spencer et al., (1991) J. Clin. Pathol. 44:915; Trejjdosiewicz et al., (1991) Clin. Exp. Immunol. 84:440; and Van Kerckhove et al., (1992) J. Exp. Med. 175:57. Still others have reported preferential T cell V gene usage in Mycobacterium leprae (van Shooten et al., (1992) Proc. Natl. Acad. Sci. USA 89:11244; Wang et al., (1993) Proc. Natl. Acad. Sci. USA 90:188.

In humans, expansion of Vβ 8.1 T cells in inflammatory tissue has been found in association with several autoimmune diseases, including Crohn's Disease (Posnett et al., (1990) J. Clin. Invest. 85:1770–1776), Kawasaki Disease (Abe et al., (1992) Proc. Natl. Acad. Sci. USA 89:4066–4070 and Abe et al., (1993) J. Exp. Med. 177:791–796) and rheumatoid arthritis (Brennan et al., (1988) Clin. Exp. Immunol. 73:417–423).

Multiple Sclerosis (MS) is another autoimmune disease that has been intensively studied. MS is an immune mediated disease characterized by central nervous system mononuclear cell infiltration and demyelination. Although the pathogenesis of MS is unknown, both genetic and environmental factors have been implicated in the disease process. Major elements of the genetic predisposition include an association of disease with particular class II major histocompatibility complex (MHC) haplotypes, in particular HLA-DR21 and DQW1 (Terasaid et al., (1976) Science 1933:1245–1247; Ho et al., (1982) Immunogenetics 15:509–517; Spielman et al., (1982) Epidemiol. Rev. 4:45–65; Francis et al., (1986) Lancet 1:211; Elian et al., (1987) Disease Markers 5:89–99; Urban et al., (1988) Cell 54:577–592, Vandenbark et al., (1989) Nature 341:541–544: Howell et al., (1989) Science 246:668–670).

It has been shown that T cells isolated from the cerebrospinal fluid of patients suffering from MS utilize a limited set of V region genes. The demonstration of in vivo activated myelin basic protein specific T cells in MS patients implicates MBP reactive T cells in the pathogenesis of the disease (Wucherpfennig et al., (1990) Science 248:1016–1019). When the TCR Vβ usage of MBP reactive T cell lines is determined via polymerase chain reaction (PCR) amplification of cDNA with T cell receptor Vβ primers, preferential usage of a limited number of Vβ genes has been found (Wucherpfennig et al., (1990) (supra)-Vβ 17 and to a lesser extent Vβ 12 are frequently used in the recognition of the immunodominant region of the human autoantigen MBP); Oksenberg et al., (1993) Nature 362:68. The results of some studies also imply that there is a limited T cell receptor V α gene expression in MS brain lesions (Oksenberg et al., (1990) Nature 345:344–346). T cell repertoire analysis using quantitative PCR and monoclonal antibody (mAb) staining has shown that Vβ 5.2 and/or 5.3 are predominantly utilized by the myelin basic protein (MBP) specific T cells isolated from MS patients compared with control (Oksenberg et al., (1993) (supra) (rearranged Vβ 5.2 genes were detected in the brains of patients with a certain HLA phenotype) and Kotzin et al. (1991) Proc. Natl. Acad. Sci. USA 88:9196 (a bias for use of the β chain variable region 5.2 and to a lesser extent Vβ 6.1 was seen among MBP specific clones from patients with MS).

Currently, no effective treatment for MS is known. (*Harrison's Principles of Internal Medicine,* 12th ed. Wilson et al., McGraw Hill, Inc. 1991). Therapeutic efforts are directed toward amelioration of the acute episode, prevention of relapses or progression of the disease, and relief of symptoms.

However, expression of the mouse Vβ 8.2 variable region gene has been found to correlate with experimental allergic encephalomyelitis (EAE), a mouse model of human MS. It has been demonstrated that treatment with mouse Vβ 8.2 specific mAb can both prevent and reduce the disease (Acha-Orbea et al., (1988) Cell 54:263 and Urban et al., (1988) Cell 54:577). Thus, there is a great need to develop an antibody or "antibody-like" molecule, suitable for treatment of this disease.

Antibodies typically comprise two heavy chains linked together by disulfide bonds and a light chain associated with the N-terminal end of each heavy chain. Each heavy chain has at its N-terminal end a variable domain followed by a constant domain at its other end. Each light chain also has at its N-terminal end a variable domain followed by a constant domain. The variable domains of each pair of light and heavy chains form the antigen binding site. The variable domains on the light and heavy chains have the same general structure and each domain comprises a framework of four regions, whose sequences are relatively conserved, connected by three complementarity determining regions (CDRs). The four framework regions adopt somewhat of a beta-sheet conformation and the CDRs form loops connecting the beta-sheet construction. The CDRs are held in close proximity by the framework regions and contribute to the formation of the antigen binding site. CDRs and framework regions of antibodies may be determined by reference to the Kabat numbering system (Kabat et al., (1987) "Sequences of Proteins of Immunological Interest", US Dept. of Health and Human Services, US Government Printing Office) in conjunction with x-ray crystallography, as set forth in WO91/09967.

In order to produce an antibody which can target a specific antigen, the procedure of Kohler and Milstein (Kohler et al., (1976) Nature 256:495–497) is usually used. This generally involves immunising a mouse with the antigen, fusing spleen cells from the immunised mouse with mouse myeloma cells and selecting from the hybridomas thus produced one or more hybridomas which secrete a monoclonal antibody specific for the target antigen.

It would be desirable to use such mAbs in therapy. However, such mAbs are essentially of murine origin and are therefore themselves antigenic in humans. If such mAbs are administered repeatedly to a human, the human's immune system mounts a response to the mouse mAb, thus rendering it ineffective.

It has therefore been proposed, originally by Winter and his coworkers (see, for instance, Reichmann et al., (1988) Nature 332:323–327 and Verhoeyen et al., (1988) Science 239:1534–1536) that the CDRs of a mouse mAb should be grafted onto a human framework to produce a CDR-grafted antibody having the binding properties of the donor mouse mAb and the human compatibility of the acceptor human framework.

However, the function of an antibody molecule is dependent on its three dimensional structure, which in turn is dependent on its primary amino acid sequence. Changing the amino acid sequence of an antibody may adversely affect its activity. Likewise, fragments of the antibody may not retain the appropriate three dimensional structure necessary to foster binding activity. Moreover, a change in the DNA sequence coding for the antibody may affect the ability of the cell containing the DNA sequence to express, secrete or assemble the antibody. The exact residues comprising CDRs are difficult to define and do not necessarily correspond to all the residues in the hypervariable regions, as defined by the Kabat numbering system. There are also critical framework residues which are important in positioning the CDRs for interaction with antigen or which are involved in interactions between the heavy and light chains. It may be necessary to alter certain framework residues so that they correspond to the donor residues at certain positions, rendering the CDR-grafted antibody less "human" in character.

There have been published various proposals for identifying the CDR and framework residues which need to be changed to donor residues in order to produce a useful CDR-grafted antibody (see, for instance, Queen et al., WO90/07861; Kurrle et al., EP-A-0 403 156; Adair et al., WO91/09967; Queen et al., WO92/11018; and Bendig et al., WO92/01568). It emerges from these documents that the production of a useful CDR-grafted antibody in any particular case is not straightforward.

Despite the problems which are inherent in attempting to produce a specific CDR-grafted antibody, in a preferred embodiment, the present inventors have succeeded in producing a CDR-grafted antibody based on human framework regions and having an antigen binding site specific for variable beta chain regions peculiar to certain subpopulations of T cells. Surprisingly, the humanized antibodies of the invention demonstrate as good or better binding affinity to target T cells when compared to their murine prototypes. The currently claimed antibodies or parts thereof offer the further advantage of being less immunogenic than their murine prototypes, thus diminishing adverse patient reactions when used in therapy.

SUMMARY OF THE INVENTION

The present invention is directed to humanized antibodies having a selective binding specificity for certain T cell subpopulations, which antibodies are highly sensitive in their binding to these subpopulations, and demonstrate specificity and affinity in that binding, comparable with, if not better than, that of the protype mAbs from which a substantial portion of their CDR regions are derived. The present invention is also directed to methods of preparation of such humanized antibodies, utilizing novel cDNA encoding certain hypervariable and framework residues and grafting these into human heavy chain and human light chain frameworks. Further embodiments include pharmaceutical compositions and therapeutic methods of using these antibodies.

In one particularly preferred embodiment, the mouse mAb, 16G8, which recognizes human Vβ 8.1, was humanized by CDR grafting certain CDR and select framework residues from the murine mAb into KOL heavy chain and REI light chain frameworks. The cDNAs encoding humanized heavy (IgG1) and light (K) chains in mammalian cell expression vectors with Neo and DHFR selection markers, respectively, were tranfected into a DHFR- Chinese hamster fibroblast (CHO) cell line followed by selection and amplification. The humanized mAb secreted, designated "TM29", maintains the specificity for human TCR Vβ 8.1 with affinity comparable to that of the prototype mouse mAb (16G8). The antibodies of the invention have demonstrated that humanization of anti-TCR antibodies can be accomplished while maintaining the correct subset specificity and affinity.

Other embodiments of the invention include the use of these humanized antibodies as a therapeutic agent for treatment of human autoimmune disease, and particularly Crohn's disease.

In another particularly preferred embodiment of the present invention, a mouse mAb, TM23, which recognizes human Vβ 5.2 and 5.3, was humanized by CDR grafting into NEWM heavy chain and REI light chain frameworks. The cDNAs encoding humanized heavy (IgG1) and light (K)

chains in mammalian cell expression vectors with Neo and DHFR selection markers, respectively, were transfected into a DHFR- Chinese hamster fibroblast (CHO) cell line followed by selection and amplification. The humanized mAb that was secreted was designated "TM27", and maintains specificity for human TCR Vβ 5.2 and 5.3 with affinity comparable to, if not better than, that of the prototype mouse mAb (TM23). Other embodiments of the invention include the use of TM27 as a therapeutic agent for treatment of human MS.

BRIEF DESCRIPTION OF THE FIGURES

FIG. 1 depicts various variable light chain sequences and heavy chain sequences for TM27 (SEQ ID NO.s 2, 5–9, 35 and 38):

FIG. 2 depicts various variable light chain sequences and heavy chain sequences for TM29 (SEQ ID NO.s 1, 3, 44–46, 48 and 51);

DETAILED DESCRIPTION OF THE INVENTION

Figure 3:
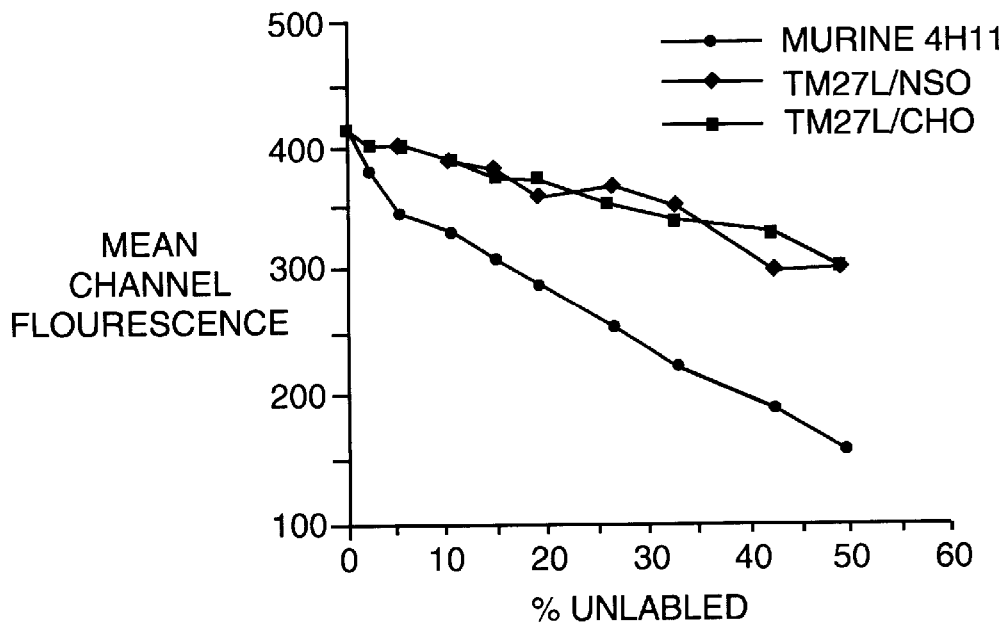
FIG. 3 depicts the results of a competition assay comparing TM27L/NSO and TM27L/CHO with 4H11.

Certain definitions used in the context of the description of the invention are set forth as follows.

In the present application, the term "antibody" is used to describe Igs or any fragments thereof, light chain or heavy chain monomers or dimers, and single chain antibodies, such as a single chain Fvs in which the heavy and light chain variable domains are joined by a peptide linker, whether natural or produced by recombinant DNA technology or otherwise, provided that the antibody includes at least one antigen binding site. The remainder of the antibody need not comprise only Ig-derived protein sequences. For instance, a gene may be constructed in which a DNA sequence encoding part of a human Ig chain is fused to a DNA sequence encoding the amino acid sequence of a polypeptide effector or reporter molecule. Thus "antibody" encompasses hybrid antibodies (see below).

The term "binding protein" as used herein refers to a construct having a particular amino acid sequence derived from an antibody or combination of antibodies, said sequence sterically configured in such a manner as to form at least one antigen binding site.

The abbreviation "mAb" is used to indicate a monoclonal antibody as produced by a hybridoma or derivative cell line.

The term "recombinant antibody" is used to describe an antibody produced by a process involving the use of recombinant DNA technology.

The term "CDR" or "complementarity determining region" refers to those portions of an antibody's heavy chain or light chain variable regions juxtapositioned in three-dimensional space to form an antigen binding surface.

The term "chimeric antibody" is used to describe an antibody in which the variable domains as a whole are derived from an antibody from a first mammalian species and have been fused onto at least one constant domain from an antibody from a different mammalian species.

The term "CDR-grafted" is used to describe an antibody or portion thereof in which the CDRs are substantially derived from an antibody from a first mammalian species, grafted into a variable framework regions substantially derived from a second mammalian species. Certain select amino acids in said framework regions may also be derived from said first mammalian species.

The term "hybrid antibody" is used to describe a protein comprising at least the binding portion of an Ig attached by peptide linkage to at least part of another protein. It will be appreciated that certain skilled workers may also use the word "chimeric" to describe such constructs, but in the present specification such constructs are referred to as hybrid antibodies and the term chimeric antibodies is used in the sense defined above.

The term "humanized antibody" is used to describe an antibody having at least one, and preferably two or three, of its CDRs in one or both of the variable domains derived from an antibody from a first species, it being understood that this may involve certain select framework amino acids in conjunction with certain hypervariable amino acid sequences. The remaining Ig-derived parts of the antibody being derived from one or more different antibodies. The variable domains may be made by use of recombinant DNA technology or by peptide synthesis.

"Expression vector" includes vectors which are capable of expressing DNA sequences contained therein, i.e. the coding sequences are operably linked to other sequences capable of effecting their expression. A useful, but not always necessary (i.e. insect cells), element of an effective expression vector is a marker encoding sequence, i.e. a sequence encoding a vector sequence which results in a phenotypic property (e.g. neomycin resistance, methionine sulfoximine resistance or tryptophan prototrophy) of the cells containing the protein which permits those cells to be readily identified. In sum, "expression vector" is given a functional definition and any DNA sequence which is capable of effecting expression of a specified contained DNA code is included in this term as it is applied to the specified sequence. As at present, such vectors are frequently in the form of plasmids. Thus "plasmid" and "expression vector" are often used interchangeably. However, the invention is intended to include such other forms of expression vectors which serve equivalent functions and which may, from time to time, become known in the art, including retroviruses, adenoviruses, in vitro systems (Baranov et al., (1989) Gene 84:2:463) and the like.

As stated previously, the DNA sequences will be expressed in host cells after the sequences have been operably linked to (i.e. positioned to ensure the functioning of) an expression control sequence. These expression vectors are typically replicable in the host organisms either as episomes or as an integral part of the host chromosomal DNA.

"Recombinant host cells" refers to cells which have been transformed with vectors constructed using recombinant DNA techniques. By virtue of this transformation, the host cell is able to produce the desired product in useful quantities, rather than in lesser amounts, or more commonly, in less than detectable amounts, as one would expect to be produced by the untransformed host. The antibody and binding proteins of the present invention may be produced by a recombinant host cell in quantities useful to carry out additional experimentation or in commercially acceptable quantities, such as about 100 grams or more.

In descriptions of processes for isolation of antibodies or binding proteins thereof from recombinant hosts, the terms "cell" and "cell culture" are used interchangeably to denote the source of antibody unless it is clearly specified otherwise. In other words, recovery from the "cells" may mean either from spun down whole cells, or from the cell culture containing both the medium and the suspended cells, or, additionally, as is possible in the case of myeloma cell lines, from ascites culture.

The humanized antibodies or binding proteins thereof of the present invention have amino acid sequences that comprise all or a portion of its CDRs substantially derived from a monoclonal antibody having a specificity for a select subpopulation of T cells, and particularly the Vβ 8.1 subpopulation or the Vβ 5.2/5.3 subpopulation. In the preferred embodiments, the monoclonal antibody is murine in origin. The framework amino acid sequence of the variable constructs made in accordance with the invention, it being understood that a construct may be a very suitable therapeutic agent even when its binding pattern to target antigen differs from that of the prototype mAb.

In particularly preferred embodiments, the amino acid sequence of the humanized antibody or binding protein thereof comprises all or a portion of a variable light chain selected from the following group:

TM 29 light chain (SEQ ID NO: 1)

| 1 | D I Q M T Q S P S S L S A S V G D R V T I T C R A S S S V N Y I Y W Y Q Q T P G K A P K L L I Y Y T | 50 |
| 51 | S N L A P G V P S R F S G S G S G T D Y T F T I S S L Q P E D I A T Y Y C Q Q F T S S P F T F G Q G | 100 |
| 101 | T K L Q I T | 106 |

TM 27 light chain (SEQ ID NO: 2)

| 1 | D I Q M T Q S P S S L S A S V G D R V T I T C S A S Q G I S N Y L N W Y Q Q T P G K A P K L L I Y Y | 50 |
| 51 | T S S L H S G V P S R F S G S G S G T D Y T F T I S S L Q P E D I A T Y Y C Q Q Y S K L P R T F G Q | 100 |
| 101 | G T K L Q I T | 107 | alone or in any combination with all or a portion of a variable heavy chain selected from the following group:

TM 29 heavy chain (SEQ ID NO: 3)

| 1 | E V Q L V E S G G G V V Q P G R S L R L S C S S S G F T F S N F G M H W V R Q A P G K G L E W V A Y | 50 |
| 51 | I S S G S S T I Y Y A D T L K G R F T I S R D N S K N T L F L Q M D S L R P E D T G V Y F C A R R G | 100 |
| 101 | E G A M D Y W G Q G T P V T V S S | 117 |

TM 27 heavy chain (SEQ ID NO: 4)

| 1 | Q V Q L Q E S G P G L V R P S Q T L S L T C T V S G F S L T A Y G V N W V R Q P P G R G L E W L G M | 50 |
| 51 | I W G D G N T D Y N S A L K S R V T M L K D T S K N Q F S L R L S S V T A A D T A V Y Y C A R D R V | 100 |
| 101 | T A T L Y A M D Y W G Q G S L V T V S S | 120 | domains of the antibodies or portions thereof is substantially human in origin in the preferred embodiments, hence the term "humanized antibody". This "humanization" is believed to be useful in reducing the immunogenicity of the antibody when administered therapeutically to human patients. Preferred for use herein are the NEWM or KOL human framework regions for the heavy chain, and REI human framework regions for the light chain. Certain select framework residues are maintained as murine, rather than human. This is believed necessary to achieve the appropriate three-dimensional structuring of the molecule, and to thereby increase binding specificity and affinity for the specific T cell subset.

Any portion of the humanized antibodies (hence, the broad definition of the term antibody) made in accordance with the present teachings is within the contemplation of the present invention, as long as binding specificity and affinity for select subpopulations of T cells is maintained. Thus, binding proteins derived from said antibodies are clearly within the scope of the invention, as are other fragments that maintain these capabilities, at least to a degree suitable for therapeutic use, as described below.

One skilled in the art may test the binding parameters of various constructs made following the teachings herein through the use of conventional binding assays conducted with specific T cells or T cell receptor proteins exhibiting the select variable region that is targeted. For example, competition binding assays with prototype mAbs, binding to various cell lines, Scatchard analyses and the like may be performed and compared to results obtained with prototype mAbs. Alternatively, one may resort to various animal model systems, such as those described below, or clinical trial studies to assess the therapeutic effectiveness of the Select framework residues in the vicinity of the individual CDRs are important to the support of the three-dimensional conformation of the CDRs (Foote and Winter, (1992) J. Mol. Biol. 224:487–499). Thus, in certain preferred embodiments, modified heavy chains were designed. In the first at residues 66 to 69 inclusive and 73, the murine sequence Leu-Ser-Ile-Ser (66–69) and Asp (73) are substituted for the human counterparts.

In other preferred embodiments, murine residues valine and phenylaline are provided at positions 78 and 79, respectively, or murine arginine is provided at position 92.

FIG. 1 exemplifies these substitutions, showing the CDRs in bold and underlining. These preferred antibody constructs (including binding proteins thereof) bind to Vb 5.2/5.3.

Other preferred antibodies and binding proteins thereof are provided herein by modification of heavy chains at residues 23 and 24. At these positions, the murine counterpart sequence Ala- is substituted. Other constructs demonstrate that residue 75 may be the murine proline residue, or that residues 88, 89 and 91 may be alanine, methionine or tyrosine respectively. These antibody constructs and binding proteins thereof bind Vβ 8.1 T cells and are more fully depicted in FIG. 2.

Particularly preferred for use herein are CDR-grafted antibodies consisting essentially of the TM27 light chain in conjunction with the TM27 heavy chain, wherein residue 48 is either murine leucine or isoleucine. Also particularly preferred are CDR-grafted antibodies consisting essentially of the TM29 light chain in conjunction with the TM29 heavy chain.

The humanized antibodies or binding proteins thereof of the present invention may be produced by a variety of techniques, with expression in transfected cells, such as yeast, insect, CHO or myeloma cells, being preferred. Most preferably, the host cell is a CHO host cell.

To design a CDR-grafted antibody or a binding protein thereof in accordance with the present invention, it is first necessary to ascertain the variable domain sequence of an antibody having the desired binding properties. Suitable source cells for such DNA sequences include avian, mammalian or other vertebrate sources such as chickens, mice, rats and rabbits, and preferably mice. The variable domain sequences ($V_H$ and $V_L$) may be determined from heavy and light chain cDNA, synthesized from the respective mRNA by techniques generally known to the art. The hypervariable regions may then be determined using the Kabat method (supra). The CDRs may be determined by structural analysis using X-ray crystallography or molecular modelling techniques. Composite CDRs may then be constructed containing all the residues corresponding to the hypervariable regions, along with certain select residues from the framework regions. The resulting composite CDRs may then be transferred as the "antigen binding site", while the remainder of the antibody, if it is desired to construct a complete Ig, will include the heavy and light chain constant domains and remaining framework residues. The latter portions may be based on human antibodies of different classes.

Constant domains may be selected to have desired effector functions appropriate to the intended use of the antibody so constructed. For example, human IgG isotypes, $IgG_1$ and $IgG_3$ are effective for complement fixation and cell mediated lysis. For other purposes, other isotypes, such as $IgG_2$ and $IgG_4$, or other classes, such as IgM and IgE, may be more suitable.

For human therapy, it is particularly desirable to use human isotypes, to minimize antiglobulin responses during therapy. Human constant domain DNA sequences, preferably in conjunction with their variable domain framework regions can be prepared in accordance with well-known procedures. An example of this is CAMPATH 1H available from Burroughs Wellcome Ltd.

In accordance with preferred embodiments of the present invention, certain CDR-grafted antibodies are provided which contain select alterations to the human-like framework region (in other words, outside of the CDRs of the variable domains), resulting in a CDR-grafted antibody with satisfactory binding affinity. Such binding affinity is preferably from about $10^{-5}M$ to about $10^{-12}M$ and is more preferably at least about $10^{-8}M$. Most preferably the binding affinity is about equal to or greater than that of the prototype antibody (in preferred instances, this prototype antibody would be murine).

In constructing the CDR-grafted antibodies of the present invention, the $V_H$ and/or $V_L$ gene segments may be altered by mutagenesis. One skilled in the art will also understand that various other nucleotides coding for amino acid residues or sequences contained in the Fc portion or other areas of the antibody may be altered in like manner (see, for example, PCT/US89/00297).

Exemplary techniques include the addition, deletion or nonconservative substitution of a limited number of various nucleotides or the conservative substitution of many nucleotides, provided that the proper reading frame is maintained.

Substitutions, deletions, insertions or any subcombination may be used to arrive at a final construct. Since there are 64 possible codon sequences but only twenty known amino acids, the genetic code is degenerate in the sense that different codons may yield the same amino acid. However, the code is precise for each amino acid. Thus, there is at least one codon for each amino acid, i.e. each codon yields a single amino acid and no other. It will be apparent that, during translation, the proper reading frame must be maintained in order to obtain the proper amino acid sequence in the polypeptide ultimately produced.

Techniques for additions, deletions or substitutions at predetermined amino acid sites having a known sequence are well known. Exemplary techniques include oligonucleotide-mediated site-directed mutagenesis and the PCR.

Oligonucleotide site-directed mutagenesis in essence involves hybridizing an oligonucleotide coding for a desired mutation with a single strand of DNA containing the region to be mutated and using the single strand as a template for extension of the oligonucleotide to produce a strand containing the mutation. This technique, in various forms, is described in Zoller and Smith, (1982) Nuc. Acids Res. 10:6487, Norris et al., (1983) Nuc. Acids Res. 11:5103, Zoller and Smith, (1984) DNA 3:479, Kramer et al., (1982) Nuc. Acids Res. 10:6475.

PCR in essence involves exponentially amplifying DNA in vitro using sequence-specific oligonucleotides. The oligonucleotides can incorporate sequence alterations if desired. The PCR technique is described in Mullis and Foloona, (1987), Meth. Enz. 155:335. Examples of mutagenesis using PCR are described in Higuchi et al., (1988) Nuc. Acids Res. 16:7351, Ho et al., (1989) Gene, 77:51, Ho et al., Engineering Hybridization Restriction Genes without the Use of Restriction Enzymes: Gene Splicing by Overlap Extension; Horton et al., (1989) Gene 77:61.

The nucleotide sequences of the present invention, capable of ultimately expressing the desired antibodies, or binding proteins thereof, can be formed from a variety of different polynucleotides (genomic DNA, cDNA, RNA or synthetic oligonucleotides). At present, it is preferred that the polynucleotide sequence comprises a fusion of cDNA and genomic DNA. The polynucleotide sequence may encode various Ig components (e.g. V, J, D, and C domains). They may be constructed by a variety of different techniques. Joining appropriate genomic and cDNA sequences is presently the most common method of production, but cDNA sequences may also be utilized (see EP-A-0 239 400 and Reichmann et al., (1988) Nature 332:323.)

Certain suitable expression vectors and host cells are described in U.S. Pat. No 4,816,567.

The vectors and methods disclosed herein are suitable for use in host cells over a wide range of prokaryotic and eukaryotic organisms.

In general, of course, prokaryotes are preferred for cloning of DNA sequences for constructing the vectors useful in the invention. For example, various *E. coli* plasmid cloning vectors are particularly useful, such as the Bluescript M13 vectors available from Stratagene, San Diego, Calif.; pUC19c, Genbank Accession #VB0026, pBR322 (described below) and the like. These examples are, of course, intended to be illustrative rather than limiting.

Prokaryotes may also be used for expression. The aforementioned *E. coli* strains, *bacilli* such as *Bacillus subtilis*, and other enterobacteriaceae, such as *Salmonella typhimurium* or Serratia marcescens and various Pseudomonas species may be used.

In general, plasmid vectors containing replicon and control sequences which are derived from species compatible with the host cell are used in connection with these hosts.

The vector ordinarily carries a replication site as well as marking sequences which are capable of providing phenotypic selection in transformed cells. For example, E. coli is typically transformed using one of the many derivatives of pBR322, a plasmid derived from an E. coli species (Bolivar et al., (1977) Gene 2:95.) pBR322 contains genes for ampicillin and tetracycline resistance and thus provides easy means for identifying transformed cells. The pBR322 plasmid, its descendants or other microbial plasmids may also contain, or be modified to contain, promoters which can be used by the microbial organism for the expression of recombinant proteins. Those promoters commonly used in recombinant DNA construction include lactose promoter systems (Chang et al., (1978) Nature 275:615; Itakura et al., (1978) Science 198:1056; Goedell et al., (1979) Nature 281:544) and tryptophan (trp) promoter systems (Goedell et al., (1980) Nuc. Acids Res. 8:4057) and EP-A-0 036 776. While these are the most commonly used, other microbial promoters have been discovered and utilized, and details concerning their nucleotide sequences have been published, enabling a skilled worker to ligate them functionally into plasmid vectors (Siebenlist et al., (1980) Cell 20:269).

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in Saccharomyces, the plasmid YRp7, for example, (Stinchcomb et al., (1979) Nature 282:39; Kingsman et al., (1979) Gene 7:141; Tschemper et al., (1980) Gene 19:157) is commonly used. This plasmid already contains the trpl gene which provides a selection marker for a mutant strain of yeast lacking the ability to grow in tryptophan, for example ATCC No. 44076 or PEP4–1 (Jones, (1977) Genetics 8:85:12). The presence of the trpl lesion as a characteristic of the yeast host cell genome than provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase (Hess et al., (1968) J. Adv. Enzyme Reg. 7:149; Holland et al., (1978) Biochemistry 17:4900.) In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter regions for alcohol dehydrogenase 2, isocytochrome C, acid phosphatase, degradative enzymes associated with nitrogen metabolism and the aforementioned glyceraldehyde-3-phosphate dehydrogenase, an enzyme responsible for maltose and galactose utilization. Any plasmid vector containing a yeast compatible promoter, origin of replication and termination sequences is suitable.

In addition to microorganisms, cultures of cells derived from multicellular organisms may also be used as hosts. In principle, any such cell culture is workable, whether from a vertebrate or an invertebrate organism. However, to date, interest has been greatest in vertebrate cells, and propagation of vertebrate cells in culture (tissue culture) has become a routine procedure in recent years (Kruse and Patterson, (1973), Tissue Culture, Academic Press). Examples of such useful host cell lines are VERO, HeLa, Chinese hamster ovary (CHO), W138, BHK, COS-7, MDCK and myeloma and gs myeloma (available from Celltech, Slough, U.K.) cell lines. Expression vectors for such cells may include (if necessary) an appropriate origin of replication, as well as a promoter located in front of the gene to be expressed, along with any necessary ribosome binding sites, RNA splice sites, polyadenylation sites and transcriptional terminator sequences.

For use in mammalian cells, the control functions on the expression vectors are often provided by viral material. For example, commonly used promoters are derived from human cytomegalovirus (HCMV), polyoma virus, adenovirus 2 and, most frequently, simian virus 40 (SV40). The early and late promoters of SV40 virus are particularly useful because both are obtained easily from the virus as a fragment which also contains the SV40 viral origin of replication (Fiers et al., (1978) Nature 273:113). Further, it is also possible, and often desirable, to utilize promoter or control sequences normally associated with the desired gene sequence, provided such control sequences are compatible with the host cell system.

An origin of replication may be provided either by construction of the vector to include an exogenous origin, such as may be derived from SV40 or other viral (e.g. polyoma virus, adenovirus, VSV or BPV) source, or may be provided by the host cell chromosomal replication mechanism. If the vector is integrated into the host cell chromosome, the latter is often sufficient.

The vectors containing the DNA segments of interest (e.g. the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, lipofection or electroporation may be used for other cellular hosts (Maniatis et al., (1990) Molecular Cloning: A Laboratory Manual, 2nd Edition, Cold Spring Harbor Press).

Once expressed, the constructs of the present invention can be purified according to standard procedures of the art, including ammonium sulfate precipitation, affinity columns, column chromatography and gel electrophoresis (Scopes, (1982) Protein Purification, Springer Verlag, N.Y.). Binding affinities of the constructs so expressed may be ascertained by techniques known to the art, as more fully exemplified in the example section of this specification.

Substantially pure CDR-grafted antibodies or binding proteins thereof of at least 90 to 95% homogeneity are preferred, and 98 to 99% or more homogeneity is most preferred for pharmaceutical uses. Once purified, partially or to homogeneity as desired, the CDR-grafted antibodies may then be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, N.Y.).

The CDR-grafted antibodies or binding proteins thereof of the present invention will typically find use in treating T cell mediated disorders. For example, typical disease states suitable for treatment include autoimmune diseases, such as Type I diabetes, multiple sclerosis, rheumatoid arthritis, systemic lupus erythematosus, Crohn's disease and myasthenia gravis.

Therapeutic use of the T cell antibodies of the invention is premised upon the correlation between a specific immune related disease and the preferential expression of a particular T cell antigen receptor V region gene product or the expanded usage of a particular T cell antigen receptor V gene. The T cell antigen receptor V regions are useful in part because it is possible to regulate the immune response in an individual by specific therapeutic intervention utilizing the T cell antigen receptor. Specifically, the presence or expression of a particular variable region locus has been shown to correlate with particular immune-related disorders. By determining the particular V region loci associated with a particular immune disorder, one can treat the individual by inhibiting the attack by the T cells carrying the particular V region.

The term treatment in the instant invention is meant to include the situations of "prevention", "suppression" or "treatment" of the disease. "Prevention" involves administration of the protective composition prior to the induction of the disease. Thus, for example, in the animal model, EAE, successful administration of a protective composition prior to injection of the encephalitogen that induces the disease results in "prevention" of the disease.

"Suppression" involves administration of the composition after the inductive event but prior to the clinical appearance of the disease. Again, using the EAE example, successful administration of a protective composition after injection of the encephalitogen, but prior to the appearance of neurological symptoms comprises. "suppression" of the disease.

"Treatment" involves administration of the protective composition after the appearance of the disease. In the EAE example, successful administration of a protective composition after injection of the encephalitogen and after clinical signs have developed comprises "treatment" of the disease.

Animal model systems which can be used to screen the effectiveness of the antibodies or binding proteins thereof in protecting against or treating the disease are available. Systemic lupus erythematosus (SLE) is tested in susceptible mice as disclosed by Knight et al., (1978) J. Exp. Med. 147:1653 and Reinersten et al., (1978) New Eng. J. Med. 299:515. Myasthenia Gravis (MG) is tested in SJL/J female mice by inducing the disease with soluble AChR protein from another species as described in Lindstrom et al., (1988) Adv. Immunol. 42:233–284. Arthritis is induced in a susceptible strain of mice by injection of Type II collagen as described by Stuart et al., (1984) Ann. Rev. Immunol. 42:233–284. Adjuvant arthritis is induced in susceptible rats by injection of mycobacterial heat shock protein as described by Van Eden et al., (1988) Nature 331:171–173. Thyroiditis is induced in mice by administration of thyroglobulin as described by Maron et al., (1980) J. Exp. Med. 152:1115–1120. Insulin dependent diabetes mellitus (IDDM) occurs naturally or can be induced in certain strains of mice such as those described by Kanasawa et al., (1984) Diabetologia 27:113. EAE in mouse and rat serves as a model for MS in human. In this model, the demyelinating disease is induced by administration of myelin basic protein as described by Paterson, (1986) Textbook of Immunopathology (Mischer et al., eds.) Grune and Stratton, New York, pp 179–213; McFarlin et al., (1973) Science 179:478–480: and Satoh et al., (1987) J. Immunol. 138:179–184.

The CDR-grafted antibodies or binding proteins thereof of the present invention may also be used in combination with other antibodies, particularly mAbs reactive with other markers on human cells responsible for the diseases. For example, suitable T cell markers can include those grouped into the so called "Clusters of Differentiation," as named by the First International Leukocyte Differentiation Workshop (Bernhard et al., (1984) Leukocyte Typing, Springer Verlag, N.Y.

Generally, the present CDR-grafted antibodies or binding proteins will be utilized in purified form together with pharmacologically appropriate carriers. Typically, these carriers include aqueous or alcoholic/aqueous solutions, emulsions or suspensions, including saline and buffered media. Parenteral vehicles include sodium chloride solution, Ringer's dextrose, dextrose and sodium chloride and lactated Ringer's. Suitable physiologically acceptable adjuvants, if necessary to keep the complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, can also be present (Mack, (1982) Remington's Pharmaceutical Sciences, 16th Edition).

The constructs of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the CDR-grafted antibodies or binding proteins thereof of the present invention, or even combinations of constructs according to the present invention and CDR-grafted antibodies having different specificities.

The route of administration of pharmaceutical compositions according to the invention may be any of those commonly known to those of ordinary skill in the art. For therapy, including without limitation immunotherapy, the CDR-grafted antibodies or binding proteins thereof of the invention can be administered to any patient in accordance with standard techniques. The administration can be by any appropriate mode, including parenterally, intravenously, intramuscularly, intraperitoneally, or also, appropriately, by direct infusion with a catheter. The dosage and frequency of administration will depend on the age, sex and condition of the patient, concurrent administration of other drugs, counter indications and other parameters to be taken into account by the clinician.

The constructs of this invention can be lyophilized for storage and reconstituted in a suitable carrier prior to use. This technique has been shown to be effective with conventional immunoglobulins and art-known lyophilization and reconstitution techniques can be employed. It will be appreciated by those skilled in the art that lyophilization and reconstitution can lead to varying degrees of antibody activity loss (e.g. with conventional immunoglobulins, IgM antibodies tend to have greater activity loss than IgG antibodies) and that use levels may have to be adjusted to compensate.

The compositions containing the present CDR-grafted antibodies or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of CDR-grafted antibody or binding protein thereof per kilogram of body weight, with doses of 0.05 to 2.0 mg/kg/dose being more commonly used. For prophylactic applications, compositions containing the present constructs or cocktails thereof may also be administered in similar or slightly lower dosages.

A composition containing a construct according to the present invention may be utilized in prophylactic and therapeutic settings to aid in the alteration, inactivation, killing or removal of a select T cell target population in a mammal.

In another embodiment, the constructs described herein may be used extracorporeally or in vitro selectively to kill, deplete or otherwise effectively remove the target cell population from a heterogenous collection of cells. Blood from the mammal may be combined extracorporeaily with the CDR-grafted antibodies or binding proteins thereof whereby the undesired cells are killed or otherwise removed from the blood for return to the mammal in accordance with standard techniques.

In addition to the therapeutic uses, the constructs will find use in other settings. In one embodiment, the present antibodies or binding proteins are useful in an investigational setting. The T cell receptor binding proteins or antibodies of the invention are also useful in structural and functional studies regarding the T cell receptor. Besides serving as substrates or binding domains for specific forms of T cell receptors, these antibody constructs may serve as tools for the investigation of conformational studies to approximate the native configurations of various portions of the T cell receptor. In yet another embodiment, the T cell antibodies or binding proteins thereof can be used as diagnostic probes. In one specific embodiment, the constructs of the present invention may be used in determining the amount or the presence of a certain T cell v region subfamily in a biological sample. One such assay is described in Rittershaus—WO92/08981, published May 26, 1992 entitled "Therapeutic and Diagnostic Methods Using Total Leukocyte Surface Antigens". As such, the present invention provides for methods for diagnosing an immune related disease, such as MS, based on detecting the specific subset of T cell antigen receptor in a biological sample.

The CDR-grafted antibodies or their binding proteins may be labelled in accordance with techniques known to the art. The constructs are also suitable for other in vivo purposes. For example, they can be used for selective cell treatment of peripheral blood cells where it is desired to eliminate only target T lymphocytes or similarly in cell culture to eliminate unwanted T lymphocytes.

The following Examples are intended to more specifically describe certain aspects of the present invention but are not to be considered limitative thereof.

EXAMPLE 1

TM27—SYNOPSIS OF WORK

1. BALB/c mice were immunized with the T cell leukemia cell line HPB-All (once intraperitoneally and twice intravenously).
2. Spleen cells were harvested from these mice and fused with mouse myeloma immortalizing cell line P3X53AG8.653.
3. Selection of appropriate clones was accomplished in HAT media.
4. Screening of the clones so selected for appropriate binding was accomplished by immunoprecipitation of radiolabelled HPB-ALL.
5. Subcloning was accomplished by limiting dilution.
6. Specificity was checked by PBL stimulation and CD3 modulation studies.
7. A Hybridoma secreting appropriate antibody was designated 4H11.
8. RNA was obtained from this clone and mRNA isolated. cDNA to the mRNA was prepared.
9. The cDNA was sequenced and checked for accuracy.
10. The isolated cDNAs (H and K) were cloned into M13 vectors.
11. Select human framework regions were introduced through mutagenesis, as exemplified in Example 2.
12. Humanized antibodies (~1 mg each) were purified from NSO transfectants for preliminary evaluation.

Five different TM27's have been made:

TM27L (SEQ ID NO:5): with Leucine at position 48 of heavy chain.

TM27I (SEQ ID NO:6): with isoleucine at position 48 of heavy chain.

TM27.1 (SEQ ID NO:7): with FS to VF (78–79) changes.

TM27.2 (SEQ ID NO:8): with VTML/T to LSIS/N (67–70/73) changes.

TM27.3 (SEQ ID NO:9): with V to R (92) changes.

DETAILED EXPERIMENTAL DESCRIPTION

SUMMARY

The aim of this project was to humanize a murine anti-human TCR (T cell receptor) Vβ 5.2/5.3 monoclonal antibody (TM23) and to generate a humanized antibody expressing cell line suitable for process development. The humanized anti-TCR Vβ 5.2/5.3 monoclonal antibody is TM27.

Murine Antibody

The 4H11 hybridoma was developed by fusion of a mouse myeloma cell line, P3X63AG8.653, to spleen cells from Balb/c mice immunized with the T cell leukemia cell line HPB-ALL. The hybridoma expresses the monoclonal antibody TM23 with specificity to the human T cell receptor (TCR) Vβ 5.2 and 5.3. The isotype is IgG2a / kappa.

Humanization

The cDNA encoding the heavy and light chains of TM23 was isolated from the 4H11 CDNA library constructed using mouse IgG2a and kappa specific 3' end primers. The CDNA clones isolated were confirmed by DNA sequencing and internal amino acid sequencing. The CDRs (complementarity determining regions) of the heavy and light chains were identified according to the alignment of conserved mouse framework sequences. The L, V, (D), J (L, leader; V, variable; D, diversity; J, joining) DNA fragments were isolated using PCR and cloned into CHO cell expression vectors, pTCSLCκDHFR and pTCSLCg1NeoAp, which carried human kappa and IgG1 constant region cONA, respectively, for mouse V/human C chimeric antibody expression.

Based on the comparison of amino acid sequences deduced from cDNA clones, the TM23 heavy chain was found to belong to Kabat subgroup IB. The Vκ sequence was found to belong to Kabat Vκ V. Therefore, the human NEWM and REI frameworks were chosen for humanization of heavy and light chain respectively. The rearranged V(D)J fragments (except part of 5' V and 3' J) were cloned, into M13 vectors which carried leader and intron sequences in genomic configuration, to generate complete genomic L-V (D)J constructs.

Myeloma Expression

After construction of CDR-grafted V(D)J regions by mutagenesis, the DNA fragments were cloned into myeloma expression vectors, which carried the constant region of human kappa and IgG1, respectively. Five humanized heavy chains with various mutations were constructed. Each of the five heavy chain constructs was co-transfected with a humanized light chain into NSO myeloma cell line. Humanized antibodies were purified from culture supernatants of the expanded human IgG1/κ positive transfectants for evaluation. The results indica ted that TM27L, with the least mouse amino acid sequences, stained Vβ 5.3 T cells as well as the other humanized versions, if not better. TM27L was therefore chosen for further development and was designated as TM27.

CHO Cell Expression

The heavy and light chain leader and V regions of TM27 were isolated from myeloma constructs by PCR for cloning in cDNA configuration into CHO cell expression systems, pTCSLCg1NeoAp (heavy) and pTCSLCκDHFR (light) as described above. The CHO cell transfectants were selected and human IgG1/κ positive cells were cloned. One of the highest producers, TM27L-662-35, was expanded for cell banking and small scale humanized Ab preparation. The CHO expressed TM27 antibody has been characterized throughout the progress of the project and is comparable with that from myeloma cell lines and the parental TM23. Concurrently, CHO cell clones were subjected to amplification and cloning to increase antibody expression and demonstrate suitability of the strain for productivity improvement.

DETAILED DESCRIPTION

Immunization of BALS/c Mice with HPB-ALL

The β F1 (an anti-human β chain T cell receptor constant region monoclonal antibody) immunoprecipitate of human T cell leukemia HPB-ALL cells ($3\times10^7$) obtained from Dr. Michael Brenner (Harvard Medical School) was mixed with complete Freund's adjuvant and injected intraperitoneally (i.p.) into a BALB/c mouse. After 5 weeks, the mouse was boosted with $3\times10^7$ cells in saline on 3 consecutive days, first i.p. and then twice intravenously (i.v.).

Fusion of Spleen cells with P3X63AG8.653

The fusion was done by established techniques three day after the final i.v. boost. The spleen cells, in 5-fold excess, were fused with P3X63Ag8.653 cells (a mouse myeloma, non-Ig secreting line derived from BALB/c mouse, ATCC CRL 1580) using 50% polyethylene glycol 1500 (BDH, Dorset, England).

HAT Selection of Fused Cells

The fused cells were plated in 96-well plates with $2\times10^5$ BALB/c thymocytes per well as feeders and selected in RPMI-1640 media containing 15% FBS (fetal bovine serum) and HAT (6 mM hypoxanthine, 50 mM aminopterin and 2 nM thymidine). The cells were incubated in humidified air with 5% $CO_2$ at 37° C.

Screening of Hybridoma

After 13–14 days, the wells with growth were screened by both ELISA and immunoprecipitation of $^{125}$I-radio-labeled HPB-ALL cells. Under the conditions of immunoprecipitation, CD3 molecules are dissociated from the TCR α and β chains. The hybridomas which reacted with HPB-ALL were expanded into T-75 flasks for further cloning.

Cloning of Hybridomas of Interest

Hybridomas with the specificity for HPB-ALL TCAR (T cell antigen receptor) were cloned by limiting dilution. Cells were plated out on 96 well culture plates with 2 fold serial dilutions of cell density ranging from 2 to 0.015 cell/well. The best growing colony with the highest productivity was chosen for repeating the above procedure twice. One of the final colonies after these two additional rounds of selection, 4H11, was identified. The mAb expressed by clone 4H11 immunoprecipated molecules identical to the TCR α and α chains precipitated with the β F1 mAb, which reacts with constant region of TCR β chain. The result suggested that this mAb had the specificity to TCR β chain expressed on the HPB-ALL T cells. The antibody was called TM23 for convenience.

Characterization of Monoclonal Antibody from Hybridoma 4H11, TX23

Isotyping of TM23 mAbs was performed using a commercially available kit (Zymed, South San Francisco, Calif.). The results indicated that it is a mouse IgG2a/κ isotype.

To confirm the anti-TCR reactivity of the TM23 mAb, it was screened for its ability to comodulate the CD3 molecule from the surface of HPB-ALL cells. Previous studies have shown that mAbs to either the α or β chain of TCR can comodulate CD3 from the cell surface when cells are preincubated with the anti-TCR mAbs. When HPB-ALL cells were preincubated with TM23, a significant decrease in reactivity with the anti-CD3 mAb Leu-4 was seen when compared to the Leu-4 reactivity seen in untreated cells.

Normal human PBL (peripheral blood lymphocyte) was tested for reactivity with TM23. From 1.6% to 3.0% of the PBL T cells studied reacted with TM23. This result is typical of results obtained with several other mAbs which have been shown to react with specific V region determinants.

To determine if TM23 binds to the same epitope as 1C1, a mAb which reacts with human Vβ 5.2 and 5.3 subfamilies (Boylston, et al., 1986 J. Immunol. 137:741), the ability of one mAb to block the binding of the other was studied. When HPB-ALL cells were first incubated with TM23, the binding of fluorescein-conjugated 1C1 was inhibited.

Also, when cells were incubated first with 1C1, the binding to TM23 was inhibited. This result suggests that TM23 and 1C1 bind to the same or closely adjacent epitopes.

To further assess whether TM23 and 1C1 have similar reactivities, PBL lines were derived by stimulating with the other mAb. Each line was then examined for reactivity with each mAb. When a PBL line was established by stimulation with TM23, both 1C1 and 4H11 reacted with a similar percentage of cells. The same is true of a 1C1 stimulated PBL line.

Growing of 4H11 Cell Culture

The 4H11 clone TM23.1 Jul. 31, 19991 was grown and expanded in DMEM/F12 media (1:1) plus 1% fetal calf serum, 100 μ/ml Penicillin, 100 μ/ml Streptomycin and 12.5 mM glutamine.

Preparation of cDNA Encoding TM23 Heavy and Light Chains

About $10^κ$ 4H11 cells were isolated by centrifugation and washed once with ice cold PBS. Total RNA was prepared using Promega RNAgents Total RNA Isolation Kit (Promega, Cat #Z5110). Poly $(A)^+$ RNA was prepared using Promega PolyATract mRNA Isolation System (Promega Cat #Z5200). The mouse IgG2a and κ specific cDNA library was prepared using the BRL SuperScript Kit (BRL Cat #82Y8SA) with the IgG2a primer (SEQ ID NO:10)
5' ATATGCGGCCGCTCATTTACCCGGAGTC-CGGGAGAAGCTCTTAGT 3,'
and κ primer (SEQ ID NO;11)
5' ATATGCGGCCGCTTAACACTCATTCCT-GTTGAAGCTCTTGACAAT 3'.

The two primers contain Xho I restriction enzyme sites and sequences complementary to the 3' ends of mouse IgG2a and κ coding regions, respectively. The CDNA was cloned into plasmid pSPORT, supplied in the Kit, and transformed into *E. coli* DH5a competent cells by electroporation. Plasmid clones carrying the right size inserts were selected for sequencing. Identification of cDNA Clones Encoding TM23 Heavy and Light Chains The mini-prep plasmid DNA with inserts of the right size (light chain clones #1, 6, 19, 20, 25 and 26; heavy chain clones #4, 9, 11, 15, 22 and 34) were subjected to double stranded DNA sequencing using the Sequencing Kit (USB Cat #70770) which has a T7 primer 5' to the DNA inserts. The sequences of light chain clones #6, 20, and 25 and heavy chain clone #34 indicated that they were mouse Ig clones. Light chain clones #6, 20 and 25 had identical sequences and #6 had a point mutation and was a nonfunctional clone. Clones #20 and 34 were sequenced using κ (SEQ ID NO;12)
5' GACATTGATGTCTTTGGGGTAGAAGTTGTT 3'
and IgG2a (SEQ ID NO:13)
5' GGTCACTGGCTCAGGGAAATAACCCTTGAC 3'
constant region specific primers. Again, the results indicated that clone #6 was a non-functional clone and clones #20 and 34 were the right clones for light and heavy chain respectively. The cDNA and amino acid sequences deduced from the two clones are shown in FIG. 1.

Due to N-terminal blocking, micro-amino acid sequencing was performed from CNBr cleaved peptide fragments isolated from polyacrylamide gels. The internal V region amino acid sequences obtained from this process were consistent with that deduced from cDNA sequences. The results confirmed that the CDNA clones isolated were the ones encoding TM23 heavy and light chain.

The CDRs of the heavy and light chains were identified according to the method of Kabat and Wu (supra) and are highlighted and underlined in FIG. 1.

PCR Isolation of V Region DNA of H and L Chains and DNA sequencing

PRODUCTION OF CHIMERIC TM23 ANTIBODY

Isolation of Murine VH DNA and NK DNA

The TM23 heavy and light chain variable regions ere adapted for insertion into expression vectors. The DNA sequence coding for the TM23 murine VH was amplified from TM23MuVH.MuIgG2a by PCR using oligonucleotide primers VH1BACK (SEQ ID NO:14)
(5' AGGTSMARCTGCAGSAGTCWGG 3')
which contains a site for the restriction enzyme PstI and VH1FOR (SEQ ID NO:15)
5' TGAGGAGACGGTGACCGTGGTCCCTTG-GCCCCAG 3'
which contains likewise a BstEII site. M stands for C or A, S stands for C or G, R stands for A or G and W stands for A or T. These sites were thereby introduced at the 5' and 3' ends respectively of TM23VH DNA. The amplified DNA was cut with PstI and BstEII and ligated into the PstI and BstEII sites of double-stranded replicative (RF) form DNA of the vector M13 VHPCR1, cut with the same enzymes.

M13 VHPCR1 is an M13 phage vector derived from M13-HuVHNP (Jones et al., (1986) Nature 321:522–525) and contains an immunoglobulin promoter, signal sequence and appropriate splice sites (Orlandi et al., (1989) Proc. Natl. Acad. Sci. USA 86:3833–3837).

The ligated DNA was transformed into competent *E.coli* strain TG1 (K12, Δ(lac-pro), supE, thi, hsd D5 [F' tra D36, proA$^{A+B+}$, lacO$^4$, lacZ M15]. Single-stranded DNA was prepared from the recombinant phage plaques obtained.

The DNA sequence coding for the TM23 murine VK was amplified from TM23MuVK.MuCK by PCR using oligo-nucleotide primers VK1BACK (SEQ ID NO:16)
5' GACATCCAGCTGACCCAGTCTCCA 3'
which contains a PvuII site and VK1FOR (SEQ ID NO:17)
5' GTTAGATCTCCAGCTTGGTCCC 3'
which contains a BglII site in conjunction with two over-lapping internal primers designed to remove the HindIII site in CDR3, oligo 943 (SEQ ID NO:18)
5' CCGAGGAAGTTTACTATACTG 3',
and oligo 944 (SEQ ID NO:19)
5' CAGTATAGTAAACTTCCTCGG 3'
(Horton et al, (1990). PvuII and BglII sites were thereby introduced at the 5' and 3' ends of TM23 VK DNA. The amplified DNA was digested with PvuII and BglII and ligated in PvuII and BclI cut M13 VKPCR1. The enzymes BglII and BclI cut DNA to produce compatible cohesive ends which can be ligated together.

M13VKPCR1 contains the same promoter, signal sequence and splice sites as M13 VHPCR1 (Orlandi et al, (1989).

The ligated DNA was transformed into *E.coli* TG1 and single-stranded DNA prepared from the recombinant phage plaques obtained.

PCR products of the correct size, 359 base pairs (bp) for VH and 288 bp for VK were obtained. The VH DNA was inserted into the vector M13VHPCR1 to give M13 TM23MuVH. The VK DNA was inserted into the vector M13VKPCR1 to give M13 TM23MuVK.

Confirmation of DNA Sequences

It was confirmed that the correct DNA sequences had been cloned and that no spurious mutations had been introduced by the PCR. The sequence of single-stranded M13 phage DNA of the entire 823 base pair (bp) VH region including the promoter, signal sequence, splice sites and 5' and 3' untranslated sequences was obtained by the dideoxy method (Sanger et al, 1977) using T7 DNA polymerase or Sequenase.

The sequence of single-stranded M13 phage DNA of the entire 630 base pair (bp) VK region including the signal sequence, splice sites and 5' and 3' untranslated sequences was obtained by the dideoxy method, as above.

DNA clones with the desired sequence for TM23 VH adapted for insertion in the expression vector were identified. One of these, #2, was selected for further work. The introduction of the requisite restriction sites necessary for insertion of VH into the expression vector resulted in 1 amino acid change at the N-terminus; lysine (K) at position 5 to glutamine (G) and one change at the C-terminus, serine (S) at position 108 to threonine (T).

DNA clones with the desired sequence for TM23 VK adapted for insertion in the expression vector were identified. One of these, #4, was selected for further work. The amino acid sequence of CDR3 was not altered by the removal of the Hind III site, but the introduction of the requisite restriction sites necessary for insertion of VK into the expression vector resulted in three amino acid changes at the N-terminus; methionine (M) at position 4 to leucine (L), threonine (T) at position 7 to serine (S) and threonine (T) at position 8 to proline (P), and one change at the C-terminus, valine (V) at position 105 to glutamine (E), due to the primers used.

Cloning of V region DNA Fragments into M13 Vector

Transfer of the cloned murine variable region to expression vectors containing human constant region genes for subsequent expression of the antibody in mammalian cells was accomplished.

Selection of IgG Isotype for Humanization

Human IgG1 isotype was chosen for TM27 for the following reasons:

1. IgG1 has the capability of mediating both ADCC (antibody dependent cell cytotoxicity) and CDC (complement dependent cytotoxicity). Therefore, it may be more effective in down-regulating Vβ 5.2/5.3 T cells; and 2. IgG1 has been used more often in Ab humanization.
Human Framework Selection for CDR Graft

PRODUCTION OF HUMANISED TM23 ANTIBODY

Design of Humanised TX23 Variable Region Sequences

Selection of human framework sequences to receive the TM23 CDRs and determination of essential murine residues that must be substituted in the human framework was carried out. Computer assisted comparisons of the amino acid sequences of TM23 VH and VK were made both with the known sequences of other murine antibodies and human antibody VH and VK sequences.

The program ALLIGN from DNASTAR Ltd, London W13 9BL, UK, was used, run on a Compaq 386 processor. AALIGN aligns two proteins sequences using the Lipman-Pearson and Needleman-Wunsch methods. First, the Lipman-Pearson method determines the best regions of homology. Then the Needleman-Wunsch method provides the final alignment of the sequences.

The alignments produced were then examined paying particular attention to factors such as the length of the CDRs and residues believed to be critical in supporting the conformation of the CDRs, for example positions 71 and 94 and residues close to the CDRs (Tramontano et al, (1990); Foote and Winter, (1992)).

Comparison with consensus sequences for the Kabat subgroups assigned the TM23 murine VH to Kabat subgroup VK V. There are no amino acid sequences which are unusual for these subgroups in the TM23 frameworks.

The human antibodies NEWM and REI provided the framework sequences for VH and VK respectively. For VH, in addition to the CDRs, the murine residues at 27 to 30 inclusive and 71 were used. These framework residues are thought to be important in supporting the conformation of the CDRs (Foote and Winter, (1992)). Residue 71 may fix the relative dispositions of CDR1 and CDR2, according to whether there is a bulky side chain (lysine or arginine) or a smaller side chain (valine or alanine) present (Tramontano et al., (1990). Therefore valine 71 in NEWM VH was replaced with lysine as in TM23 VH. Residues 27 to 30 form part of the structural, rather than hypervariable, antigen-binding loop as defined by Chothia and Lesk (1987). Framework residues 47 to 49 may also be important for antibody structure (Foote and Winter, (1992)). Therefore two alternative humanised heavy chains were constructed: one with isoleucine (I) at position 48 as in NEWM; and one with leucine (L) at position 48 so that residues 47 to 49 from the murine VH were preserved. A comparison of the murine VH sequence with the humanised version is shown in Example 2.

No alterations were made to the human REI framework chosen for TM23 VK. A comparison of the murine VK sequence with the humanised version is also shown in Example 2.

Description of Mammalian Expression Vector pTCSNeo

The plasmid pTCSNeo contains a unique Xho I cloning site into which genes of interest are inserted. Transcription of the inserted gene is driven by the regulatory sequences consisting of a SV40 enhancer upstream of the adenovirus 2 major late promoter (Ad2 MLP). The Ad2 MLP is itself located upstream of the adenovirus tripartite leader. The inserted gene is flanked by a polyadenylation signal from murine immunoglobulin kappa (Igκ) at the 3' end. Mammalian selection is conferred by the neomycin resistance gene (Neo'). The plasmid also provides the bacterial origin of replication and β-lactamase gene (Amp').

Construction of Expression Vector pTCSLNeo

Two complementary oligonucleotides with the sequences:
anti-sense (SEQ ID NO:20),
5' CGACATCGATGATATCGAATTCGCGGC-CGCCAGCTGGGGCCCTCTAGAC 3'
and sense (SEQ ID NO:21),
5° CGAGTCTAGAGGGCCCCAGCTGGCGGC-CGCGAATTCGATATCATCGATG 3'
were reannealed and ligated to pTCSNeo which had been digested with XhoI and filled in with dT. The resulting plasmid, pTCSLNeo, with the polylinker consisting of multiple restriction enzymatic sites in the orientation of 5' XhoI/XbaI/ApaI/PvuII/NotI/EcoRI/EcoRV/ClaI 3', is convenient for inserting the gene of interest for expression. The neo' gene can be changed to other selection marker genes as well.

Construction of Depression Vector pTCSLDHFR*

The neo' gene in pTCSLNeo was removed by digestion with the restriction enzyme HindIII and BamHI and religated with the murine mutant DHFR (dihydofolate reductase) (DHFR*) gene fragment generated by HindIII and BamHI digestion of plasmid pSV2-DHFR obtained from Dr. Paul Berg (Department of Biochemistry, Stanford University Medical School).

Description of Plasmid pSV184 H-Neo/DNS-VκCκ

The plasmid pSV184 ΔH-Neo/DNS-VκCκ (obtained from Dr. Lee Herzenberg, Stanford University Medical School—see Thesis of Jeffery Dangl, page 48–67) is a mouse V and human C chimeric construct in which the rearranged κ chain V-J region gene segment isolated from a Dansyl Chloride specific murine hybridoma was fused to a human genomic $C_k$ fragment (pSV184ΔH-Neo-$C_k$.

Isolation of the human kappa chain constant region by the PCR method

Using the undigested plasmid pSV184ΔH—Neo/DNS-VκCκ (pSVHuk) which contains the human kappa chain constant region, PCR was performed with two primers (one forward, one reverse) to isolate the constant region. The oligomers (primers) were obtained from operon. The PCR reaction reagents were from the GeneAmp DNA amplification reagent kit with AmpliTaq (Perkin-Elmer Cetus) The PCR reactions were set up in three different concentrations of $Mg^{2+}$. Aliquots of the PCR products were analyzed on a 1% agarose gel. The PCR product from the first sample of $Mg^{2+}$ (concentration 1.5 mM) was chosen. The primers, which flank the C region, were designed to contain restriction enzyme sites for cloning purposes. Thus, the amplified DNA was digested with EcoRI (at the 3' end). The site at the 5' end (PvuII) was not digested. The digested DNA fragment was then run on a 1% agarose gel and the 300 bp band excised. The DNA was extracted from the gel and a small aliquot was analyzed on a 1% agarose gel to determine quality and to estimate quantity. The 300 bp band appeared to be clean and the total amount of DNA estimated to be −140 ng.

Human kappa chain constant region cloned into the pBS $KS^+$ vector and sequenced The EcoRI-digested DNA fragment of the human kappa chain constant region was inserted into the vector pBS $KS^+$, which had been digested with Sma I and EcoR I, using T4 DNA ligase. This ligation mixture was used to transform *E. coli* DH5α competent cells. Single colonies were picked and used to inoculate 24 liquid cultures. DNA was prepared from each of the cultures. Each DNA sample was digested with Pvu II (5' end of $C_a$) and EcoR I (3' end of $C_k$), and analyzed on a 2% agarose gel. Due to difficulty in separating the lower range bands (300 bp), the DNA samples were digested with PvuII only. After analysis on a 2% agarose gel, 19 out of 24 were correct for $C_k$ insert. Samples #1–5 (of the 19 correct samples) were chosen to be sequenced, using T7 and T3 primers (sequences in the vector flanking the insert). Other sequencing reagents were from the Sequenase Version 2.0 kit (USB). Sample #15 proved to have correct sequence for the human kappa chain constant region.

Human kappa chain constant region cloned into the mammalian expression vector pTCSLDHFR* to become pTCS-LC$_k$DHFR*

The human kappa chain constant region was isolated from the pBS KS vector (Sample #5) using PvuII and EcoRI restriction enzymes. However, due to the previous problem of band separation, a second digest was performed with the construct pBS/Human $C_k$. The second digest involved EcoRI and XbaI (located 5' to the PvuII site) yielding a fragment ~300 bp. This fragment was then gel purified and subjected to a PvuII digest, to remove the remaining small fragment of vector at the 5' end of the $C_k$. This final fragment was gel purified and then analyzed on a 1% agarose gel for quality and to estimate quantity. The $C_k$ DNA appeared to be a clean band at ~280 bp and the total quantity estimated to be ~135 ng.

Due to the existence of three EcoRI sites in the expression vector, PTCSLDHFR*, it was determined that cloning into the PvuII site only would be best. Since the $C_k$ DNA was prepared by digestion with PvuII-EcoRI, the EcoRI end was repaired (to form blunt end) using Klenow fragment. The repaired, blunt-ended $C_k$ DNA was ligated to the pTCSLDHFR* vector which had been PvuII digested and phosphatase-treated (using calf intestinal phosphatase). This ligation mixture was used to transform $E.\ coli$ DH5α competent cells. Single colonies were picked and used to inoculate 24 liquid cultures. DNA was prepared from each. All DNA samples were digested with PvuII and HindIII, and analyzed on a 1% agarose gel. It was determined that five samples, out of 24, contained the $C_k$ insert in the correct orientation. Sample #7 was chosen for continuation.

Replacement of the mutant DHFR* gene with the wild type DRFR gene

For the expression of the vector pTCSLC$_k$DHFR* in CHO(dhfr')DUX B11 cells, the DHFR* gene was replaced with the DHFR gene. DNA from pTCSLC$_k$DHFR* sample #7 as well as pSV2-DHFR (plasmid obtained from Dr. Paul Berg, Department of Biochemistry, Stanford University Medical School) was digested with restriction enzymes HindIII and BglII to isolate the respective gene fragments. Upon analysis, it was determined that an additional BglII site in the pTCSLC$_k$DHFR* vector removed a portion of the polyA site also, which would interfere with the vector function. Therefore, the digests were repeated using HindIII and BamHI. The (DHFR*)pTCSLC$_k$ portion of the vector was treated with phosphatase. Then both the isolated fragments (PTCSLC$_k$ and DHFR) were gel purified and analyzed on a 1% agarose gel for quality and to estimate quantity. Both bands appeared to be clean and estimated to be of similar concentration, ~40–50 ng/ml. The DHFR gene was ligated to the pTCSLC$_k$ vector using T4 DNA ligase. The ligation mixture was used to transform $E.\ coli$ DH5α competent cells. Single colonies were picked and used to inoculate 24 liquid cultures. DNA was prepared from each. The DNA was analyzed by restriction enzyme digestion with HindIII and BamHI. From 24 cultures, 23 had the correct bands indicating the insertion of the DHFR gene into the pTCSLC$_k$ vector. Sample #22 was selected for further use.

in vitro Mutagenesis to Construct CDR Grafted V Regions with Human Framework

Construction of Humanized Variable Genes

A humanized VH gene was constructed by site-directed mutagenesis of M13 VHPCR1 template, which comprises a synthetic VH gene with the framework regions of the human myeloma protein NEWM (see Jones et al, 1986). Single stranded template DNA was prepared from M13 VHPCR1 grown in a dut, ung $E.coli$ strain RZ1032 so that the template DNA contained uracil in place of thymine. Mutagenic oligonucleotide primers were synthesised to encode the TM23 CDRs and approximately 15 bp of perfectly matched flanking sequence on either side. If the TM23 CDR sequence matched the template sequence shorter oligonucleotide primers were used. The primers used were CDR1 (SEQ ID NO:22)

5' TGGCTGTCTCACCCAGTTTACACCATAG-GCGGTTAATGAGAAGCCAGACACGG 3', CDR2 (SEQ ID NO:23)

5' TGCTGGTGTCCTTTCAGCATTGT-CACTCTGGATTTGAGAGCTGAATTATAGTCT GTATTTCCATCACCCCATATCATTCCAA$^T$/$_G$CCACTCAAGACC 3', and CDR3 (SEQ ID NO:24)

5' CCAGTAGTCCATAGCATAGAGGGTAGC-CGTAACCCTATCTCTTG CACAATAATAG 3'.

The oligonucleotide primer for CDR was extended at the 3' end to include the required residues at positions 27 to 30. A mixed oligonucleotide was made for CDR2, extended at the 3' end of the CDR with either G or T at base number 402 of the VH providing 2 alternative codons such that position 48 of the VH became either L or I. The oligonucleotides (10 pmol of each) were phosphorylated with 5 units of T4 polynucleotide kinase in a total volume of 50 μl at 37° C. for 1 hour. 1 pmol of each mutagenic primer and 1 pmol of the M13 sequencing primer 3' to the V gene were annealed to 0.5 μg of template in a total volume of 20 μl by heating to 90° C. for 30 seconds, rapidly cooling to 70° C. and slowly to 37° C. The annealed primers were then extended and ligated with the addition of T7 DNA polymerase and T4 DNA ligase, incubated at room temperature for 1 hour. The uracil-containing template DNA was removed by treating the DNA with 1 unit of uracil DNA glycosylase at 37° C. for 1 hour, leaving the mutated strand intact. This DNA was amplified by PCR then analysed by agarose gel electrophoresis to check that DNA of the correct size had been produced. The DNA was cut with HindIII and BamHI and ligated into the HindIII and BamHI sites of M13mp19.

Similarly, the reshaped TM23 VK gene (TM23HuVK) was constructed by mutagenesis of an M13 phage template which comprises the DNA sequence of a VK gene with the framework regions of the human Bence-Jones protein REI. This was derived from M13 VKPCR1 which was used in the construction of the chimeric light chain, with the PvuII and BclI restriction enzyme sites used for cloning removed. The primers used were CDR5 (SEQ ID NO:25) 5'
TCTGCTTGGTACCAGTTTAAATAAT-TGCTAATGCCCTGACTT GCACTACAGGTGATG-GTC 3', CDR2 (SEQ ID NO:26)

5' TCTGCTTGGCACACCTGAGTGTAAACT-TGATGTGTAGTAGATCAGCAGCTT 3', and CDR3 (SEQ ID NO:27)

5° CCCTTGGCCGAACGTCCGAGGAAGTT-TACTATACTGCTGGCAGTAGTAG 3'.

PCR products of the expected size, 823 bp for both VHs and 620 bp for VK were obtained and cloned into the M14mp19 vector.

Verification of Humanized Variable Region DNA Sequences

It was confirmed that the required CDRs had been inserted, that no spurious changes had occurred and that the correct humanized VH and VK genes had been constructed. The complete variable regions were sequenced by the dideoxy method using T7 DNA polymerase or Sequenase. The sequences obtained were compared to the designed sequences. Clones giving the expected sequence for the two VHs were selected. These clones were named M13 TM23NMVH and M13 TM23NMVHL. A clone giving the expected sequence for the reshaped VK, #11, was selected and named M13 TM23HuVK.

Cloning of Rearranged V Regions into Mycloma Expression Vectors (Cloning of Humanized TM23 Variable Regions into Expression Vectors)

The cloned humanized variable regions were transferred to expression vectors containing human constant region genes for subsequent expression of the antibody in mammlian cells. The two humanized VH genes were isolated from M13 TM23NMVH and M13 TM23NMVHL as HindIII to BamHI fragments and ligated into the HindIII and BamHI sites of the heavy chain expression vector, pSVgpt.HuIgG1.

The humanized VK gene was isolated from M13 TM23HuVK as a HindIII to BamHI fragment and ligated into the HindIII and BamHI sites of the light chain expression vector pSVhvg.HuCK.

Restriction enzyme analysis showed that the two alternative humanized VHs were correctly inserted into the heavy chain vector to give the plasmids pSVgptTM23NMVH.HuIgG1 and pSVgptNMVHL.HuIgG1.

Likewise, the humanized VK was correctly inserted into the light chain vector to give the plasmid pSVhygTM23HuVK.HuCK.

Co-transfection of H and L Chains Constructs into NSO Cells Cotransfection of Humanized Heavy and Light Chain Genes Humanized expression plasmids were transferred to the mammalian cell lines, NSO and P3-8.653F8879.

The humanized expression plasmids were cotransfected into NSO and P3-8.653F8879 cells using the same procedure as for the chimeric expression plasmids The two humanized Heavy chain plasmids, pSVgptTM23NMVH.HuIgG1 and pSVgptNMVHL.HuIgG1 were each cotransfected with the humanized light chain plasmid, pSVhygTM23HuVK.HuCK to produce cell lines expressing two alternative humanized antibodies, TM23HuVH/HuVK and TM23HuVHL/HuVK. These expression plasmids were also cotransfected in combination with the chimeric expression plasmids to produce cell lines expressing the hybrid antibodies TM23HuVH/MuVK, TM23HuVHL/MuVK and TM23MuVH/HuVK. These hybrid antibodies provide important tools to locate the cause of any binding defect to either the heavy chain or the light chain in the humanized antibody.

Fourteen days after the transfection colonies of NSO cells were visible for all the various plasmid combinations. Only one single colony of P3-8.653F8879 cells was obtained from all the plates seeded and these were therefore discarded.

Selection of Human IgG1/kappa Positive Clones

Selection for Cells Producing Human Antibody

NSO cell lines producing humanized and hybrid chimeric/humanized antibodies were isolated. Samples of supernatant from wells containing cell colonies were screened by ELISA.

TM23HuVH/HuVK:-NSO cells from 4 wells were selected in which the culture supernatant gave the highest readings in the ELISA; D5, D10, C6 and E11. Well D5 contained 2 visible colonies, the other wells one. However, the cell lines produced from these are not necessarily clonal. Cell lines from these wells were cultured and frozen in liquid nitrogen as TM23HuVH/HuVK D5, D10, C6 and E11.

TM23HuVHL/HuVK:-NSO cells from 4 wells were selected in which the culture supernatant gave the highest readings in the ELISA; B2, B7, D8 and E9. Well E9 contained 2 visible colonies, the other wells one. However, the cell lines produced from these are not necessarily clonal. Cell lines from these wells were cultured and frozen in liquid nitrogen as TM23HuVHL/HuVK B2, B7, D8 and E9.

TM23HuVH/MuVK:-NSO cells from 4 wells were selected in which the culture supernatant gave the highest readings in the ELISA; D9, E6, F10 and C10. Wells F19 and G10 contained 2 visible colonies, the other wells one. However, the cell lines produced from these are not necessarily clonal. Cell lines from these wells were cultured and frozen in liquid nitrogen as TM23HuVH/MuVK D9, E6, F10 and G10.

TM23HuVHL/MuVKL:-NSO cells from 4 wells were selected in which the culture supernatant gave the highest readings in the ELISA; B8, C6, D2 and D8. Wells C6 and D8 contained 2 visible colonies, the other wells one. However, the cell lines produced from these are not necessarily clonal. Cell lines from these wells were cultured and frozen in liquid nitrogen as TM23HuVHL/MuVK B8, C6, D2 and D8.

TM23MuVH/HuVK:-NSO cells from 4 wells were selected in which the culture supernatant gave the highest readings in the ELISA; B9, G4, G6 and G11. All wells contained at least 4 visible colonies. The cell lines produced from these are not necessarily clonal. Cell lines from these wells were cultured and frozen in liquid nitrogen as TM23MuVH/HuVK B9, G4, G6 and G11.

First Strand cDNA Synthesis for CHO Call Expression Preparation of Cytoplasmic RNA RNA was prepared for reverse transcription. A vial of NSO TM23 HuVHL/HuVK cells was recovered from liquid nitrogen by thawing rapidly at 37° C. The cells were gradually diluted with 10 ml of Dulbecco's Modified Eagle's Medium/Ham's F12 (DMEM/F12) supplemented with antibiotics and 5% gamma globulin free fetal bovine serum (GG-free FBS). The cells were centrifuged at 1500 rpm for 5 minutes, the medium removed and resuspended in 20 ml of fresh medium in a 75 cm$^2$ flask. The culture was expanded to 30 ml in a 175 cm$^2$ flask. Actively growing cells were harvested by centrifugation and washed 3 times with cold phosphate buffered saline (PBS). Cytoplasmic RNA was prepared from the cells by the method of Favoloro et al, (1980). A total of 350 μg of cytoplasmic RNA was obtained.

CDNA Synthesis

First strand cDNA for was prepared VH and VK regions. First strand variable region cDNAs were synthesised in reactions containing 5 μg of RNA, 250 μM deoxynucleotide triphosphates (dNTPs), 15 units of ribonuclease inhibitor (Pharmacia RNAguard) and 25 pM of oligonucleotide primer. The primers were oligo 1109 for VH (SEQ ID NO:28) 5'
GGGGAAGACCGATGGGCCCTTGGTGGAG-GCTGAGGAGACGGTGACC 3'
and oligo 1095 for VK (SEQ ID NO:29)
5' AGATTTCAGCTCCTCATCAGATGGCGG-GAAGATGAAGACAGATGG 3'.

The reactions were heated to 70° C. for 10 minutes then cooled slowly to 37° C. 100 units of Moloney Murine Leukemia Virus Reverse Transcriptase was added and the reactions incubated at 37° C. for 30 minutes.

The cDNAs were amplified by PCR using the primers above in conjunction with oligo 1096 for VH (SEQ ID NO:30)
5' GCCGCTCGAGCCTCACCATGGGATG-GAGCTGTATCATCCTCTTCTTGGTAG 3'
and oligo 1094 for VK (SEQ ID NO:31)
5' GCCGCTCGAGCCTCACCATGGGATG-GAGCTGTATCATCCTCTTCTT GGTAGCAACAGC-TACAGGTGTCCACTCCGACATCCAGAT-GACCCAGAG 3'.

The PCR products were checked by agarose gel electrophoresis and were of the expected size (approximately 450 base pairs) and the DNA bands were purified from the gel.

Restriction Enzyme Digestions

The PCR products were digested for cloning into CHO vectors. The VH PCR product was digested with XhoI and ApaI. The VK PCR product was digested with XhoI and PvuII. Samples of the digested DNAs were electrophoresed on a 0.8% agarose gel. Bands of the expected size, 450 base pairs, were seen.

Isolate V regions ($V_H$ [TCS and S] and $V_s$ [S]) from CDNA by PCR amplification $V_H$ [TCS]

First strand cDNA samples of TM27 $V_a$ and TM27 $V_H$, as well as oligonucleotide primers used for amplification of these molecules by PCR, were obtained. PCR using the TM27 $V_H$ CDNA with appropriate primers was performed using Taq polymerase. The product was run on an agarose gel and purified using the Geneclean II kit (Bio101). Recovery was estimated at 1.5 ng/ml.

Transfection of COS Cells with pSR1Neo4H11 (light) and pBJ14H11 (Heavy) for C Region cDNA Isolation The mammalian expression vector pSR1Neo and PBJ1 are derivatives of pcDL-SRa296 (Takebe, et al., (1988) Mol. Cell. Biol. 8:466) as described in Lin, et al., (1990) science 249:677 in which a XhoI site located between the SRα promoter and the SV40 polyadenylation site has been replaced for convenient gene cloning by a polylinker that contains the following restriction sites: 5' XhoI/XbaI/SfiI/NotI/EcoRI/EcoRV/HindIII/ClaI 3'. In the pSR1Neo, a neomycin resistance gene was inserted between the ampicillin resistance gene and the SRα promoter. The cDNA encoding leader and V-D-J region of TM23 heavy chain was first fused to the genomic heavy chain constant region followed by insertion into the XhoI and NotI cut pBJ1 vector to generate pBJ14H11 (heavy). Similarly, the light chain cDNA encoding leader and V-J was first fused to genomic κ fragment followed by insertion into XhoI / NotI cut pSR1Neo to generate pSR1Neo4H11 (light). The two plasmids, pBJ14H11 (heavy) and pSR1Neo4H11 (light) were then co-transfected into COS-7 cells (a SV40 transformed African green monkey kidney cell line, ATCC CRL 1651) for transient expression.

Isolation of Human IgG1 Constant Region

Human IgG1 constant region cDNA was prepared from poly(A)$^+$ RNA isolated from transfected COS cells by PCR using IgG1 constant region primers: forward primer (SEQ ID NO:32)
5' GCGTGACAAGGGCCCATCGGTCTTC-CCCCTGGCACCCTC 3'
and reverse primer (SEQ ID NO:33)
5' GCGTGACAAGAATTCTCATTTACCCG-GAGACAGGGAGAGGCTCTT 3'.

The PCR constant region DNA fragment with EcoRI at 3' end (flanking the coding region) and ApaI at the 5' end (in the coding region) was cloned into pBS KS$^+$ plasmid for subcloning and sequencing. The entire constant region was sequenced using T3 and T7 primers, complemented with constant region internal primers. The clone with the correct sequence was then subcloned into plasmid pTCSLNeo to generate pTCSLCg1Neo.

Construction of Plasmid pTCSLCg1Neo

The IgG1Cg1 clone with the correct sequence in pBS KS$^+$ was cut out using the restriction enzymes EcoRI and ApaI and ligated into pTCSNeo digested with the same enzymes. The resulting plasmid, pTCSLCg1Neo, was used for further modification to generate pTCSLCgNeoApa'.

Elimination of ApaI site in pTCSLC$_\kappa$1Neo to generate pTCSLC$_\kappa$1NeoApa'

The pTCSLC$_g$1Neo CHO expression vector contains two sites for the restriction enzyme ApaI: one site located within the polylinker region used for insertion of cloned fragments; the other site located just 3' to the neo' gene. In order to simplify subsequent cloning steps, the ApaI site near neo' was eliminated. pTCSLC$_g$1Neo was partially digested with ApaI; a small aliquot was run on an agarose gel to check for presence of linear molecules (i.e. plasmids cut at only one of the two ApaI sites. The digested material was then treated with T4 DNA polymerase, which selectively removes the single-strand extensions left by ApaI without digesting double-strand DNA. Plasmids were then recircularized by ligation and transformed into HB101 competent E. coli cells. Thirty transformants were picked and used to inoculate liquid cultures. DNA was prepared from each culture, digested with ApaI and run on agarose gels. Unfortunately, plasmid DNA was degraded in these digests. ApaI digests were repeated on 21 of the 30 samples. Two isolates (#4 and 12) appeared to be linearized by ApaI while all others were cut at two sites. The two candidate clones were then digested with ApaI and HindIII to determine which ApaI site was present. In this test, the ApaI site 3' to neo' in pTCSLC$_g$1NeoApa isolate #12 was eliminated, as desired. Additional restriction digests were performed which confirmed the structure of this isolate.

Cloning the PCR isolated human kappa and heavy chain V regions into the CRO Vectors, pTCSLCL$_\kappa$DHFR and pTCSLCg1NeoApa', Respectively.

Clone the TX27 $V_k$ fragment into pTCSLC$_k$DUFR

The cDNA for the kappa chain V region for TM27 had been gel purified and digested with the appropriate restriction enzymes. A small aliquot of the DNA sample was analyzed on a 1% agarose gel to estimate quantity and to verify the quality. An extra (contaminating) band was observed at ~800 bp the concentration was estimated at 1.25 ng/ml. The V region was ligated to the pTCSLC$_\kappa$DHFR vector which had been digested with restriction enzymes XhoI and PvuII and phosphatase-treated. The ligation mixture was used to transform E. coli DH5α competent cells. Yield of transformant colonies was very low. Single colonies were picked and used to inoculate twelve liquid cultures. DNA was prepared from each, digested with XhoI and PvuII and analyzed on a 1% agarose gel. There were two positive samples, #3 and #4. Each of the positive samples was sequenced.

Clone TM27 $V_H$ fragment into pTCSLC$_\kappa$1NeoApa'

The PCR product corresponding to the $V_H$ region of TM27 was gel-purified and digested with the appropriate restriction enzymes (XhoI and ApaI). However, since it had been noted that the ApaI digestion may not have been complete, this digestion was repeated. A small aliquot was analyzed on an agarose gel to estimate quantity and to verify the quality. The concentration of the band corresponding to the $V_H$ region was estimated at 0.4 ng/ml. As in the case of the $V_a$ fragment, an extra band was observed at ~800 bp, suggesting that the purity of this material was also not as expected. The $V_H$ region was ligated to the pTCSLC$_g$1NeoApa' vector, which had been digested with the restriction enzymes XhoI and ApaI and phosphatase-treated. The ligation mixture was used to transform E. coli DH5α competent cells. Very few transformants were recovered. Six colonies were picked and used to inoculate liquid cultures. Miniprep DNA was prepared from each, digested with XhoI and EcoRI, and analyzed on agarose gels. One candidate clone was recovered from the first ligation, pTCSLHuV$_H$4HC$_g$1NeoApa (isolate #6). In order to obtain more candidate clones (in case the single isolate #6 failed to contain the correct sequence in subsequent tests) additional ligations were set up using 1) the $V_H$ PCR product, repurified on low melting point agarose to remove the high-molecular-weight contaminating band and 2) a $V_H$ PCR product From seized using cDNA and primers. From these ligation reactions, eight additional transformants were analyzed and five candidate clones recovered: isolates #19, 10, 11, 12, and 14.

Sequence cloned V regions on both strands to confirm expected DNA sequence

Primers designed to facilitate DNA sequencing analysis of V regions inserted in the pTCSLC$_g$1NeoApa' and pTCS-LC$_k$DHFR vectors were obtained from Operon Research. The forward primer was located within pTCS vector sequences and was used for sequencing V inserts in both pTCSLC$_g$1NeoApa' and PTCSLC$_k$DHFR vectors. Reverse primers were situated within the $C_k$ or $C_g$1 sequences, and used for sequencing $V_k$ and $V_H$ inserts, respectively.

Double strand sequencing of the human kappa chain V region

The two samples from TM23 (#3 and #4) were sequenced for both strands. The reverse strand was sequenced entirely, through the restriction enzyme sites (3'-5'; PvuII-XhoI) using the primer HUCK5PR. The forward strand sequence was determined using two different primers, PTCSFOR and PTCSFWD. Full length sequence through the restriction enzyme sites (5'-3'; XhoI-PvuII) was obtained by combining the sequences yielded from each of the primers. A small area of compression was seen to be present in the forward strands which was not resolved with either of the primers or by using a sequencing method that alleviates such compressions. However, the reverse strand proved to have correct sequence in this area. Both samples #3 and #4 appeared to have correct sequence, with sample #4 chosen to be used for mammalian cell transfection.

Double strand sequencing of the TM27 gamma chain V region

The $V_H$ fragments of pTCSLHuV$_H$4HC$_g$1NeoApa' (isolates #6 and 9) were sequenced completely on both strands. The humanized $V_H$ fragment of isolate #6 matched the expected sequence through the coding region. There was a single base pair substitution (C to T) at position −2 (relative to initiating ATG), which was not expected to affect expression. The $V_H$ fragment of isolate #9 contained two substitutions in the coding region. The four additional candidate clones were not sequenced.

Co-transfect coS and CHO cells with TM27 and CONTROL plasmids

Recipient cells were CHO dhfr DUX B11 and COS-1. The CHO DUX B11 cell line was obtained from Biogen Inc. For CHO transfection, five micrograms of the TM27 plasmids pTCSLHuV$_k$4HC$_k$DHFR (isolate #4), pTCSLHuV$_H$4HC$_g$1NeoApa' (isolate #6), and the vectors pTCSLDHFRApa and pTCSLNeoApa' was linearized by digestion with the restriction enzyme AatII. The TM27-containing plasmids (labelled "TM27L") were co-precipitated in ethanol and resuspended in $H_2O$. Similarly, the vector plasmids (labelled "CONTROL") were co-precipitated and resuspended in $H_2O$. Each of the co-precipitated plasmids were transfected into $10^7$ CHO cells by electroporation, using a BioRad Gene Pulser at 250 V and 960 mF. Transfected cells were then grown in α Minimal Essential Medium (αMEM) supplemented with thymidine, adenosine and deoxyadenosine (non-selective media) for two days prior to selection.

For COS transfection, five micrograms of uncut TM27L plasmids and vector plasmids were co-precipitated in ethanol and resuspended in $H_2O$. Plasmids were transfected into $4.1 \times 10^6$ COS cells by electroporation. Transfected cells were grown in Dulbecco's Modified Eagle Medium (DMEM) for three days, then supernatants harvested for assays.

Analyze supernatants of COS transfectants by human IgG1 ELISA and staining

Production of human IgG by COS cells was measured by human IgGI ELISA on cell culture supernatants. Microtiter plates were coated with mouse anti-human IgG1 Fc antibody in PBS and blocked in blocking buffer (1% BSA in PBS). Supernatants were added in 100 μl samples; appropriate dilutions in blocking buffer were assayed as necessary. Captured IgG was detected with horseradish peroxidase-conjugated goat anti-human Igκ antibody and OPD (o-phenylenediamine). Supernatants from TM27L-transfected COS cells showed levels of 95 ng/ml human IgG. Human IgG from CONTROL-transfected COS cells was undetectable. Flow cytometry was performed on supernatants from TM27L-transfected COS cells, concentrated -6-fold. Intensity of staining on HPB cells, as indicated by mean channel fluoresence, was about 9-fold lower than that obtained with purified TM27L (purified from NSO cells) at ~2.5 mg/ml. On Jurkat cells, staining was at background level.

Selection of CHO transfectants

CHO transfectants were placed under selection in αMEM media lacking nucleotide supplements (to select DHFR$^+$ on pTCSLHuV$_k$4HC$_k$DHFR) and containing Geneticin (G418: to select neo' on pTCSLHuV$_H$4HC$_g$1NeoApa'). Cells were plated at $2.0 \times 10^5$ cells/ml in 24-well plates.

Analyze supernatants of CHO transfectants by human IgG1 ELISA

After 12 days in selective media, supernatants from confluent wells were harvested and assayed by human IgG1/κ ELISA. Concentrations in TM27L supernatants ranged from 182–236 ng/ml. Most were >200 ng/ml. Human IgG1/κ was undetectable in CONTROL supernatants. Cells from twelve high-producing TM27 wells were expanded into T25 flasks. Single vials were frozen as backup cultures and stored under liquid nitrogen. Cells from two CONTROL wells were also expanded to T25 flasks and frozen.

First limiting-dilution plating of CHO transfectants

The four highest-producing wells were selected for limiting-dilution plating in 96-well plates: wells #1B1 (232.6 ng/ml), 1D6 (233.3 ng/ml), 2B2 (235.5 ng/ml) and 2C1 (236.0 ng/ml). For each well, three plates were established in selective media: one at 1 cell/well and two at 0.5 cell/well.

Supernatants from the first round of cloning were screened by human IgG1/κ ELISA. Cells from 90 high-producing wells were expanded to 24-well plates and allowed to grow to confluency. Supernatants of 12 of these cultures were assayed by human IgG1/κ ELISA and by flow cytometry. Concentrations in the human IgG1/κ ELISA ranged from 211–1048 ng/ml. All samples stained HPB cells (mean channel fluoresence ranged from 46.5 to 169.9) and did not stain Jurkat cells. The six highest-producing clones were expanded and frozen (as backups) in liquid nitrogen. Of these, the two highest-producing clones (1B1-C7 and 2B2-H9) were selected to continue into subsequent rounds of cloning.

Two primary cultures of CONTROL constructs were also placed through one round of limiting-dilution plating in 96-well plates. One clone of each was selected and expanded. Supernatants were assayed and shown to give no detectable signal on the human IgG1/κ ELISA (page 640–83). Cells were frozen and are stored in liquid nitrogen.

Expansion of uncloned cultures to roller bottle scal* for antibody purification

Two primary cultures (1B1 and 2B2) were expanded in order to produce sufficient material for TM27 antibody purification. The cells were expanded to 2L roller bottles and adapted to lower serum concentration (via T25 in 10% serum→T75 in 10% serum→3×T75 in 5% serum→3×2L bottles in 1% serum) (page 640–24). The 2L bottles were established on day 1, and fed (by replacing ½ volume with fresh media with 1% serum) on days 2, 5 and 8. First harvest was on day 10, second on day 12 and third on day 15. Harvested supernatants were spun and stored at −20° C. until purification.

Purification of antibody on Protein A column

Supernatants from the 2B2 cultures were pooled (total volume of 2.7 liters) and filtered through a 0.22 micron nylon membrane. Human IgG1 ELISA indicated that the total amount of starting material was 1090 mg. Antibody was purified on a Prosep-A (Protein A) column, eluted with 0.1M citrate at pH 5.0, 4.0 and 3.0. Eluates were dialyzed into PBS. Amounts of purified antibody in the eluted fractions were measured by human IgG1 ELISA. The pH 3.0 fraction contained most of the purified antibody, while a small amount was found in the pH 4.0 fraction. The human IgG1 ELISA was repeated to obtain more precise concentration measurements Total yield of TM27 (pH 3.0 plus pH 4.0 fractions) was 960 mg.

Protein-A Purification of Antibodies from NSO Transfectant Culture Supernatant

The antibodies from NSO transfectant culture supernatants were purified on a Protein A column substantially as described above.

characterization of TM 27 Antibody from NSO Myeloma Cell Lines

The TM27 mAb purified from the culture supernatants of NSO transfectants using Protein A column chromatography was used to stain HPB-ALL cells (Vβ 5.2) and Jurkat (Vβ 8.1) cells as a negative control in comparison with mouse mAb, TM23, and chimeric TM27. TM27 stained positively on HPB-ALL but not Jurkat.

To determine the specificity of TM27, normal PBL T cells were stained with TM27 in comparison with TM23 mAb. Both the TM27 and TM23 mAbs stained ~3.0% of total human PBL T cells. A competition assay was set up in which a fixed concentration of FITC labeled TM23 aAb was added to various concentrations of unlabeled 4H11 or TM27 mAb. The antibody mixtures were then used to stain HBP-ALL cells. Both the unlabeled TM23 and TM27 blocked staining by the FITC labeled TM23. To determine whether TM27 can comodulate with CD3 antigen, HPB-ALL cells were incubated with various concentration of TM27 or TM23 mAb overnight and then stained with anti-CD3 mAb. The results indicated that TM27 as well as TM23 could cause the endocytosis of TCR/CD3 complex.

A Scatchard analysis was performed to measure the binding affinity of TM27 on HPB-ALL cells. In both the Scatchard and competition (with TM23 mAb) assay, the results indicated that TM27 maintained approximately the same affinity (Kd=2.0×10$^{-\kappa}$ M$^{-1}$), and could compete well with 4H11 mAb.

Figure 4:
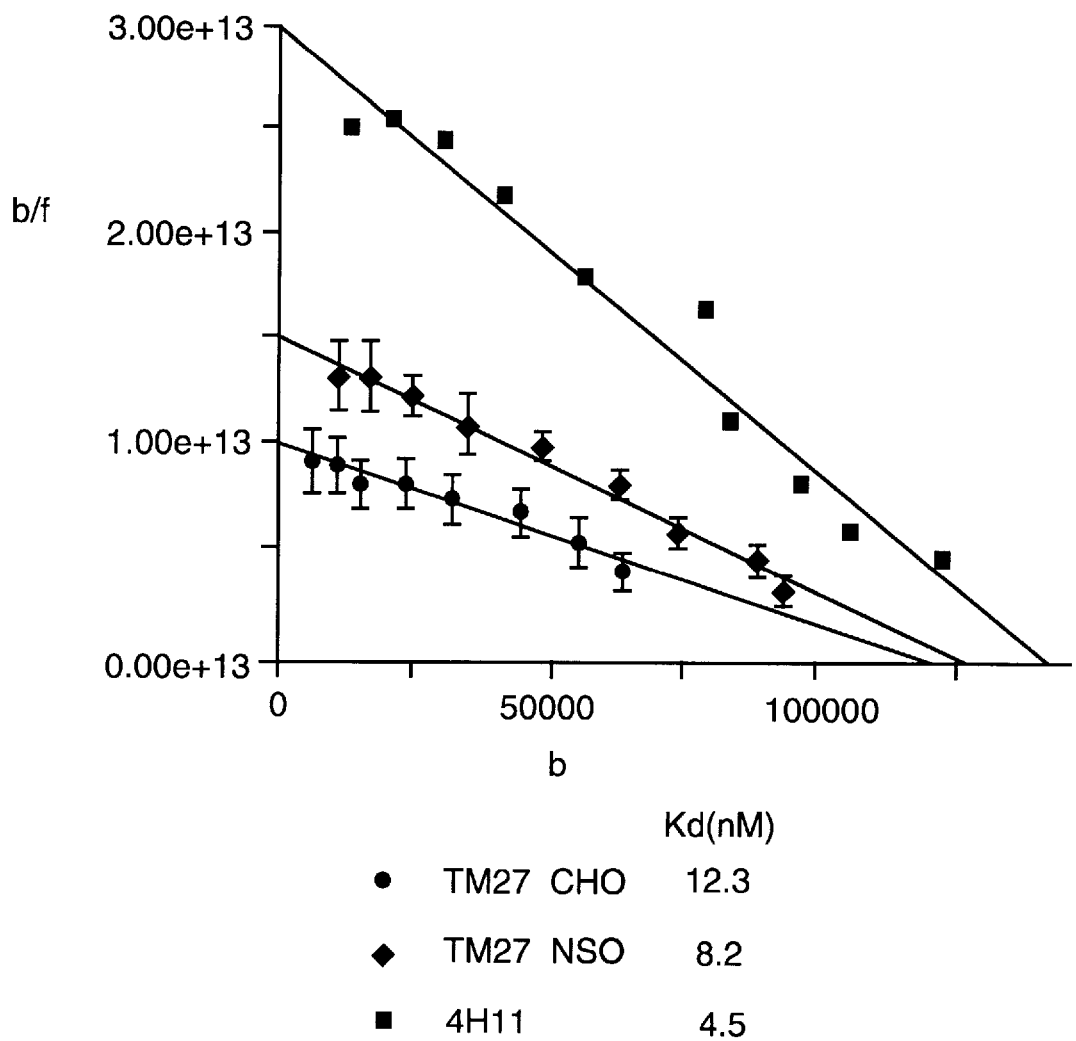
FIG. 4 depicts a Scatchard plot of the experiment shown in FIG. 3.

Comparison of TM27L/NSO and TM27L/CHO in a competition assay with 4H11 was also performed and the results are depicted in FIG. 3. A Scatchard analysis was performed and the results are depicted in FIG. 4.

Second limiting-dilution plating of CHO transfectants

A limiting-dilution plating was set up as above. Wells were screened on the human IgG1 ELISA. Cells from six wells of each (1B1 -C7 and 2B2-H9) were expanded to 24-well plates and assayed by human IgG1 ELISA. The two highest-producing clones from each were expanded and frozen in liquid nitrogen. The highest-producing clones from each were selected for the final round of subcloning.

Third limiting-dilution plating of CHO transfectants

A limiting-dilution plating was set up as above. Wells were screened on the human IgG1 ELISA. Cells from six wells of each (1B1 -C7 and 2B2-H9) were expanded to 24-well plates and assayed by human IgG1 ELISA. The three highest-producing clones from each were expanded to T25 flasks and frozen in liquid nitrogen. A single clone from each was expanded to a T75 flask. At this time, Geneticin was dropped from the media, thus removing selection for neo'. Selection for DHFR was retained. Supernatants were assayed by human IgG1 ELISA. The 1B1 -C7 clone produced 4.69 mg/10$^6$ cells/day. The 2B2-H9 clone produced 2.65 mg/10$^4$ cells/day. The C7 isolate was therefore chosen as the final clone and the H9 isolate was designated as an alternate clone.

Preparation of frozen cell stocks

The final clone chosen above was expanded to five T225 flasks to provide a sufficient number of Tells to establish a bank of frozen cell stocks. Cells were harvested from these flasks and pooled. The pooled suspension contained 98.3% viable cells. The total viable cell count was 1.58×10$^4$, sufficient to prepare the desired number of 72 vials at 2×10$^6$ cells/vial. Cells were frozen and labelled "TM27L-662–35". In addition, the alternate H9 clone was expanded to one T225 flask to establish a small frozen cell bank. Cells harvested from this flask were 97.3% viable. The suspension contained sufficient cells to prepare 9.7 vials at 2×10$^6$ cells/vial (page 662–69). Cells were frozen in liquid nitrogen and labelled as "TM27L-662–89".

Testing of cells revived from frozen stock

Viability and Mycoplasma Testing

One vial of frozen cell stock TM27L-662–35 was thawed and recovered in αMEM. Cell viability was determined to be 88% by trypan blue staining. A confluent culture grown from this vial was tested for mycoplasma contamination using a Bionique Testing Laboratories kit. The test detected no contamination. In addition, one vial of frozen cell stock TM27L-662–89 was thawed. Cell viability was determined to be 93.8% by trypan blue staining. A confluent culture grown from this vial was tested for mycoplasma contamination as above. The test detected no contamination. Both cultures were expanded to T75 flasks and cell culture supernatants assayed by human IgG1 ELISA. The TM27L-662–35 clone produced 3.24 $\mu$g/10$^6$ cells/day, and the TM27L-662–89 clone produced 2.52 $\mu$g/10$^6$ cells/day ) In a second assay, TM27L-662–35 produced 3.03 $\mu$g/10$^4$ cells/day, and TM27L-662–89 produced 2.74 $\mu$g/10$^6$cells/day.

Expression of TM27L-662–35 to roller bottle scale for antibody purification

The TM27L-662–35 culture was expanded in order to produce sufficient material for TM27L antibody purification. The cells were expanded to 2L roller bottles and adapted to lower serum concentration (via T25 in 10% serum to T75 in 10% serum to 3× T75 in 5% serum to 3×2L bottles in 1% serum). The 2L bottles were established on day 1 and fed (by replacing ½ volume with fresh media with 1% serum) on days 2, 5, 7 and 9. First harvest was on day 12, second on day 14 and third on day 16. Harvested supernatants were spun, filtered and stored at −70° C. until purification.

Purification of antibody on Protein A column

Supernatants from the TM27L-662–35 cultures were pooled for a total volume of 5.1 liters. Antibody was bound to a Prosep-A (Protein A) column and eluted with 0.1M citrate at pH 5.0 and 3.0. The pH 3.0 eluate was dialyzed into PBS. Amounts of purified material and antibody in the starting material and eluted fractions were measured by human IgG1/kappa ELISA. The pH 3.0 fraction contained approximately 3.9 mg of antibody in 25 ml. The material was concentrated on a Centriprep-30 concentrator (Amicon) and the human IgG1/ kappa ELISA was repeated. Total yield of TM27L was ~3.2 mg at 1.6 mg/ml.

Primary characterization of purified antibody

Flow cytometry was performed on ~2.5 mg of material from each of the pH 3.0 and pH 4.0 fractions and TM27 purified from NSO cells. Intensity of staining on HPB cells, as indicated by mean channel fluorescence, was measured as follows: 283.46 for the pH 3.0 fraction; 321.98 for the pH 4.0 fraction; 506.79 for NSO-derived TM27. On Jurkat cells, staining was at background level for all samples.

EXAMPLE 2

Sequences of CDR Grafted TM27 Antibodies Compared to Human Framework Cassettes

```
TM27 V_K

1         D I Q M T Q S P S S L S A S V G D R V T I T C S A S Q G I S N Y L N W Y Q Q T P G K A P K L L I Y Y      50
REI       = = = = = = = = = = = = = = = = = = = = = = Q = = = D = I K = = = = = = = = = = = = = = = = = = E
TM23      = = = = = = T T = = = = = = L = = = = = = S = = = = = = = = = = = K = D G T V = = = = = =
WAL       = = = = = = = = = = = = = = = = = = = = = R = = = S = = = = = = = = = = = K = = = = = = = = = = A

51        T S S L H S G V P S R F S G S G S G T D Y T F T I S S L Q P E D I A T Y Y C Q Q Y S K L P R T F G Q    100
REI       A = N = Q A = = = = = = = = = = = = = = = = = = = = = = = = = = = = = = = = = Q S = = Y = = = =
TM23      = = = = = = = = = = = = = = = = = = = S L = = = N = E = = = = = = = = = = = = = = = = = = = = G
WAL       A = = = Q = = = T = = = = = = = = = = = F = L = = = = = = = = = = S = = = = = = = = S Y S T L I = = = =

101       G T K L Q I T (SEQ ID NO: 2)                                                                          107
REI       = = = = = = = = (SEQ ID NO: 34)
TM23      = = = = E = K (SEQ ID NO: 35)
WAL       = = R = E = K (SEQ ID NO: 36)

TM27 VH

1*        Q V Q L Q E S G P G L V R P S Q T L S L T C T V S G F S L T A Y G V N W V R Q P P G R G L E W L G M    50
NEWM      = = = = E Q = = = = = = = = = = = = = = = = = = = = S T F S N D Y Y T = = = = = = = = = = = = I = Y
TM23      = = = = K = = = = = = = = A = = = S = = I = = = = = = = = = = = = = = = = = = = = = = K = = = = = = =
HIL       = = K = V Q A = G = V = Q = G R S = R = S = I A = = = T F S N = = MH = = = = A = = K = = = = V A V

51        I W G D G N T D Y N S A L K S R V T M L K D T S K N Q F S L R L S S V T A A D T A V Y Y C A R D R V   100
NEWM      V F Y H = T S = D T T P L R = = = = = = V = = = = = = = = = = = = = = = = = = = = = = = = N L I
TM23      = = = = = = = = = = = = = = = = = L S I S = = N = = S = V F = K M N = L Q T D = = = R = = = = = = = = =
HIL       = = Y N = S R = Y = G D S V = G = F = I S R = N = = R T L Y M Z M N = L R T E = = = = = = = = = = P

101       T A T L Y A M D Y W G Q G S L V T V S S (SEQ ID NO: 4)                                               120
NEWM      A G C I D V      = = = = = = = = = = = = = (SEQ ID NO: 37)
TM23      = = = = = = = = = = = = = = T S = = = = = = (SEQ ID NO: 38)
HIL       P I L = A F S F = = = = = = V L = = = = (SEQ ID NO: 39)
```

*HuVHL has L AT #48
TM27L with Leucine at position 48 of heavy chain (SEQ ID NO: 5).
TM27I with Isoleucine at position 48 of heavy chain (SEQ ID NO: 6).
TM27.1 with FS to VF (78–79) changes (SEQ ID NO: 7).
TM27.2 with VTML/T to LSIS/N (67–70/73) changes (SEQ ID NO: 8).
TM27.3 with V to R (92) changes (SEQ ID NO: 9).

EXAMPLE 3

Scatchard Analysis of TM23

| Exp | Kd | Receptors/cell |
|---|---|---|
| 617:096 | 3.27e-8 M | 3.04e5 |
| 617:115 | 2.30e-8 M | 2.43e5 |
| 617:119 | 2.46e-8 M | 2.46e5 |

Mean
Kd = 2.52 (±0.67) e-8 M
Receptors/cell = 2.64e5

| Exp | Kd | Receptors/cell |
|---|---|---|
| 613:78 | 1.48e-8 M | 3.31e4 |
| 613:82 | 1.14e-8 M | 2.47e4 |

Mean
Kd = 1.31 (±0.24) e-8 M
Receptors/cell = 2.89e4

EXAMPLE 4

Summary of Work on TM27I

TX27I (48) in COS/CHO:

cDNA was prepared from the CDR-grafted V regions in HSO producing line, amplified by PCR, sequenced.

DNA fragments were cloned into pTCSLNeo in cDNA configuration.

The plasmid was co-transfected with pTCSLDH-FRTM27κ into COS and CHO.

Positive ELISA results of human IgG1/κ expression from COS cell supernatant indicated that the plasmids constructs were good.

CHO cell transfectants were selected, expanded and cloned. The cells were frozen in $LN_2$ after one cloning.

EXAMPLE 5

Amino acid sequence data derived from 16G8 cDNA heavy chain (SEQ ID NO:40)

```
              10          20          30          40          50
              *           *           *           *           *
T T R A P   R S S H S   V I S T E   H R P L T   M D S R L   N L V F L   V L I L K   G V Q C D   V Q L V E   S G G G L 60          70          80          90          100
              *           *           *           *           *
V Q P G G   S R K L S   C A A S G   F T F S N   F G M H W   V R Q A P   D K G L E   W V A Y I   S S G S S   T I Y Y A 110         120         130         140         150
              *           *           *           *           *
D T L K G   R F T I S   R D N P K   N T L F L   Q M T S L   R S E D T   A M Y Y C   A R R G E   G A M D Y   W G Q G T 160         170
              *           *
S V T V S   S A K T T   P P S V Y   P L A P G
```

```
              10          20          30          40          50
              *           *           *           *           *
I S Q G T   K F K Y T   M D F Q V   Q I F S F   L L I S I   S V V M S   R G E N V   L T Q S P   A I M S A   S L G E K 60          70          80          90          100
              *           *           *           *           *
V T M S C   R A S S S   V N Y I Y   W Y Q Q K   S D A S P   K L W I Y   Y T S N L   A P G V P   T R F S G   S G S G N 110         120         130         140         150
              *           *           *           *           *
S Y S L Y   I S S M E   G E D A A   T Y Y C Q   Q F T S S   P F T F G   S G T K L   E I K R A   D A A P T   V S I F P

153
*
P S S
```

PROTEIN SEQUENCING DATA:
H = DVQLVE?GGGLVQPG (SEQ ID NO: 42)
L = ENVLTQ (SEQ ID NO: 43)

EXAMPLE 6

Summary of work on TM29

Hybridomas were prepared substantially as in Example 1 and cDNA (depicted in Example 5) was isolated.

Isolated cDNAs (H and κ) (from the 16G8 hybridoma) were cloned into M13 vectors.

Human framework ($V_{KOL}$/$Vk_{REI}$) was introduced through mutagenesis.

CDR-grafted V regions were cloned into myeloma expression vectors.

Humanized antibodies (~1 mg each) were purified from NSO transfectants for preliminary evaluation.

Four different TM29's have been made:

TM29 (SEQ ID NO:3)
TM29.1 (SEQ ID NO:44) with SS to AA (23–24) changes.
TM29.2 (SEQ ID NO:45) with S to P (75) change.
TM29.3 (SEQ ID NO:46) with GV/F to AM/Y (92–93/95) changes.

DETAILED EXPERIMENTATION-TM29

Isolation of the human kappa chain constant region by the PCR method.

Using the undigested plasmid pSV184DH-Neo/DNS-$V_\kappa C_\kappa$ (pSVHuk which contains the human kappa chain constant region) PCR was performed with two primers (one forward, one reverse) to isolate the constant region. The oligomers (primers) were obtained from Operon. The PCR reaction reagents were from the GeneAmp DNA amplification reagent kit with AmpliTaq (Perkin-Elmer Cetus). The PCR reactions were set up in three different concentrations of $Mg^{2+}$. Aliquots of the PCR products were analyzed on a 1% agarose gel. The PCR product from the first sample of $Mg^{2+}$ (concentration 1.5 mM) was chosen. The primers, which flank the C region, were designed containing restriction enzyme sites for cloning purposes. Thus, the amplified DNA was digested with EcoRI (at the 3' end). The site at the 5' end (PvuII) was not digested. The digested DNA fragment was then run on a 1% agarose gel and the 300 bp band excised. The DNA was extracted from the gel and a small aliquot was analyzed on a 1% agarose gel to determine quality and to estimate quantity. The 300 bp band appeared to be clean and the total amount of DNA estimated to be ~140 ng.

Human kappa chain constant region cloned into the pBS KS+ vector and sequenced.

The EcoR I -digested DNA fragment of the human kappa chain constant region was inserted into the vector pBS KS+, which had been digested with Sma I and EcoR I, using T4 DNA ligase. This ligation mixture was used to transform *E. coli* DH5α competent cells. Single colonies were picked and used to inoculate 24 liquid cultures. DNA was prepared from each of the cultures. Each DNA sample was digested with PvuII (5' end of $C_\kappa$) and EcoRI (3' end of $C_\kappa$), and analyzed on a 2% agarose gel. Due to difficulty in separating the lower range bands (300 bp), the DNA samples were digested with PvuII only. After analysis on a 2% agarose gel, 19 out of 24 were correct for $C_K$ insert. Samples #1–5 (of the 19 correct samples) were chosen to be sequenced, using T7 and T3 primers (sequences in the vector flanking the insert). Other sequencing reagents were from the Sequenase Version 2.0 kit (USB). Sample #5 proved to have correct sequence for the human kappa chain constant region.

Human kappa chain constant region cloned into the mammalian expression vector—pTCSLDHFR* to become pTCSLC$_k$DHFR*

The human kappa chain constant region was isolated from the pBS KS+ vector (Sample #5) using PvuII and EcoRI restriction enzymes. However, due to the previous problem of band separation, a second digest was performed with the construct pBS/Human $C_k$. The second digest involved EcoRI and XbaI (located 5' to PvuII site) yielding a fragment ~300 bp. This fragment was then gel purified and subjected to a PvuII digest, to remove the remaining small fragment of vector at the 5' end of the $C_k$. This final fragment was gel purified and then analyzed on a 1% agarose gel for quality and to estimate quantity. The $C_k$ DNA appeared to be a clean band at ~280 bp and the total quantity estimated to be ~135 ng.

Due to the existence of three EcoRI sites in the expression vector, PTCSLDHFR*, it was determined that cloning into the PvuII site only would be best. Since the $C_k$ DNA was prepared PvuII-EcoRI, the EcoRI end was repaired (to form blunt end) using Klenow fragment. The repaired, blunt-ended $C_{78}$ DNA was ligated to the PTCSLDHFR* vector which hat been PvuII digested and phosphatase treated (using calf intestinal phosphatase). This ligation mixture was used to transform E. coli DH5α competent cells. Single colonies were picked and used to inoculate 24 liquid cultures. DNA was prepared from each. All DNA samples were digested with PvuII and HindIII, and analyzed on a 1% agarose gel. It was determined that five samples, out of 24, contained the $C_K$ insert in the correct orientation. Sample #7 was chosen for continuation.

Replacement of the mutant DHFR* gene with the wild type DHFR gone.

For the expression of the vector PTCSLC$_K$DHFR* in CHO(dhfr)DUX B11 cells, the DHFR* gene was replaced with the DHFR gene. DNA from pTCSLC$_k$DHFR* sample #7 as well as pSV2-DHFR (plasmid obtained from Dr. Paul Berg, Department of Biochemistry, Stanford University Medical School) was digested with restriction enzymes HindIII and BglII, to isolate the respective gene fragments. Upon analysis, it was determined that an additional BglII site in the pTCSLC$_K$DHFR* vector removed a portion of the polyA site also, which would interfere with the vector function. Therefore, the digests were repeated using HindIII and BamHI. The (DHFR*)pTCSLC$_k$ portion of the vector was treated with phosphatase. Then both the isolated fragments (pTCSLC$_k$ and DHFR) were gel purified, and analyzed on a 1% agarose gel for quality and to estimate quantity. Both bands appeared to be clean and estimated to be of similar concentration, ~40–50 ng/ml. The DHFR gene was ligated to the pTCSLC$_k$ vector using T4 DNA ligase. The ligation mixture was used to transform E. coli DH5α competent cells. Single colonies were picked and used to inoculate 24 liquid cultures. DNA was prepared from each. The DNA was analyzed by restriction enzyme digestion with HindIII and BamHI. From 24 cultures, 23 had the correct bands indicating the insertion of the DHFR gene into the pTCSLC$_k$ vector. Sample #22 was selected for further use.

Cloning the PCR isolated human kappa chain V region into the CHO vector PTCSLC$_k$DHPR.

The cDNA for the kappa chain V region for 16G8 had been gel purified and digested with the appropriate restriction enzymes. A small aliquot of the DNA sample was analyzed on a 1% agarose gel to estimate quantity and to verify the quality. An extra (contaminating) band was observed at ~800 bp and the concentration was estimated at 1.25 ng/ml. The V region was ligated to the PTCSLC$_k$DHFR vector, which had been digested with restriction enzymes XhoI and PvuII and phosphatase-treated. The ligation mixture was used to transform E. coli DH5α competent cells. Yield of transformant colonies was very low. Single colonies were picked and used to inoculate twelve liquid cultures. DNA was prepared from each, digested with XhoI and PvuII and analyzed on a 1% agarose gel. There were four positive samples: #1, #14, #7 and #10. Each of the positive samples was sequenced. The PCR isolated TM29 gamma chain V region was cloned into the CHO vector pTCSLCg1NeoApa'. Double strand sequencing of the human kappa chain V region The four samples from 16G8 (#1, #4, #7 and #10) were sequenced for both strands. The reverse strand was sequenced entirely, through the restriction enzyme sites (3'-5'; PvuII-XhoI) using the primer HUCK5PR. Both samples #1 and #4 appeared to have correct sequence, sample #7 did not sequence, and sample #10 had the wrong sequence. For samples #1 and #4, the forward strand sequence was determined using two different primers, PTCSFOR and PTCSFWD. Full length sequence through the restriction enzyme sites (5'-3'; XhoI-PvuII) was obtained by combining the sequences yielded from each of the primers. A small area of compression was seen to be present in the forward strands which was not resolved with either of the primers or by using a sequencing method that alleviates such compressions. However, the reverse strands proved to have correct sequence in this area. Both samples #1 and #4 appeared to have correct sequence, with sample #4 chosen to be used for mammalian cell transfection.

Co-transfection of TM29 light and heavy chain plasmids into COS and CHO cells.

Both Cos-1 and CHO(dhfr')DUX B11 cells were used in the co-transfection of TM29 light and heavy chain plasmids. The CHO DUX B11 cell line was obtained from Biogen, Inc. and originally was derived by Dr. Lawrence Chaisin (Columbia University).

For the Cos-1 cell transfection, 5 mg of each undigested TM29 plasmid (pTCSLHuV$_K$16GC$_K$DHFR and pTCSLHuV$_H$16GC$_g$1NeoApa'; TM29–4 and TM29-26, respectively) was precipitated in ethanol and resuspended in H$_2$O at a 1 mg/ml concentration. The plasmids were then co-transfected into 3.8×10$^6$ cells by electroporation, using a BioRad Gene Pulser at 250V, 960 mFD. The transfected cells were resuspended in Dulbecco's Modified Eagle's medium (DMEM) and placed in culture for three days. Control vector plasmids (pTCSLDHFRApa and pTCSLNeoApa') were prepared and co-transfected similarly to the TM29 plasmids. The subsequent transfected cells were resuspended and cultured similarly to the TM29 transfected Cos cells.

For the CHO DUX B11 cell transfection, 5 mg of each TM29 plasmid (as above) was digested with the restriction enzyme AatII to yield a linear fragment of DNA, precipitated in ethanol and resuspended in H$_2$O at a 1 mg/ml concentration. The plasmids were then co-transfected into 5×10$^6$ cells by electroporation, as above. The transfected cells were resuspended in α Minimal Essential medium (αMEM) supplemented with thymidine, adenosine and deoxyadenosine (non-selective medium) and placed in culture for three days. Control vector plasmids (as above) were prepared and co-transfected similarly to the TM29 plasmids. The subsequent transfected cells were resuspended and cultured similarly to the TM29 transfected CHO cells.

Analysis of TM29 transfected Cos call supernatant by human $IgG_{fk}$ ELISA.

After three days in culture, the TM29 transfected Cos cells appeared to be confluent. Therefore, the supernatant was collected and the cells were discarded. Human IgG production by the cells was determined from the culture supernatant using the human $IgG_{fk}$ ELISA. The supernatant IgG was captured by a mouse anti-human $IgG_f$ Fc antibody, which had been coated on a 96-well plate, then detected by a horseradish peroxidase-conjugated goat anti-human Igκ antibody and color development with o-phenylenediamine (OPD). The supernatant IgG concentrations were determined by comparing optical density measurements to a curve generated by a purified human $IgG_{fk}$ antibody of known concentration. The TM29 transfected Cos cell supernatant yielded a human IgG concentration of 201.3 ng/ml. The control DNA transfected Cos cell supernatant yielded a human IgG concentration of 0 ng/ml.

Selection of TM29 transfected CHO cells

After three days in culture, the TM29 transfected CHO cells appeared to be confluent. Therefore, the cells were treated with 0.25% trypsin (in Hank's Balanced Salt solution) to dissociate them from the culture flasks. The cells were collected, centrifuged and the supernatant removed. The cell pellet was resuspended in αMEM selection media at $2\times10^6$ cells/ml and plated at 1 ml/well in a 24-well plate. The αMEM selection media had a dual selection capability, lacking nucleotide supplements and replacing FBS with dialyzed FBS to select for $DHFR^+$ on $pTCSLHuV_{k}16GC_{k}DHFR$, and adding Geneticin (G-418) to select for neo' on $pTCSLHuV_{H}16GC_{k}1NeoApa'$.

Analysis of TM29 transfected CHO call supernatant by human $IgG_{fk}$ ELISA and by flow cytometry.

After 14 days in selection media, TM29 transfected CHO cell supernatants were collected from each well and assayed using the human $IgG_fκ$ ELISA. The human IgG concentration in the TM29 transfected CHO cell supernatants ranged 144.6 ng/ml-291.9 ng/ml, with an average concentration of 240.5 ng/ml. The human IgG concentration in the control DNA transfected CHO cell supernatants was 0 ng/ml.

Supernatants from the three highest producing wells for the TM29 transfected CHO cells (2C3, 2C4, 2B6) and one well for the control DNA transfected CHO cells (3D4) were also assayed by flow cytometry. The three TM29 samples, 2C3, 2C4 and 2B6, stained Jurkat cells positively (mean channel fluorescence ranged 186.61–290.01) and did not stain HPB cells positively (mean channel fluorescence ranged 11.77–13.82). The control sample, 3D4, did not stain Jurkat cells positively (mean channel fluorescence 11.96).

Cloning of TM29 transfected CRO cells by limiting dilution

The three highest producing wells for the TM29 transfected CHO cells (2C3, 291.9 ng/ml; 2C4, 289.7 ng/ml; 2B6, 289.5 ng/ml) were chosen for cloning by limiting dilution. For each of the wells, the cell concentrations were diluted in αMEM selection media and plated at 2 cells/well, 1 cell/well, and 0.5 cell/well in 96-well plates. Ten days after cloning, colony growth was observed in numerous wells on each of the 0.5 cell/well plates for 2C3, 2C4 and 2B6. Therefore, supernatants from all wells from each of the 0.5 cell/well plates were collected and assayed using the human $IgG_fκ$ ELISA, All wells that exhibited cell growth were positive in the ELISA. A total of 24 of the highest producing wells (10 from 2C3, 14 from 2B6) were chosen for expansion into a 24-well plate and grown to confluency. Supernatants were collected from each well and assayed using the human $IgG_fκ$ ELISA. The human IgG concentration ranged 0.7 mg/ml–4.8 mg/ml, with an average concentration of 2.9 mg/ml. Supernatants from the six highest producing wells for the TM29 transfected CHO clones (1C7, 1D9, 1G2, 2G1, 2G10, 2H2a) were then assayed by flow cytometry. All six samples stained Jurkat cells positively (mean channel fluorescence ranged 313.68–356.87) and did not stain HPB cells positively (mean channel fluorescence ranged 7.59–8.16). Each of the six samples was expanded to a 25 cm$^2$ flask, frozen and stored under liquid nitrogen. The three highest producing wells (2C3-1G2, 2C3-2G10, 2C3-2H2a) were chosen for subcloning.

The one well for control DNA transfected CHO cells (3D4) was cloned by limiting dilution similar to the TM29 wells. By diluting the cell concentration 10-fold lower than desired, no colony growth was observed ten days after cloning. Therefore, a fresh culture was started from a frozen vial (3D4). Cloning by limiting dilution was repeated using this new culture. Sixteen days after cloning, six of the most confluent wells from the 0.5 cell/well plates (1B5, 1C11, 1D6, 2E7, 2F3, 2F9) were chosen for expansion into a 24-well plate. Each well was subsequently expanded to a 25 cm$^2$ flask and then to a 75 cm$^2$ flask and grown to confluency. Supernatants were collected from each flask and assayed using the human $IgG_fκ$ ELISA. The human IgG concentration was 0 ng/ml. Each flask was then frozen and stored under liquid nitrogen.

Expansion of uncloned TM29 transfected CHO call cultures to roller bottle scale

The three highest producing wells for the TM29 transfected CHO cells (2C3, 291.9 ng/ml; 2C4, 289.7 ng/ml; 2B6, 289.5 ng/ml) were also chosen for expansion into 25 cm$^2$ flasks as uncloned cultures. At this time, one vial of each of the TM29 cultures (as well as one vial of the control DNA transfected CHO cell culture) was frozen and stored under liquid nitrogen. Each of the uncloned cultures was then expanded to a 75 cm$^2$ flask. From one 75 cm$^2$ flask, each culture was expanded to 3 75 cm$^2$ flasks while decreasing the serum concentration in the αMEM medium from 10% to 5%. Each of the 75 cm$^2$ flasks for both 2C3 and 2B6 was then expanded to a 2L roller bottle. All 3 75 cm$^2$ flasks for 2C4 were frozen and stored under liquid nitrogen. Once the cultures were in the roller bottles, the serum concentration in the αMEM medium was decreased again, from 5% to 1%. After nine days in culture, the 2B6 bottles appeared to be confluent while the 2C3 bottles appeared to be ~25% confluent. The supernatants from all 2B6 and 2C3 bottles were collected on Day 9 Day 14, and Day 16, after which the cells were discarded. The collected supernatants were centrifuged and stored and stored at −20° C. An aliquot of each of the three harvested supernatants for both 2B6 and 2C3 was assayed using the human $IgG_fκ$ ELISA. The total quantity of human IgG for 2B6 was determined to be 820 mg; for 2C3, 1923 mg.

Subcloning of TX29 transfected CHO cell clones by limiting dilution

The three highest producing wells for the TM29 transfected CHO cell clones (2C3-1G2, 4.8 mg/ml; 2C3-2H2a, 4.1 mg/ml; 2C3-2G10, 4.0 mg/ml) were chosen for subcloning by limiting dilution. Fourteen days after subcloning, colony growth was observed in numerous wells on each of the 0.5 cell/well plates for 1G2, 2G10 and 2H2a. Therefore, supernatants from those wells possessing colony growth were collected and assayed using the human IgG$_f$κ ELISA. All wells exhibiting cell growth were positive in the ELISA, yielding a cloning efficiency of 100%. A total of 24 of the highest producing wells (2 from 2H2a, 5 from 2G10, 17 from 1G2) were chosen for expansion into a 24-well plate and grown to confluency. Supernatants were collected from each well and assayed using the human IgG$_f$κ ELISA. The human IgG concentration ranged 1.2 mg/ml–9.2 mg/ml, with an average concentration of 4.2 mg/ml. Supernatants from the four highest producing wells for the TM29 transfected CHO subclones (2G5, 2H12, 1H6, 2E9) were also assayed by flow cytometry. All four samples stained Jurkat cells positively (mean channel fluorescence ranged 211.51–292.45) and did not stain HPB cells positively (mean channel fluorescence ranged 8.36–8.80). Each of the four samples was expanded to a 25 cm² flask.

Second subcloning of TM29 transfected CHO cell clones by limiting dilution

The two best TM29 transfected CHO cell clones (2C3-1G2-2G5 and 2C3-1G2-1H6), based on the combined results of the ELISA and flow cytometry data, were chosen for a second subcloning by limiting dilution. At this time, one vial of each of the clones (as well as one vial of each of 2C3-1G2-2H12 and 2C3-1G2-2E9) was frozen and stored under liquid nitrogen. Twelve days after subcloning, colony growth was observed in numerous wells on each of the 0.5 cell/well plates for 2G5 and 1H6. Therefore, supernatants from those wells possessing colony growth were collected and assayed using the human IgG$_f$κ ELISA. All wells exhibiting cell growth were positive in the ELISA, yielding a cloning efficiency of 100%. A total of 24 of the highest producing wells (20 from 2G5, 4 from 1H6) were chosen for expansion into a 24-well plate (#646–101) and grown to confluency. Supernatants were collected from each well and assayed using the human IgG$_f$κ ELISA. Due to lost activity with the human IgG$_f$κ standard used in the assay, the concentrations for the unknown samples could not be determined. Therefore, the highest producing wells were determined by optical density. The six highest producing wells (5 from 2G5, 1 from 1H6) were chosen for expansion into 25 cm² flasks, then into 75 cm² flasks and grown to confluency. Supernatants were collected from each flask and assayed using the human IgG$_f$κ ELISA. The human IgG concentration ranged 14.6 mg/ml–21.2 mg/ml, with an average concentration of 18.6 mg/ml. Supernatants from the six flasks for the TM29 transfected CHO subclones (1B5, 1D1, 1F11, 2B10, 2F5, 2F9) were then assayed by flow cytometry (#646–122). All six samples stained Jurkat cells positively (mean channel fluorescence ranged 304.51–383.00) and did not stain HPB cell positively (mean channel fluorescence ranged 8.67–10.25).

Preparation of a frozen cell stock for the TM29 transfected CHO cell clone

The TM29 transfected CHO cell clone chosen to prepare a frozen cell stock was 2C3-1G2-1H6-2F5. This clone was expanded from one 75 cm² flask to five 225 cm² flasks in order to provide a sufficient number of cells to establish a frozen cell bank for research purposes. The frozen cell bank was prepared following the SOP TMB1-001.00. The cells were treated with trypsin, collected from each flask and pooled. The pooled cell suspension was found to contain $3.2 \times 10^4$ cells, with a 99% viability. Seventy-two vials were prepared, each containing $2 \times 10^6$ cells in a 1 ml volume. All vials for the clone have been labelled TM29-646-132.

EXAMPLE 7

Sequences of CDR Grafted TM29 Antibodies Compared to Other Framework Regions

TM29 Vk

```
1      D I Q M T Q S P S S L S A S V G D R V T I T C R A S S S V N Y I Y W Y Q Q T P G K A P K L L I Y Y T    50
REI    = = = = = = = = = = = = = = = = = = = = = = Q = = Q D I I K Y L N = = = = = = = = = = = = = = = E A
16G8   E N V L = = = = A I M= = = L = E K = = MS = = = = = = = = = = = = = = = K S D A S = = = W= = = =
HIC    E = V L = = = = G T = = L = P = E R A = L S = = = = = Q = =SSSYLA= = = = K = = Q = = R = = = = G A

51     S N L A P G V P S R F S G S G S G T D Y T F T I S S L Q P E D I A T Y Y C Q Q F T S S P F T F G Q G     101
REI    = = = Q A = = = = = = = = = = = = = = = = = = = = = = = = = = = = = = Y Q = L = Y = = = = = =
16G8   = = = = = = = = T = = = = = = = = = N S = S L = = = = ME G = = A = = = = = = = = = = = = = = S =
HIC    = S R = T = I = D = = = = = = = = = = = F = L = = = R = E = _ = F = V = = = = = Y G = = = W= = = = =

102    T K L Q I T (SEQ ID NO: 1)                                                                              106
REI    = = = = = = (SEQ ID NO: 47)
16G8   = = = E = K (SEQ ID NO: 48)
HIC    = = V E = K (SEQ ID NO: 49)
```

TM29 VH

```
1      E V Q L V E S G G G V V Q P G R S L R L S C S S S G F T F S N F G M H W V R Q A P G K G L E W V A Y     50
KOL    Q = = = = = = = = = = = = = = = = = = = = = = = = = I = = S Y A= Y= = = = = = = = = = = = = = = I
16G8   D = = = = = = = = = = L = = = = = G = R K = = = A A = = = = = = = = = = = = = = = = D = = = = = = = =
WEA    Q = = = = D = = = = L = E = = G = = = = = = = = A = = = = = = A N D= N = = = = = = = = = = = = L S F

51     I S S G S S T I Y Y A D T L K G R F T I S R D N S K N T L F L Q M D S L R P E D T G V Y F C A R R G     100
KOL    = WD D G = D Q H = = = S V = = = = = = = = = = = = = = = = = = = = = = = = = = = = = = = = D =
16G8   = = = = = = = = = = = = = = = = = = = = = = = = = P = = = = = = = = T = = = S = = = A M= Y= = = = =
WEA    = G G S G= = = = = = = = S V = = = = = = = = = N B = = = S = Y = = = S = = = A = = = A= Y Y = =   = =

101    E G A M          D Y W G Q G T P V T V S S (SEQ ID NO: 3)
KOL    G H G F C S S A S C F G P = = = = = = = = = = = = = (SEQ ID NO: 50)
16G8   = = = =                   = = = = = = = S = = = = = (SEQ ID NO: 51)
WEA    WL L              N       = = = = = L = = = = = = (SEQ ID NO: 52)
```

TM29 (SEQ ID NO: 3) with the sequences of 1st version
TM29.1 (SEQ ID NO: 44) with SS to AA (23–24) changes
TM29.2 (SEQ ID NO: 45) with S to P (75) change
TM29.3 (SEQ ID NO: 46) with GV/F to AM/Y (92–93/95) changes

EXAMPLE 8
Scatchard Analysis of TM29 mAb

Scatchard analyses of TM29 and 16G8 antibodies were performed in three independent experiments. The table below shows the $K_d$ determined from each of the experiments.

| Exp. | TM29 $K_d$ (M) | 16G8 $K_d$ (M) |
|---|---|---|
| 1 | $1.45 \times 10^{-9}$ | $2.86 \times 10^{-9}$ |
| 2 | $1.65 \times 10^{-9}$ | $2.65 \times 10^{-9}$ |
| 3 | $1.15 \times 10^{-9}$ | $2.44 \times 10^{-9}$ |
| Mean | $1.42 \times 10^{-9}$ | $2.65 \times 10^{-9}$ |

EXAMPLE 9
Summary of Work on Chimeric TM29

Chimerics in COS and CHO:
V(D)J region cDNAs were cloned into CHO cell expression vectors, pTCSLNeo (H) and PTCSLDHFR (k) in cDNA configuration.

Expression plasmids were co-transfected into COS and CHO.

Ab concentration in supernatant from COS cells ~35 ng/ml.

CHO cell transfectants were analyzed (by FACS and ELISA), cloned once, and were amplified with MTX (20 nM, 100 nM and 500 nM).

The antibody concentration from unamplified CHO cell clones was ~3 μg/ml; and stained Jurkat cells positively. The unamplified clones were frozen in $LN_2$.

EXAMPLE 10
Expression of Chimeric 16G8 in COS and CHO Cells 16G8 Chimeric

Light chain and heavy chain constructs contained complete mouse V region with human constant region in the same expression vectors used for CDR-grafted constructs: pTCSDHFR link pTCSNeo link-the constructs had double selection capability.

COS cell transfectants—35 ng/ml
CHO cell transfectants—16 positive wells/54 wells

|  | ng/ml | | corrected for volume |
|---|---|---|---|
| 1A1 | 151.6 | | |
| 1A6 | 166.6 | | |
| 1B3 | 107.2 | | |
| 1B6 | 179.6 | | |
| 1D2 | 101.0 | | |
| 1D5 | 215.1 | * | 2.2 μg/ml |
| 2A4 | 199.8 | | |
| 2B1 | 184.5 | | |
| 2B2 | 213.8 | * | 2.1 μg/ml |
| 2B4 | 130.6 | | |
| 2C2 | 119.6 | | |
| 2C6 | 214.4 | * | 2.1 μg/ml |
| 2D3 | 216.6 | * | 2.2 μg/ml |
| 2D6 | 139.7 | | |
| 3A1 | 198.7 | | |
| 3A2 | 172.2 | | | all expanded to 25 cm² flasks
*Flow cytometry performed.

EXAMPLE 11
Summary of Work on TM29
TM29

TM29 in COS/CHO:

cDNA was prepared from the CDR-grafted V regions in NSO producing line, amplified by PRCR, sequenced.

DNA fragments were cloned into pTCSLNeo (H) and pTCSLDHFR (k) in cDNA configuration.

Plasmids were co-transfected into COS and CHO.

Supernatant from COS cells contains ~2 μg/ml Ab.

CHO cell transfectants secreted ~3 μg/ml Ab before cloning and amplification, supernatant stained Jurkat cells positively. Cell bank from the best unamplified Ab producer was prepared after three times of cloning.

The CHO cell lines were amplified under various concentration of MTX.

EXAMPLE 12
Comparison of TM27L, TM27I and TM23 in 4H11-FITC Competition Assay Exp 1:

$$\frac{\text{slope } TM23}{\text{slope } TM27L} = 1.56$$

$$\frac{\text{slope } TM23}{\text{slope } TM27I} = 2.04$$

Exp 2:

$$\frac{\text{slope } TM23}{\text{slope } TM27L} = 1.82$$

$$\frac{\text{slope } TM23}{\text{slope } TM27I} = 2.44$$

Compared with TM23, the values from both TM27L and TM27I are all <3 fold.

EXAMPLE 13
TM27 Methotrexate Amplification

| | | Productivity (micrograms/10* cells/day) Methotrexate Level (nM) | | | | |
|---|---|---|---|---|---|---|
| | | 0 | 20 | 100 | 10–200 | 20–200 |
| C7 | *7/30 | 27 | nd | nd | nd | 265.8 |
| | *7/22 | 3.5 | nd | 19.2 | 14.7 | 34.2 |
| | 7/6 | 2.6 | nd | nd | 9.1 | nd |
| | 6/25 | 2 | 4.8 | 4.5 | nd | nd |
| | 6/18 | 3 | 8.9 | nd | nd | nd |
| H9 | *7/30 | 22.7 | nd | nd | nd | 181.9 |
| | &7/22 | 3.9 | nd | 9.4 | 11.6 | 34.4 |
| | 6/25 | 1.5 | 1.8 | 4.7 | 3.6 | nd |
| | 6/18 | 1.8 | 1.5 | nd | nd | nd |

*No interassay comparison.

| | | Intra-assay relative value | | | | |
|---|---|---|---|---|---|---|
| | | 0 | 20 | 100 | 20-100 | 20–200 |
| C7 | *7/30 | 1 | nd | nd | nd | 9.8 |
| | *7/22 | 1 | nd | 5.5 | 4.2 | 9.8 |
| | 7/6 | 1 | nd | nd | 3.5 | nd |
| | 6/25 | 1 | 2.4 | 2.3 | nd | nd |
| | 6/18 | 1 | 3.0 | nd | nd | nd |
| H9 | *7/30 | 1 | nd | nd | nd | 8.0 |
| | *7/22 | 1 | nd | 2.4 | 3.0 | 8.8 |
| | 6/25 | 1 | 1.2 | 3.1 | 2.4 | nd |
| | 6/18 | 1 | 0.8 | nd | nd | nd |

-continued

| | Productivity (micrograms/10* cells/day) Methotrexate Level (nM) | | | | |
|---|---|---|---|---|---|
| | | Status | | | |
| | 0 | 20 | 100 | 20–100 | 20–200 |
| C7 8/11 | fm | fm,s,sf4 | fm | fm | fm,s* |
| H9 8/11 | fm | discard | fm,s,f2 | fm | fm,s* |

Key
fm = froze 1 tube mixed culture
s = subculture by one limiting dilution
s* = first limiting dilution in progress
f# = froze one vial of each of # wells

I claim:

1. A humanized antibody having an amino acid sequence that comprises CDRs from a monoclonal antibody having a specificity for a select subpopulation of T cells expressing the Vβ5.2 or Vβ5.3 variable region of the T cell antigen receptor beta chain, in conjunction with select variable framework residues also derived from said monoclonal antibody, wherein, the humanized antibody comprises the TM27 Vk amino acid sequence (SEQ ID NO:2):

1 DIQMTQSPSSLSASVGDRVTITCSASQGISNYLNWYQQT

PGKAPKLLIYY 50

51 TSSLHSGVPSRFSGSGSGTDYTFTISSLQPEDIATYYCQ

QYSKLPRTFGQ 100

101 GTKLQIT 107, and further comprises an amino acid sequence selected from the group consisting of the TM27 VH amino acid sequence (SEQ ID NO:4):

1 QVQLQESGPGLVRPSQTLSLTCTVSGFSLTAYGVNWVR

QPPGRGLEWLGM 50

51 IWGDGNTDYNSALKSRVTMLKDTSKNQFSLRLSSVTA

ADTAVYYCARDRV 100

101 TATLYAMDYWGQGSLVTVSS 120, the TM27 VH sequence wherein amino acid residue 48 is replaced with isoleucine (I) (SEQ ID NO:6),
the TM27 VH sequence wherein amino acid residues 78 and 79 are valine (V) and phenylalanine (F) (SEQ ID NO:7),
the TM27 VH sequence wherein amino acid residues 67 to 70 having the sequence V T M L are replaced with L S I S, respectively, and amino acid residue 73 is asparagine (N) (SEQ ID NO:8), and
the TM27 VH sequence in which amino acid residue 92 is an arginine (R) (SEQ ID NO:9).

2. The humanized antibody of claim 1 which is of isotype IgG.

3. The humanized antibody of claim 1 wherein one or more residues in the constant domains of the Ig has been altered in order to alter the isotype of said Ig.

4. The humanized antibody of claim 1 produced by recombinant DNA technology.

5. A method for producing a humanized antibody of claim 1, which method comprises:

d) transforming a host cell with said construct of step c); and e) culturing said host cell so transformed to produce said humanized antibody.

6. The method of claim 5 wherein the host cell is a CHO cell.

7. The humanized antibody of claim 2, said isotype subclass being IgG1.

8. A humanized antibody having an amino acid sequence that comprises CDRs from a monoclonal antibody having a specificity for a select subpopulation of T cells expressing the Vβ5.2 or Vβ5.3 variable region of the T cell antigen receptor beta chain, in conjunction with select variable framework residues also derived from said monoclonal antibody, wherein, the humanized antibody comprises the TM27 Vk amino acid sequence (SEQ ID NO:2):

1 DIQMTQSPSSLSASVGDRVTITCSASQGISNYLNWYQQT

PGKAPKLLIYY 50

51 TSSLHSGVPSRFSGSGSGTDYTFTISSLQPEDIATYYCQ

QYSKLPRTFGQ 100

101 GTKLQIT 107, and the TM27 VH amino acid sequence (SEQ ID NO:4):

1 QVQLQESGPGLVRPSQTLSLTCTVSGFSLTAYGVNWVRQ

PPGRGLEWLGM 50

51 IWGDGNTDYNSALKSRVTMLKDTSKNQFSLRLSSVTAA

DTAVYYCARDRV 100

101 TATLYAMDYWGQGSLVTVSS 120.

9. A method of depleting in a population of T cells the number of T cells expressing the β chain variable region 5.2 or 5.3 of the T cell receptor comprising exposing said T cells expressing said β chain variable region 5.2 or 5.3 to an effective concentration of the humanized antibody of claim 1 or claim 8.

10. The method of claim 9 wherein said exposing is performed in vivo.

11. The method of claim 10 wherein said exposing is performed in a patient.

12. The method of claim 5, wherein said $V_H$ and $V_L$ CDR oligonucleotide primers are inserted into the same expression vector.

13. A composition comprising a humanized antibody of claims 1 or 8 in combination with a pharmaceutically acceptable excipient.

* * * * *

UNITED STATES PATENT AND TRADEMARK OFFICE
CERTIFICATE OF CORRECTION

PATENT NO. : 5,861,155
DATED : January 19, 1999
INVENTOR(S) : Lin, et al.

It is certified that error appears in the above-indentified patent and that said Letters Patent is hereby corrected as shown below:

In the Claims:

Claim 5, line 1, after "which method comprises:" insert
-- a) inserting the $V_H$ CDR1 (SEQ ID NO. 22), CDR2 (SEQ ID NO. 23) and CDR3 (SEQ ID NO. 24) oligonucleotide primers comprising SEQ ID NO.s 22, 23 and 24 into an expression vector;
b) inserting the $V_L$ CDR1 (SEQ ID NO. 25), CDR2 (SEQ ID NO. 26) and CDR3 (SEQ ID NO. 27) oligonucleotide primers comprising SEQ ID NO.s 25, 26 and 27 into an expression vector;
c) introducing select human framework amino acids through mutagenesis into the expression vector of a) and b), thereby forming a CDR grafted construct; --

Signed and Sealed this

Twelfth Day of October, 1999

*Attest:*

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,861,155
DATED : January 19, 1999
INVENTOR(S) : Lin

It is certified that error appears in the above-identified patent and that said Letters Patent is hereby corrected as shown below:

```
column 17, line 17, after "TM27L-662-35", insert
   "(ATCC Designation No.: CRL 11949)".

column 32, line 41, after ""TM27L-662-35"", insert
   "(ATCC Designation No.: CRL 11949)".

column 32, line 50, after "TM27L-662-35", insert
   "(ATCC Designation No.: CRL 11949)".

column 33, line 1, after "TM27L-662-35", insert
   "(ATCC Designation No.: CRL 11949)".

column 33, line 3, after "TM27L-662-35", insert
   "(ATCC Designation No.: CRL 11949)".

column 33, line 49, after "TM27L-662-35", insert
   "(ATCC Designation No.: CRL 11949)".

column 42, line 30, after "TM29-646-132", insert
   "(ATCC Designation No.: CRL 11948)".
```

Signed and Sealed this

Twentieth Day of June, 2000

Attest:

Q. TODD DICKINSON

*Attesting Officer*  *Director of Patents and Trademarks*